US007384912B2

(12) United States Patent
Stewart

(10) Patent No.: US 7,384,912 B2
(45) Date of Patent: *Jun. 10, 2008

(54) TREATMENT OF BONE DISORDERS WITH SKELETAL ANABOLIC DRUGS

(75) Inventor: Andrew F. Stewart, Pittsburgh, PA (US)

(73) Assignee: Osteotrophin, LLC, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/216,511

(22) Filed: Aug. 31, 2005

(65) Prior Publication Data

US 2006/0025342 A1  Feb. 2, 2006

Related U.S. Application Data

(63) Continuation of application No. 10/340,484, filed on Jan. 10, 2003, now Pat. No. 7,015,195.

(60) Provisional application No. 60/347,215, filed on Jan. 10, 2002, provisional application No. 60/353,296, filed on Feb. 1, 2002, provisional application No. 60/368,955, filed on Mar. 28, 2002, provisional application No. 60/379,125, filed on May 8, 2002.

(51) Int. Cl.
*A61K 38/29* (2006.01)
*C07K 14/635* (2006.01)

(52) U.S. Cl. .............................. 514/2; 514/12; 530/324

(58) Field of Classification Search ...................... None
See application file for complete search history.

(56) References Cited

U.S. PATENT DOCUMENTS

| | | | |
|---|---|---|---|
| 4,656,250 A | 4/1987 | Morita et al. ............... 530/324 |
| 4,771,124 A | 9/1988 | Rosenblatt et al. .......... 530/324 |
| 5,229,489 A | 7/1993 | Kanmera et al. ............ 530/324 |
| 5,589,452 A | 12/1996 | Krstenansky et al. ......... 514/12 |
| 5,595,760 A | 1/1997 | Cherif-Cheikh |
| 5,605,815 A | 2/1997 | Broadus et al. |
| 5,688,760 A | 11/1997 | Kemp et al. |
| 5,693,616 A | 12/1997 | Krstenansky et al. ......... 514/12 |
| 5,695,955 A | 12/1997 | Krstenansky et al. ....... 435/69.4 |
| 5,700,774 A | 12/1997 | Hattersley et al. |
| 5,703,207 A | 12/1997 | Martin et al. |
| 5,747,456 A | 5/1998 | Chorev et al. |
| 5,798,225 A | 8/1998 | Krstenansky et al. ...... 435/69.4 |
| 5,807,823 A | 9/1998 | Krstenansky et al. ......... 514/12 |
| 5,821,225 A | 10/1998 | Vickery |
| 5,821,823 A | 10/1998 | Bereza ......................... 331/57 |
| 5,840,837 A | 11/1998 | Krstenansky et al. ....... 530/324 |
| 5,847,086 A | 12/1998 | Farb et al. ................... 530/383 |
| 5,849,695 A | 12/1998 | Cohen et al. |
| 5,874,086 A | 2/1999 | Krstenansky et al. .... 424/198.1 |
| 5,977,070 A | 11/1999 | Piazza et al. |
| 6,051,686 A | 4/2000 | Krstenansky et al. ....... 530/333 |
| 6,147,186 A | 11/2000 | Gardella et al. |
| 6,273,598 B1 | 8/2001 | Keck et al. ................. 364/578 |
| 6,362,163 B1 | 3/2002 | Gardella et al. |
| 6,495,662 B1 | 12/2002 | Gardella et al. |
| 6,544,949 B1 | 4/2003 | Dong |
| 6,583,114 B2 | 6/2003 | Vickery |
| 6,756,480 B2 | 6/2004 | Kostenuik et al. |
| 6,787,518 B1 | 9/2004 | Kato et al. |
| 6,849,710 B1 | 2/2005 | Arzeno |
| 6,921,750 B2 | 7/2005 | Dong |
| 6,977,077 B1 | 12/2005 | Hock et al. |
| 7,015,195 B2 * | 3/2006 | Stewart ........................ 514/2 |
| 7,057,012 B1 | 6/2006 | Gardella et al. |
| 2002/0077281 A1 | 6/2002 | Vickery |

FOREIGN PATENT DOCUMENTS

| | | |
|---|---|---|
| DE | 4203040 A1 | 8/1993 |
| EP | 293158 A2 | 11/1988 |
| EP | 451867 B1 | 10/1991 |
| EP | 477885 B1 | 4/1992 |
| EP | 561412 B1 | 9/1993 |
| EP | 1 059 933 | 1/2003 |
| EP | 0 822 200 | 9/2004 |
| EP | 1 595 532 | 11/2005 |
| WO | WO 92/00753 | 1/1992 |
| WO | WO 92/10515 | 6/1992 |
| WO | WO 92/11286 | 7/1992 |
| WO | WO 93/06846 | 4/1993 |
| WO | WO 93/20203 | 10/1993 |
| WO | WO 94/01460 | 1/1994 |
| WO | WO 94/02510 | 2/1994 |
| WO | WO 94/03201 | 2/1994 |
| WO | WO 95/02610 A1 | 1/1995 |
| WO | WO-98/04591 | 2/1998 |
| WO | WO 98/05683 | 2/1998 |
| WO | WO 99/12561 A2 | 3/1999 |
| WO | WO-99/55310 | 11/1999 |

(Continued)

OTHER PUBLICATIONS

Abou-Samra et al., *Endocrinology*, 125: 2594-2599 (1989).

(Continued)

*Primary Examiner*—Anish Gupta
(74) *Attorney, Agent, or Firm*—Foley & Lardner LLP; Michel Morency; James F. Ewing

(57) ABSTRACT

Disclosed herein are methods for the prevention and treatment of a variety of mammalian conditions manifested by loss of bone mass, including osteoporosis. The present invention provides methods of using PTHrP, or analogs thereof, for the treatment of metabolic bone disorders that are both effective and have an increased safety.

10 Claims, 20 Drawing Sheets

FOREIGN PATENT DOCUMENTS

| WO | WO-00/10596 | 3/2000 |
| --- | --- | --- |
| WO | WO-00/18954 | 4/2000 |
| WO | WO-01/22093 | 3/2001 |
| WO | WO-01/85784 | 11/2001 |
| WO | WO-01/98348 | 12/2001 |
| WO | WO-02/28420 | 4/2002 |
| WO | WO-02/068585 | 9/2002 |
| WO | WO-03/026689 | 4/2003 |
| WO | WO-03/039534 | 5/2003 |
| WO | WO-2004/060386 | 7/2004 |

OTHER PUBLICATIONS

Abou-Samra et al., *Endocrinology*, 129: 2547-2554 (1991).
Blind et al., *Clin. Endocrinol.*, 101: 150-155 (1993).
Brown et al., *Biochem.*, 20:4538-4546 (1981).
Burtis et al., *J. Biol. Chem.*, 262: 7151-7156 (1987).
Burtis *Clin. Chem.*, 38: 2171-2183 (1992).
Carter et al., *Biochim. Biophys. Acta*, 538: 290-304 (2001).
Casey et al., *Nucl. Acid Res.*, 4: 1539 (1977).
Caufield et al., *Endocrinol.*, 123:2949-2951 (1988).
Caye et al., *J. Clin. Endocrinol., Metab.*, 81: 199-208 (1996).
Chestnut et al., *Osteoporosis Int 8* (sup pl 3): 13 (1998).
Chorev et al., *J. Bone. Min. Res.*, 4: S270 (1989).
Cohen et al., *J. Biol. Chem.*, 266:1997-2004 (1991).
Dayhoff et al., 5 Atlas of Protein Sequence and Structure, 345-352. (1978 & Suppl.).
Delmas et al., *N. Engl. J. Med.*, 337: 1641-1647 (1997).
Dempster et al., *Endocrine Reviews*, 14:690-709 (1993).
Dobnig & Turner, *Endocrinology*, 138:4607-4612 (1997).
Ettinger et al., *JAMA*, 282:637-45 (1999).
Finkelstein et al., *N. Engl J. Med.*, 331: 1618-1623 (1994).
Fitzpatrick et al., *J. Biol. Chem.*, 244: 3561-3569 (1969).
Fogelman et al., J. Clin. Endocrinol. Metab., 85:1895-1900 (2000).
Frolick et al., *J. Bone Min. Res.*, 14: 163-72 (1999).
Fujimori et al., *Endocrinology*, 130: 29-60 (1992).
Fujimori et al., *Endocrinology*, 128: 3032-3039 (1991).
Fukuyama et al., *Endocrinology*, 131: 1757-1769 (1992).
Fukayama et al., *Endocrinology*, 134: 1851-1858 (1994).
Gamse et al., *J. Bone Min. Res.*; 12(suppl): S317 (1997).
Gundberg, et al., J. Clin. Endocrinol. Metab., 83:3258-3266, (1998).
Henry et al., *J. Clin. Endocrinol. Metab.*, 82: 900-906 (1997).
Hirano et al., *J. Bone. Min. Res.*, 14: 536-545 (1999).
Hock et al., *Endocrinology*, 125: 2022-2027 (1989).
Hock et al., *J. Bone. Min. Res.*, 7: 65-72 (1992).
Hodsman et al., *J. Clin. Endocrinol. Metab.*, 82: 620-628 (1997).
Janulis et al., *Endocrinology*, 133: 713-719 (1993).
Jouishomme et al., *Endocrinology*, 130: 53-60 (1992).
Juppner et al., *J. Biol., Chem.*, 263: 8557-8560 (1988).
Karaplis A.C.,. Abstract 1052, Annual Meeting of the American Society for Bone and Mineral Research, Sep. 2002, San Antonio, TX. *J. Bone Mineral Res.*, 17(Suppl. 1), S138 (2002).
Lane et al., *J Clin. Invest.*, 102: 1627-1633 (1998).
Liberman et al., *N. Engl. J. Med.*, 333: 1437-1443 (1995).
Lindsay et al., *Lancet*, 350: 550-555 (1997).
McClung et al., *N. Engl. J. Med.*, 344: 333-40 (2001).
Merendino et al., *Science*, 231: 388-390 (1986).
Moseley et al., *Proc. Natl. Acad. Sci. USA.*, 84 5048-5052 (1987).
Munson et al., *Anal. Biochem.*, 107:220-239 (1980).
Murphy et al., J. Clin. Endocrinol. Metab., 86:1116-25 (2001).
Neer et al., *N. Engl. J. Med.*, 344: 1434-1441 (2001).
Orloff et al., *J. Biol. Chem.*, 264: 6097-6103 (1989).
Orloff et al., *J. Bone Min. Res.*, 6: 279-287 (1991).
Orloff et al., *Endocrinology*, 131: 1603-1611 (1992).
Orloff et al. *Am. J. Phsiol.*, 262: E599-E607 (1992).
PEPI Trial, *JAMA*, 276: 1389-1396 (1996).
Pines et al., *Endocrinology*, 135: 1713-1716 (1994).
Plotkin et al., *J. Clin. Endocrinol. Metab.*, 83: 2786-2791 (1998).
Reid et al., *N. Engl. J. Med.*, 346:653-61 (2002).
Roe et al., *Program and Abstracts of the 81st Annual Meeting of the Endocrine Society*, San Diego, CA, Jun. 12-15, p. 59 (1999).
Rosen et al., *J. Clin. Endocrinol. Metab.*, 86: 957-964 (2001).
Schermer, *J. Bone & Min. Res.*, 6: 149-155 (1991).
Shimizu et al., *J. Biol. Chem.*, 276: 49003-49012 (2001).
Shimizu et al., *Endocrinology*, 42: 3068-3074 (2001).
Shimizu et al., *J. Biol. Chem.*, 275: 21836-21843 (2000).
Sistare et al., *Pharmacopeial Forum*, 20: 7509-7520 (1994).
Stewart et al., *N. Engl. J. Med.*, 303: 1377-1383 (1980).
Stewart et al., *J. Clin. Endo. Metab.*, 55: 219-227 (1982).
Stewart et al., *Biochem. Biophys. Res. Comm.*, 146: 672-678 (1987).
Stewart et al., *J. Clin. Invest.*, 81: 596-600 (1988).
Stewart et al., *J. Bone Min. Res.*, 15: 1517-1525 (2000).
Strewler et al., *J. Clin. Invest.*, 80: 1803 (1987).
Vickery et al., *J. Bone Miner. Res.*, 11: 1943-1951 (1996).
Wu et al., *J. Biol. Chem.*, 271: 24371-24381 (1996).
Yang et al., *Biochem.*, 33: 7460-7469 (1994).
Yasuda et al., *J. Biol. Chem.*, 264: 7720-7725 (1989).
Stewart, A.F., "PTHrP(1-36) as a Skeletal Anabolic Agent for the Treatment of Osteoporosis;" BONE, vol. 19, No. 4; Oct. 1996; pp. 303-306.

* cited by examiner

PTHrP Peptides

| Species | Amino Acid Sequences[1] | %[2] | | SEQ ID NO: |
|---|---|---|---|---|
| Homo sapiens (Human) | 1-AVSEH QLLHD KGKSI QDLRR RFFLH HLIAE IHTAEI-36 | | | 2 |
| Equus caballus (Horse) | 1-AVSEH QLLHD KGKSI QDLRR RFFLH HLIAE IHTAEI-36 | 100 | 100 | 3 |
| Bos taurus (Cow) | 1-AVSEH QLLHD KGKSI QDLRR RFFLH HLIAE IHTAEI-36 | 100 | 100 | 4 |
| Ovis aries (Sheep) | 1-AVSEH QLLHD KGKSI QDLRR RFFLH HLIAE IHTAEI-36 | 100 | 100 | 5 |
| Canis familiaris (Dog) | 1-AVSEH QLLHD KGKSI QDLRR RFFLH HLIAE IHTAEI-36 | 100 | 100 | 6 |
| Felis catus (Cat) | 1-AVSEH QLLHD KGKSI QDLRR RFFLH HLIAE IHTAEI-36 | 100 | 100 | 7 |
| Oryctolagus cuniculus (Rabbit) | 1-AVSEH QLLHD KGKSI QDLRR RFFLH HLIAE IHTAEI-36 | 100 | 100 | 8 |
| Rattus norvegicus (Rat) | 1-AVSEH QLLHD KGKSI QDLRR RFFLH HLIAE IHTAEI-36 | 100 | 100 | 9 |
| Mus musculus (Mouse) | 1-AVSEH QLLHD KGKSI QDLRR RFFLH HLIAE IHTAEI-36 | 100 | 100 | 10 |
| Gallus gallus (Chicken) | 1-AVSEH QLLHD KGKSI QDLRR RIFLQ NLIEG VNTAEI-36 | 81 | 86 | 11 |
| Sparus aurata (Sea bream) | 1-SVSHA QLMHD KGRSL QEFKR RMWLH ELLEE VHTADD-36 | 53 | 81 | 12 |
| Takifugu rubripes (Teleost) | 1-SVSHA QLMHD KGRSL QEFRR RMWLH KLLEE VHANE-35 | 56 | 81 | 13 |

[1] Amino acids that differ from the corresponding amino acid in the human sequence are bolded; amino acids that are conservative amino acid substitution variants of the corresponding amino acids in the human sequence are bolded and underlined.
[2] Left column: % identity values; right column: % homology values.

FIG. 1

PTH Peptides

| Species | Amino Acid Sequences[1] | %[2] | | SEQ ID NO: |
|---|---|---|---|---|
| Homo sapiens (Human) | 1-SVSEI QLMHN LGKHL NSMER VEWLR KKLQD VHNF-34 | | | 15 |
| Macaca fascicularis (Macaque) | 1-SVSEI QLMHN LGKHL NSMER VEWLR KKLQD VHNF-34 | 100 | 100 | 16 |
| Equus caballus (Horse) | 1-SVSEI QLMHN LGKHL NSVER VEWLR KKLQD VHNF-34 | 97 | 100 | 17 |
| Bos taurus (Cow) | 1-AVSEI QFMHN LGKHL SSMER VEWLR KKLQD VHNF-34 | 91 | 94 | 18 |
| Sus scrofa domestica (Pig) | 1-SVSEI QLMHN LGKHL SSLER VEWLR KKLQD VHNF-34 | 94 | 97 | 19 |
| Canis familiaris (Dog) | 1-SVSEI QFMHN LGKHL SSMER VEWLR KKLQD VHNF-34 | 94 | 97 | 20 |
| Felis catus (Cat) | 1-AVSEH QLLHD KGKSI QDLRR RFFLH HLIAE IHTA-34 | 32 | 62 | 21 |
| Rattus norvegicus (Rat) | 1-AVSEI QLMHN LGKHL ASVER MQWLR KKLQD VHNF-34 | 85 | 88 | 22 |
| Mus musculus (Mouse) | 1-AVSEI QLMHN LGKHL ASMER MQWLR RKLQD MHNF-34 | 82 | 91 | 23 |
| Gallus gallus (Chicken) | 1-SVSEM QLMHN LGEHR HTVER QDWLQ MKLQD VHSA-34 | 64 | 79 | 24 |

[1] Amino acids that differ from the corresponding amino acid in the human sequence are bolded; amino acids that are conservative amino acid substitution variants of the corresponding amino acids in the human sequence are bolded and underlined.
[2] Left column: % identity values; right column: % homology values.

FIG. 2

TIP Peptides

| Species | Amino Acid Sequences[1] | %[2] | | SEQ ID NO: |
|---|---|---|---|---|
| Homo sapiens (Human) | 1-METRQ VSRSP RVRLL LLLLL LLVVP WGVRT ASGVA LPPV-39 | | | 26 |
| Mus musculus (Mouse) | 1-METCQ MSRSP RERLL LLLLL LLLVP WGTGP ASGVA LPLA-39 | 79 | 87 | 27 |

[1] Amino acids that differ from the corresponding amino acid in the human sequence are bolded; amino acids that are conservative amino acid substitution variants of the corresponding amino acids in the human sequence are bolded and underlined.

[2] Left column: % identity values; right column: % homology values.

FIG. 3

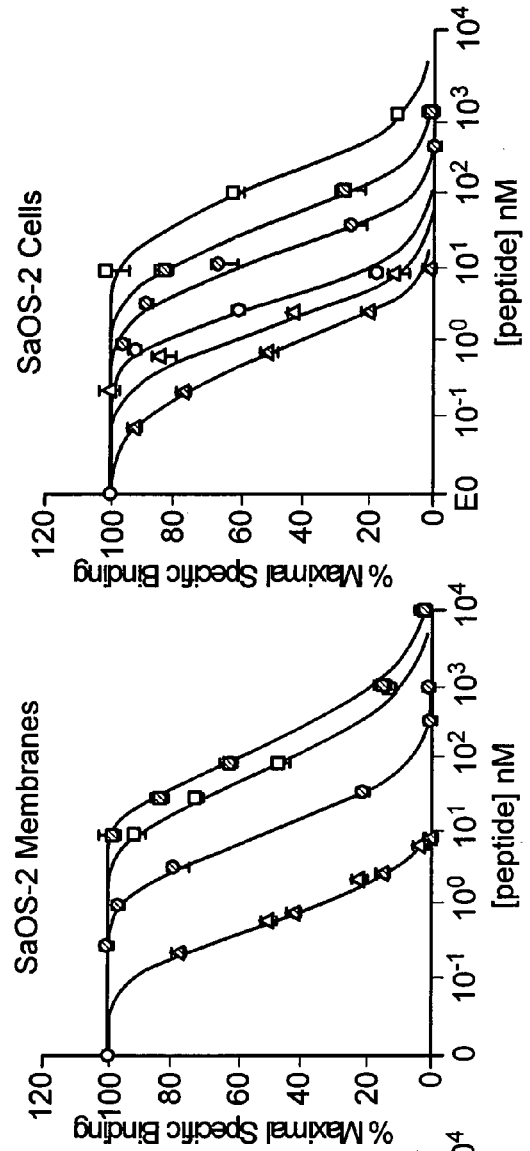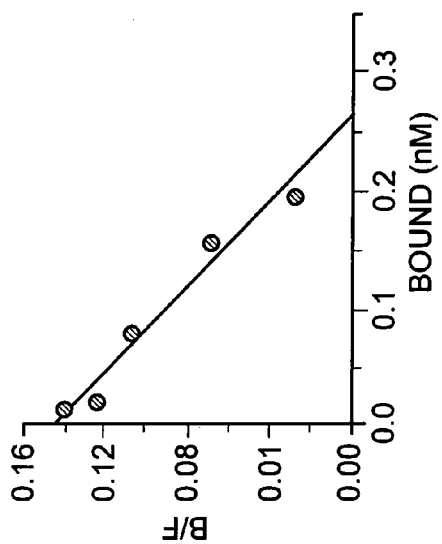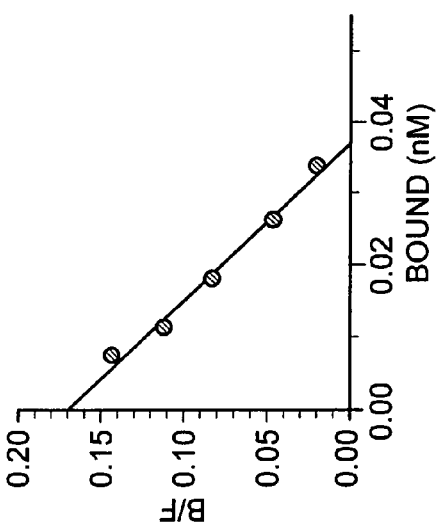
FIG. 9A  FIG. 9B  FIG. 9C
FIG. 9D  FIG. 9E  FIG. 9F

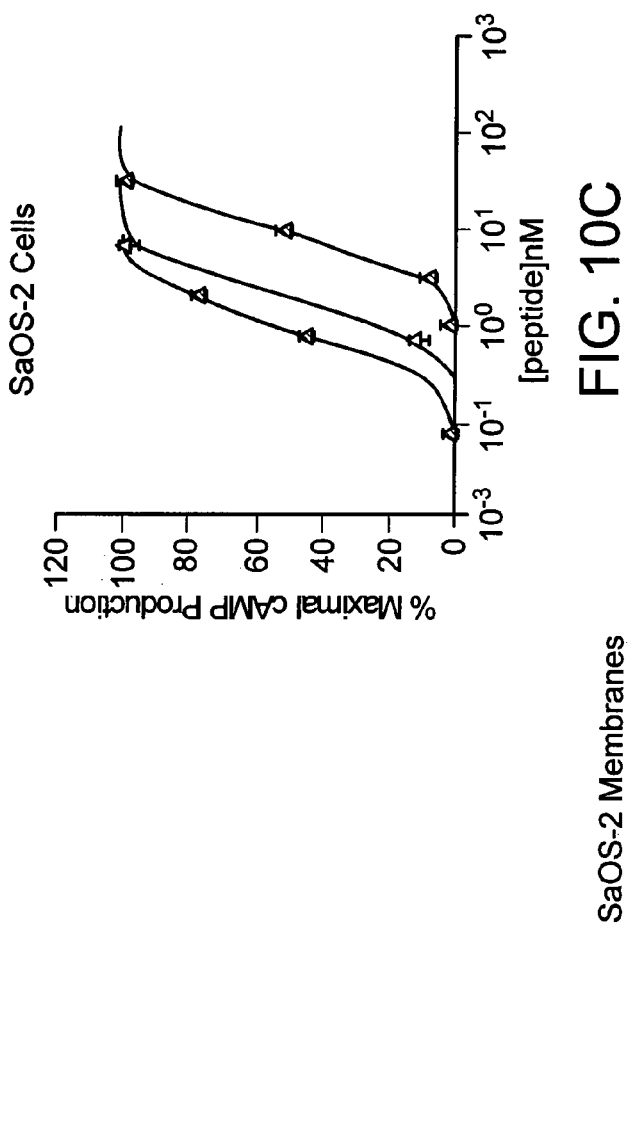
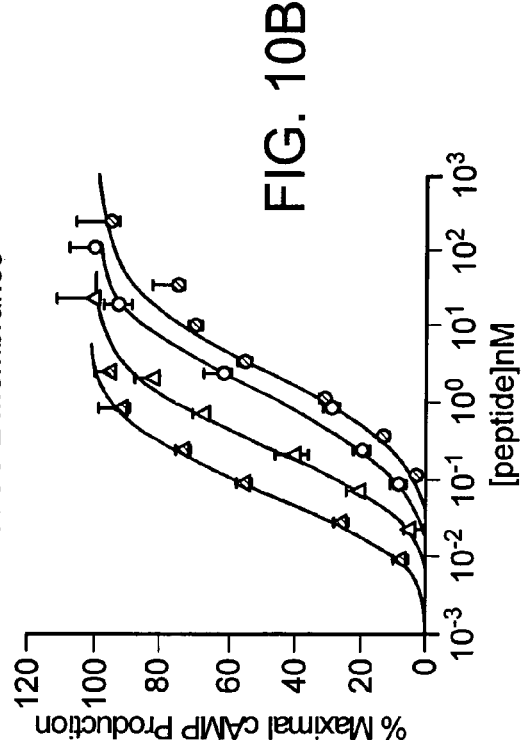
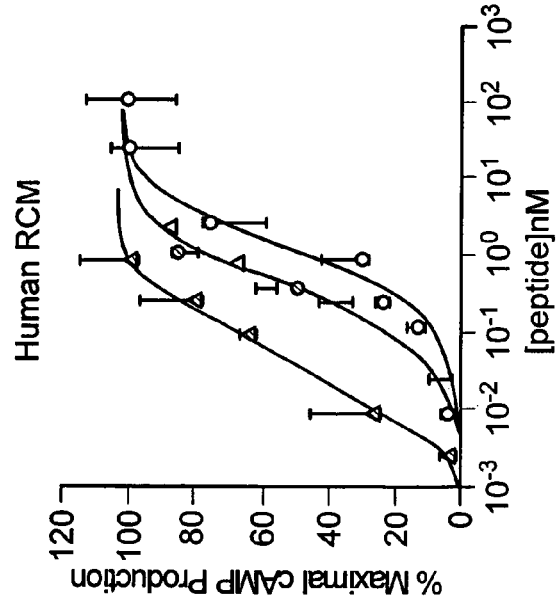
FIG. 10A
FIG. 10B
FIG. 10C

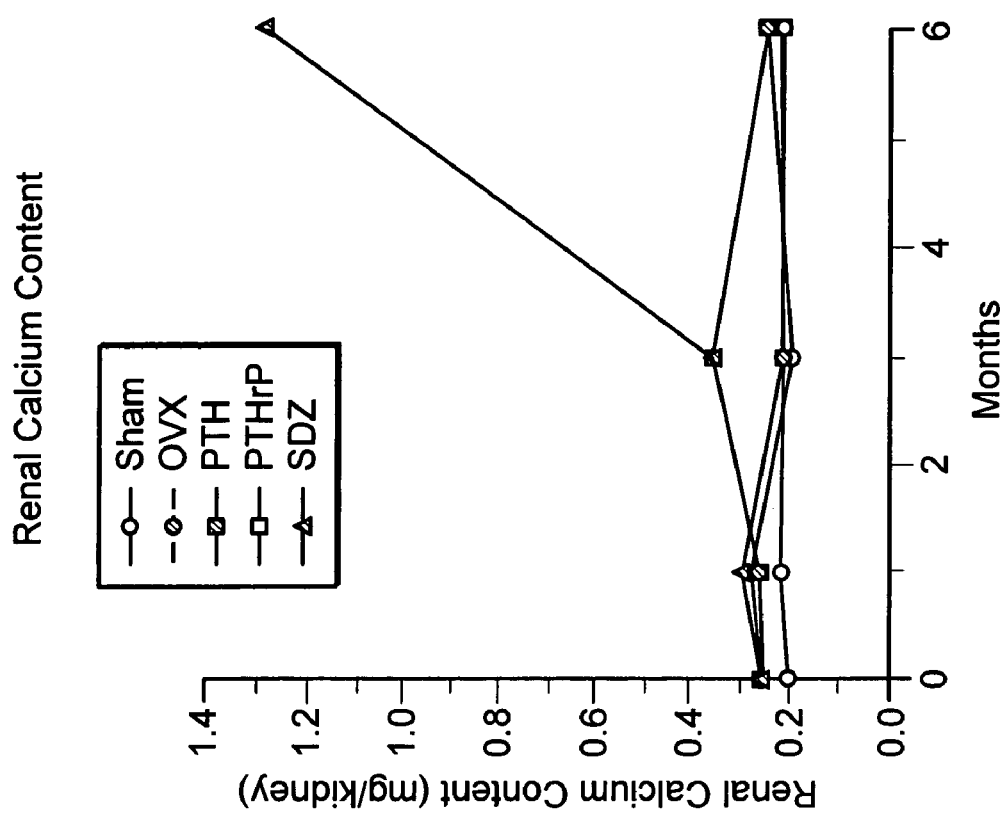
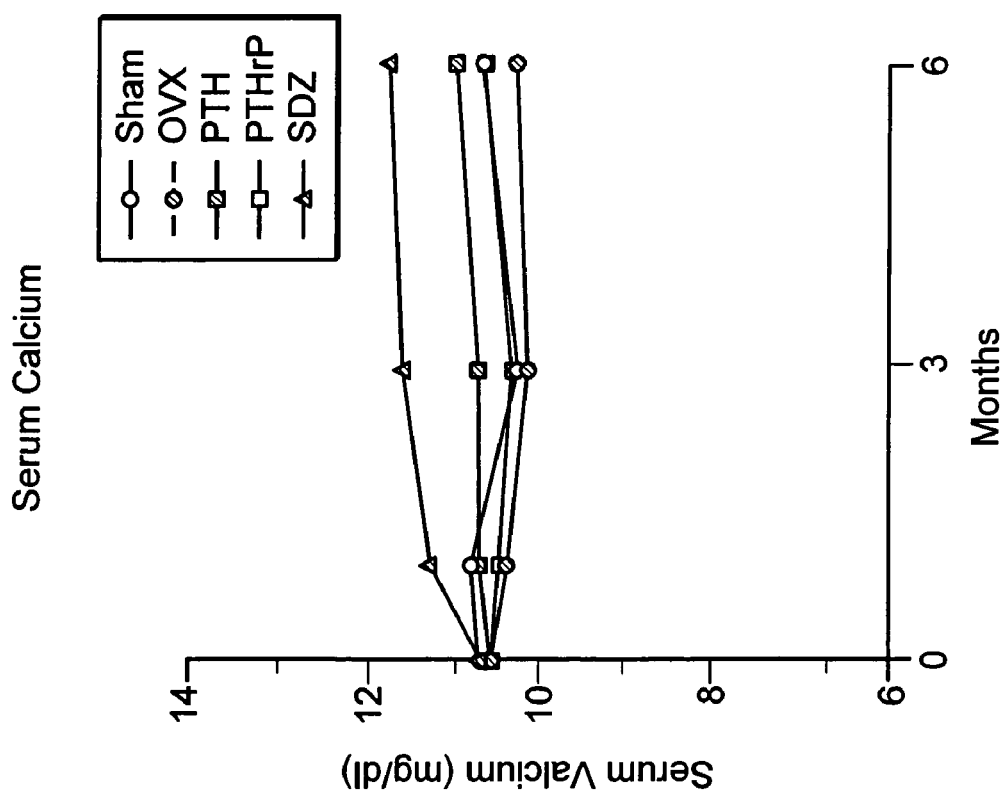
FIG. 18

```
SEQUENCE LISTING

<160> NUMBER OF SEQ ID NOS: 27

<210> SEQ ID NO 1
<211> LENGTH: 108
<212> TYPE: DNA
<213> ORGANISM: Homo sapiens

<400> SEQUENCE: 1
gctgtgtctg aacatcagct cctccatgac aaggggaagt ccatccaaga tttacggcga        60
cgattcttcc ttcaccatct gatcgcagaa atccacacag ctgaaatc                    108

<210> SEQ ID NO 2
<211> LENGTH: 36
<212> TYPE: PRT
<213> ORGANISM: Homo sapiens

<400> SEQUENCE: 2

Ala Val Ser Glu His Gln Leu Leu His Asp Lys Gly Lys Ser Ile Gln
  1               5                  10                  15

Asp Leu Arg Arg Arg Phe Phe Leu His His Leu Ile Ala Glu Ile His
                 20                  25                  30

Thr Ala Glu Ile
             35

<210> SEQ ID NO 3
<211> LENGTH: 36
<212> TYPE: PRT
<213> ORGANISM: Equus caballus

<400> SEQUENCE: 3
```

-continued

```
Ala Val Ser Glu His Gln Leu Leu His Asp Lys Gly Lys Ser Ile Gln
 1               5                  10                  15

Asp Leu Arg Arg Arg Phe Phe Leu His His Leu Ile Ala Glu Ile His
            20                  25                  30

Thr Ala Glu Ile
        35

<210> SEQ ID NO 4
<211> LENGTH: 36
<212> TYPE: PRT
<213> ORGANISM: Bos taurus

<400> SEQUENCE: 4

Ala Val Ser Glu His Gln Leu Leu His Asp Lys Gly Lys Ser Ile Gln
 1               5                  10                  15

Asp Leu Arg Arg Arg Phe Phe Leu His His Leu Ile Ala Glu Ile His
            20                  25                  30

Thr Ala Glu Ile
        35

<210> SEQ ID NO 5
<211> LENGTH: 36
<212> TYPE: PRT
<213> ORGANISM: Ovis aries

<400> SEQUENCE: 5

Ala Val Ser Glu His Gln Leu Leu His Asp Lys Gly Lys Ser Ile Gln
 1               5                  10                  15

Asp Leu Arg Arg Arg Phe Phe Leu His His Leu Ile Ala Glu Ile His
            20                  25                  30

Thr Ala Glu Ile
        35

<210> SEQ ID NO 6
<211> LENGTH: 36
<212> TYPE: PRT
<213> ORGANISM: Canis familiaris

<400> SEQUENCE: 6

Ala Val Ser Glu His Gln Leu Leu His Asp Lys Gly Lys Ser Ile Gln
 1               5                  10                  15

Asp Leu Arg Arg Arg Phe Phe Leu His His Leu Ile Ala Glu Ile His
            20                  25                  30

Thr Ala Glu Ile
        35

<210> SEQ ID NO 7
<211> LENGTH: 36
<212> TYPE: PRT
<213> ORGANISM: Felis catus

<400> SEQUENCE: 7

Ala Val Ser Glu His Gln Leu Leu His Asp Lys Gly Lys Ser Ile Gln
 1               5                  10                  15

Asp Leu Arg Arg Arg Phe Phe Leu His His Leu Ile Ala Glu Ile His
            20                  25                  30

Thr Ala Glu Ile
        35

<210> SEQ ID NO 8
```

```
<211> LENGTH: 36
<212> TYPE: PRT
<213> ORGANISM: Orycctolagus cuniculus

<400> SEQUENCE: 8

Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
            20                  25                  30

Thr Ala Glu Ile
        35

<210> SEQ ID NO 9
<211> LENGTH: 36
<212> TYPE: PRT
<213> ORGANISM: Rattus norvegicus

<400> SEQUENCE: 9

Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
            20                  25                  30

Thr Ala Glu Ile
        35

<210> SEQ ID NO 10
<211> LENGTH: 36
<212> TYPE: PRT
<213> ORGANISM: Mus musculus

<400> SEQUENCE: 10

Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
            20                  25                  30

Thr Ala Glu Ile
        35

<210> SEQ ID NO 11
<211> LENGTH: 36
<212> TYPE: PRT
<213> ORGANISM: Gallus gallus

<400> SEQUENCE: 11

Ala Val Ser Glu His Gln Leu Leu His Asp Lys Gly Lys Ser Ile Gln
1               5                   10                  15

Asp Leu Arg Arg Arg Ile Phe Leu Gln Asn Leu Ile Glu Gly Val Asn
            20                  25                  30

Thr Ala Glu Ile
        35

<210> SEQ ID NO 12
<211> LENGTH: 36
<212> TYPE: PRT
<213> ORGANISM: Sparus aurata

<400> SEQUENCE: 12

Ser Val Ser His Ala Gln Leu Met His Asp Lys Gly Arg Ser Leu Gln
1               5                   10                  15

Glu Phe Lys Arg Arg Met Trp Leu His Glu Leu Leu Glu Glu Val His
            20                  25                  30
```

Thr Ala Asp Asp
        35

<210> SEQ ID NO 13
<211> LENGTH: 35
<212> TYPE: PRT
<213> ORGANISM: Takifugu rubripes

<400> SEQUENCE: 13

Ser Val Ser His Ala Gln Leu Met His Asp Lys Gly Arg Ser Leu Gln
1               5                   10                  15

Glu Phe Arg Arg Arg Met Trp Leu His Lys Leu Leu Glu Glu Val His
            20                  25                  30

Ala Asn Glu
        35

<210> SEQ ID NO 14
<211> LENGTH: 102
<212> TYPE: DNA
<213> ORGANISM: Homo sapiens

<400> SEQUENCE: 14
tctgtgtccg agattcagtt aatgcataac cttggcaaac atttgaactc catggagcgt    60
gtagaatggc tgcgtaagaa gttgcaggat gtgcacaatt tt                      102

<210> SEQ ID NO 15
<211> LENGTH: 34
<212> TYPE: PRT
<213> ORGANISM: Homo sapiens

<400> SEQUENCE: 15

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 16
<211> LENGTH: 34
<212> TYPE: PRT
<213> ORGANISM: Macaca fascicularis

<400> SEQUENCE: 16

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 17
<211> LENGTH: 34
<212> TYPE: PRT
<213> ORGANISM: Equus caballus

<400> SEQUENCE: 17

Ser Val Ser Glu Ile Gln Leu Met His Asn Leu Gly Lys His Leu Asn
1               5                   10                  15

Ser Val Glu Arg Val Glu Trp Leu Arg Lys Lys Leu Gln Asp Val His
            20                  25                  30

Asn Phe

<210> SEQ ID NO 18
<211> LENGTH: 34
<212> TYPE: PRT
<213> ORGANISM: Bos taurus

<400> SEQUENCE: 18

Ala Val Ser Glu Ile Gln Phe Met His Asn Leu Gly Lys His Leu Ser
 1               5                  10                  15

Ser Met Glu Arg Val Glu Trp Leu Arg Lys Lys Leu Gln Asp Val His
            20                  25                  30

Asn Phe

<210> SEQ ID NO 19
<211> LENGTH: 34
<212> TYPE: PRT
<213> ORGANISM: Sus scrofa

<400> SEQUENCE: 19

Ser Val Ser Glu Ile Gln Leu Met His Asn Leu Gly Lys His Leu Ser
 1               5                  10                  15

Ser Leu Glu Arg Val Glu Trp Leu Arg Lys Lys Leu Gln Asp Val His
            20                  25                  30

Asn Phe

<210> SEQ ID NO 20
<211> LENGTH: 34
<212> TYPE: PRT
<213> ORGANISM: Canis familiaris

<400> SEQUENCE: 20

Ser Val Ser Glu Ile Gln Phe Met His Asn Leu Gly Lys His Leu Ser
 1               5                  10                  15

Ser Met Glu Arg Val Glu Trp Leu Arg Lys Lys Leu Gln Asp Val His
            20                  25                  30

Asn Phe

<210> SEQ ID NO 21
<211> LENGTH: 34
<212> TYPE: PRT
<213> ORGANISM: Felis catus

<400> SEQUENCE: 21

Ala Val Ser Glu His Gln Leu Leu His Asp Lys Gly Lys Ser Ile Gln
 1               5                  10                  15

Asp Leu Arg Arg Arg Phe Phe Leu His His Leu Ile Ala Glu Ile His
            20                  25                  30

Thr Ala

<210> SEQ ID NO 22
<211> LENGTH: 34
<212> TYPE: PRT
<213> ORGANISM: Rattus norvegicus

<400> SEQUENCE: 22

Ala Val Ser Glu Ile Gln Leu Met His Asn Leu Gly Lys His Leu Ala
 1               5                  10                  15

Ser Val Glu Arg Met Gln Trp Leu Arg Lys Lys Leu Gln Asp Val His
            20                  25                  30

Asn Phe

<210> SEQ ID NO 23
<211> LENGTH: 34
<212> TYPE: PRT
<213> ORGANISM: Mus musculus

<400> SEQUENCE: 23

Ala Val Ser Glu Ile Gln Leu Met His Asn Leu Gly Lys His Leu Ala
 1               5                  10                  15

Ser Met Glu Arg Met Gln Trp Leu Arg Arg Lys Leu Gln Asp Met His
            20                  25                  30

Asn Phe

<210> SEQ ID NO 24
<211> LENGTH: 34
<212> TYPE: PRT
<213> ORGANISM: Gallus gallus

<400> SEQUENCE: 24

Ser Val Ser Glu Met Gln Leu Met His Asn Leu Gly Glu His Arg His
 1               5                  10                  15

Thr Val Glu Arg Gln Asp Trp Leu Gln Met Lys Leu Gln Asp Val His
            20                  25                  30

Ser Ala

<210> SEQ ID NO 25
<211> LENGTH: 108
<212> TYPE: DNA
<213> ORGANISM: Homo sapiens

<400> SEQUENCE: 25
atggagaccc gccaggtgtc caggagccct cgggttcggc tgctgctgct gctgctgctg    60
ctgctggtgg tgccctgggg cgtccgcact gcctcgggag tcgccctg    108

<210> SEQ ID NO 26
<211> LENGTH: 39
<212> TYPE: PRT
<213> ORGANISM: Homo sapiens

<400> SEQUENCE: 26

Met Glu Thr Arg Gln Val Ser Arg Ser Pro Arg Val Arg Leu Leu Leu
 1               5                  10                  15

Leu Leu Leu Leu Leu Leu Val Val Pro Trp Gly Val Arg Thr Ala Ser
            20                  25                  30

Gly Val Ala Leu Pro Pro Val
            35

<210> SEQ ID NO 27
<211> LENGTH: 39
<212> TYPE: PRT
<213> ORGANISM: Mus musculus

<400> SEQUENCE: 27

Met Glu Thr Cys Gln Met Ser Arg Ser Pro Arg Glu Arg Leu Leu Leu
 1               5                  10                  15

```
Leu Leu Leu Leu Leu Leu Leu Val Pro Trp Gly Thr Gly Pro Ala Ser
            20                  25                  30

Gly Val Ala Leu Pro Leu Ala
            35
```

TREATMENT OF BONE DISORDERS WITH SKELETAL ANABOLIC DRUGS

RELATED APPLICATIONS

This application is a continuation of U.S. patent application Ser. No. 10/340,484, filed Jan. 10, 2003, now U.S. Pat. No. 7,015,195, which claims the benefit of priority under 35 U.S.C. § 119 to U.S. Ser. No. 60/347,215, filed on Jan. 10, 2002, U.S. Ser. No. 60/353,296, filed Feb. 1, 2002, U.S. Ser. No. 60/368,955, filed Mar. 28, 2002 and U.S. Ser. No. 60/379,125, filed May 8, 2002.1998, the contents of which are incorporated herein by reference.

STATEMENT REGARDING FEDERALLY SPONSORED RESEARCH OR DEVELOPMENT

This invention was made with government support under Grant NIDDK RO-01 DK 51081, awarded by The National Institutes of Health. The Government has certain rights in this invention.

FIELD OF THE INVENTION

The present invention relates generally to methods for the prevention and treatment of a variety of mammalian conditions manifested by loss of bone mass, including osteoporosis. More particularly, the present invention relates to methods of using PTHrP, or an analog thereof, for the treatment of metabolic bone disorders that are effective and have an increased safety.

BACKGROUND OF THE INVENTION

Throughout adult life, bone continually undergoes remodeling through the interactive cycles of bone formation and resorption (bone turnover). Bone resorption is typically rapid, and is mediated by osteoclasts (bone resorbing cells), formed by mononuclear phagocytic precursor cells at bone remodeling sites. This process then is followed by the appearance of osteoblasts (bone forming cells), which form bone slowly to replace the lost bone. The fact that completion of this process normally leads to balanced replacement and renewal of bone indicates that the molecular signals and events that influence bone remodeling are tightly controlled.

The mechanism of bone loss is not well understood, but in practical effect, the disorder arises from an imbalance in the formation of new healthy bone and the resorption of old bone, skewed toward a net loss of bone tissue. This bone loss includes a decrease in both mineral content and protein matrix components of the bone, and leads to an increased fracture rate of the femoral bones and bones in the forearm and vertebrae predominantly. These fractures, in turn, lead to an increase to general morbidity, a marked loss of stature and mobility, and in many cases, an increase in mortality resulting from complications.

A number of bone growth disorders are known which cause an imbalance in the bone remodeling cycle. Chief among these are metabolic bone diseases, such as osteoporosis, osteomalacia/rickets, chronic renal failure and hyperparathyroidism, which result in abnormal or excessive loss of bone mass (osteopenia).

Osteoporosis, or porous bone, is a disease characterized by low bone mass and structural deterioration of bone tissue, leading to bone fragility and an increased susceptibility to fractures of the hip, spine, and wrist. It is a devastating disease among both postmenopausal women as well as among older men. The costs at the national level for medications and hospitalizations are estimated to be in the $50,000,000 per year range at present and are likely to increase as the US population ages. At present, the mainstays of therapy are oral calcium supplements, vitamin D supplements, and a family of medications termed "anti-resorptives" which reduce osteoclastic bone resorption. These include estrogens, such as conjugated estrogens (Premarin®); selective estrogen receptor modulators (SERMs), such as raloxifene (Evista®); calcitonin (Miacalcin®); and bisphosphonates, such as alendronate (Fosamax®), risedronate (Actonel®), etidronate (Didronel®), pamidronate (Aredia®), tiludronate (Skelid®), or zoledronic acid (Zometa®). See, The writing group for the PEPI trial, *JAMA* 276: 1389-1396 (1996); Delmas et al., *N Engl J Med* 337: 1641-1647 (1997); Chestnut et al., *Osteoporosis Int* 8 (*suppl* 3): 13 (1998); Liberman et al., *N Engl J Med* 333: 1437-1443 (1995); McClung et al., *N Engl J Med* 344: 333-40 (2001). drugs are effective in slowing bone mineral loss and even cause moderate increases in lumbar spine bone mineral density in the range of 2% (calcium, vitamin D, calcitonin), 3% (raloxifene), 6% (estrogens) or 8% (bisphosphonates). In general, two to three years of administration are required to achieve effects of this magnitude. See, The writing group for the PEPI trial, *JAMA* 276: 1389-1396 (1996); Delmas et al., *N Engl J Med* 337: 1641-1647 (1997); Chestnut et al., *Osteoporosis Int* 8 (*suppl* 3): 13 (1998); Liberman et al., *N Engl J Med* 333: 1437-1443 (1995); McClung et al., *N Engl J Med* 344: 333-40 (2001).

Osteoporosis exists, in general, when skeletal mineral losses are in the range of 50% below peak bone mass, which occurs at approximately age 30. Seen from the perspective of correcting the deficit in bone mineral, complete reversal of this 50% loss would require a 100% increase in bone mass. Thus, seen from this perspective, the 2-8% increases in bone mineral density which result from anti-resorptive therapy, while clinically significant and beneficial, leaves very significant room for improvement. Since the use of anti-resorptives to prevent bone loss does not result in new bone production, the ultimate effectiveness of anti-resorptives in quantitative terms is limited. These considerations emphasize the need for the development of pharmaceutical mechanisms to produce new bone.

Recently, evidence has accumulated which clearly demonstrates that parathyroid hormone (PTH) is a very effective new member of such a new osteoporosis therapeutic armamentarium. See, Finkelstein et al., *N Engl J Med* 331: 1618-1623 (1994); Hodsman et al., *J Clin Endocrinol Metab* 82: 620-28 (1997); Lindsay et al., *Lancet* 350: 550-555 (1997); Neer et al., *N Engl J Med* 344: 1434-1441 (2001); Roe et al., Program and Abstracts of the 81st Annual Meeting of the Endocrine Society, p. 59 (1999); Lane et al., *J Clin Invest* 102: 1627-1633 (1998). PTH was first identified in parathyroid gland extracts in the 1920's. The complete amino acid sequence of PTH was determined in the 1970's. Because patients with overproduction of parathyroid hormone (i.e., hyperparathyroidism) develop a decline in bone mass (sometimes very severe), PTH has widely been seen as a catabolic skeletal agent over the past century. However, both animal and human studies have now clearly demonstrated that when administered subcutaneously as a single daily dose, (so called "intermittently"—in contrast to the continuous overproduction of PTH which occurs in patients with hyperparathyroidism), PTH can induce marked increases in bone mineral density and bone mass. Thus, PTH is very different from the anti-resorptive class of drugs. See, Finkelstein et al., *N Engl J Med* 331: 1618-1623 (1994);

Hodsman et al., *J Clin Endocrinol Metab* 82: 620-28 (1997); Lindsay et al., *Lancet* 350: 550-555 (1997); Neer et al., *N Engl J Med* 344: 1434-1441 (2001); Roe et al., Program and Abstracts of the 81st Annual Meeting of the Endocrine Society, p. 59 (1999); Lane et al., *J Clin Invest* 102: 1627-1633 (1998). While the cellular basis for this anabolic effect remains to be defined, the effects at the microscopic and physiologic level are clear: PTH when administered intermittently results in an marked activation of bone-forming osteoblasts, while activating bone-resorbing osteoclasts to a lesser extent. These effects are directionally opposite from the anti-resorptive drugs described above, which inhibit both osteoclastic and osteoblastic activity.

To put these results in quantitative terms, PTH has been shown in multiple studies to increase lumbar spine bone mineral density by approximately 10-15%, depending on the study (see, Finkelstein et al., *N Engl J Med* 331: 1618-1623 (1994); Hodsman et al., *J Clin Endocrinol Metab* 82: 620-28 (1997); Lindsay et al., *Lancet* 350: 550-555 (1997); Roe et al., Program and Abstracts of the 81st Annual Meeting of the Endocrine Society, p. 59 (1999); Lane et al., *J Clin Invest* 102: 1627-1633 (1998)). In one study, spine bone mineral density was reported to be increased by as much as 30%, when assessed using dual energy x-ray absorptiometry (DXA), and as much as 80% when using quantitative computerized tomography (QCT) of lumbar spine trabecular bone (see, Roe et al., Program and Abstracts of the 81st Annual Meeting of the Endocrine Society, 59 (1999)).

In addition to increasing bone mass, PTH has recently been demonstrated to have significant anti-fracture efficacy, both at the spine and at non-vertebral sites. PTH has been shown to reduce fractures by between 60% and 90% depending on the skeletal site and the definition of fracture. Neer et al., *N Engl J Med* 344: 1434-1441 (2001). These effects are at least as pronounced as the anti-fracture efficacy of the anti-resorptives (see, The writing group for the PEPI trial, *JAMA* 276: 1389-1396 (1996); Delmas et al., *N Engl J Med* 337: 1641-1647 (1997); Chestnut et al., *Osteoporosis Int* 8 (*suppl* 3): 13 (1998); Liberman et al., *N Engl J Med* 333: 1437-1443 (1995); McClung et al., *N Engl J Med* 344: 33340 (2001)), and may be superior. Thus, PTH appears to be the first member of a new class of anti-osteoporosis drugs, which in contrast to the anti-resorptives, have been termed the skeletal "anabolic" class of osteoporosis drugs, or "anabolics."

Parathyroid hormone-related protein (PTHrP) appears to be a second member of this class of skeletal anabolic drugs. See, Stewart et al., *J Bone Min Res* 15: 1517-1525 (2000). PTHrP is the product of a gene distinct from that which encodes PTH. PTHrP shares approximately 60% homology at the amino acid level with PTH in the first 13 amino acids, and then the sequences diverge completely. Yang et al., In: Bilezikian, Raisz, and Rodan (Eds). PRINCIPLES OF BONE BIOLOGY. Academic Press, San Diego Calif., pp. 347-376 (1996). PTHrP is initially translated as a pro-hormone that then undergoes extensive post-translational processing. One of the processed forms, or authentic secretory forms, as identified in the inventor's laboratory, is PTHrP-(1-36). Wu et al., *J Biol Chem* 271:24371-24381 (1996). PTHrP-(1-36) binds to the common PTH/PTHrP receptor, also termed the PTH-1 receptor, in bone and kidney. Everhart-Caye et al., *J Clin Endocrinol Metab*, 81: 199-208 (1996); Orloff et al., *Endocrinology*, 131: 1603-1611 (1992). PTHrP-(1-36) binds to this receptor with equal affinity to PTH, and activates the PKA and PKC signal transduction pathways with equal potency as PTH. Everhart-Caye et al., *J Clin Endocrinol Metab*, 81: 199-208 (1996); Orloff et al., *Endocrinology*, 131: 1603-1611 (1992).

PTHrP was originally identified by the inventor (Burtis et al., *J Biol Chem* 262: 7151-7156 (1987); Stewart et al., *Biochem Biophys Res Comm* 146: 672-678 (1987)) and others (Strewler et al., *J Clin Invest*, 80: 1803, (1987); Moseley et al., *Proc. Natl. Acad. Sci. USA*. 84: 5048-5052 (1987)) through its role as the causative agent for the common human paraneoplastic syndrome termed humoral hypercalcemia of malignancy (HHM). Stewart et al., *N Engl J Med* 303: 1377-1383 (1980). For example, humans with HIM may lose as much as 50% of their skeletal mass over a period of a few months, as a result of sustained elevations in circulating PTHrP. Stewart et al., *J Clin Endo Metab* 55: 219-227 (1982). Subsequent animal studies have indicated that PTHrP is capable of increasing bone mass in osteoporotic rats when administered intermittently. Surprisingly, however, the increases in bone mineral density, bone mass, bone formation, and skeletal biomechanics induced by PTHrP were not as dramatic as those observed using equimolar quantities of PTH. Stewart et al., *J Bone Min Res* 15: 1517-1525 (2000). Nonetheless, there anabolic and biomechanic-enhancing effects of PTHrP are surprising, since PTHrP is widely viewed as the quintessential catabolic skeletal hormone responsible for dramatic skeletal mineral losses in patients with HHM. Stewart et al., *J Clin Endo Metab* 55: 219-227 (1982). The observation that it is actually anabolic for the skeleton when administered intermittently was not anticipated, as evidenced by the fact that many investigators and pharmaceutical firms have worked for the past 10 years with PTH in osteoporosis, but none has embraced PTHrP despite its having been in the public domain since its initial description in 1987.

In 1999, Eli Lilly released a report to the FDA that indicated that daily administration of PTH to rats over a two-year period resulted in the development of osteogenic sarcomas in these rats. See, FDA notification to PTH IND holders, Dec. 11, 1998 (Neer et al., *N Engl J Med* 344: 1434-1441 (2001)). The development of these malignant skeletal tumors is extremely troubling to experts in the field, because the development of skeletal tumors derived from osteoblasts in this preclinical toxicity model was biologically plausible in causative terms, as being related to PTH. One key concern in the rat osteosarcoma story is that PTH was administered in the preclinical toxicity studies to growing rats for two years. This represents the large majority of the lifespan of the rat, also approximately two years. In humans, PTH treatment has generally had a duration of two to three years (Finkelstein et al., *N Engl J Med* 331: 1618-1623 (1994); Hodsman et al., *J Clin Endocrinol Metab* 82: 620-28 (1997); Lindsay et al., *Lancet* 350: 550-555 (1997); Neer et al., *N Engl J Med* 344: 1434-1441 (2001); Roe et al., Program and Abstracts of the 81st Annual Meeting of the Endocrine Society, p. 59 (1999); Lane et al., *J Clin Invest* 102: 1627-1633 (1998)). Most investigators anticipate that the duration of treatment with PTH will be from 18 months to 3 years. Therefore, a concern remains in the minds of some that long-term PTH treatment could result in osteosarcomas in humans.

Accordingly, a need remains in the art for a method for the prevention and treatment of bone disorders using skeletal anabolic drugs that is both safe and effective.

SUMMARY OF THE INVENTION

The present invention provides methods for the prevention and treatment of a variety of mammalian conditions manifested by loss of bone mass, including osteoporosis. The invention is based on the surprising observation that the administration of very high doses of a PTHrP, or a related analog, can produce drastic increases in BMD in a very short time period. The period of administration is preferably 15, 18, 21, 24, 30, or 36 months, more preferably 7, 8, 9, 10, 11, or 12 months, and most preferably 1, 2, 3, 4, 5, or 6 months. The high doses of the skeletal anabolic drug do not produce any adverse side effects when administered for short periods of time. Accordingly, the methods of the present invention offer greater safety by eliminating or reducing the risk of negative side effects commonly associated with skeletal anabolic drugs, such as hypercalcemia, renal failure, hypotension, or the risk of developing osteogenic sarcomas.

The rates of increase in BMD achieved with the methods of the present invention are extremely rapid. In one embodiment, three months of treatment with PTHrP-(1-36) yielded rates of increase in BMD that were greater than any rates previously obtained with anti-resorptives and lower doses of PTH for longer periods of administrations. The rates of increase in BMD achieved with the methods of the present invention are preferably at least 1% per month, 1.1% per month or 1.2% per month, more preferably 1.3% per month or 1.4% per month, and most preferably over 1.5% per month or 1.6% per month.

The increases in BMD observed are not generally obtained with anti-resorptives for two to three years of administrations. Indeed, several available anti-resorptives (SERMs, calcitonin, vitamin D, calcium) never achieve the increments in BMD obtained with the methods of the present invention. Moreover, the increments in BMD obtained with the methods of the present invention are comparable, or superior, to those achieved using lower doses of PTH for longer periods of administrations. Accordingly, the present invention provides methods for the prevention and treatment of bone disorders using skeletal anabolic drugs that are both safe and effective.

The resulting increase in BMD achieved with the methods of the present invention preferably results in T-scores >−2.5, more preferably results in T-scores >−2.0, and most preferably results in T-scores >−1.0. Furthermore, the resulting increase in BMD achieved with the methods of the present invention preferably prevents fractures resulting preferably in at least a 50%, 60%, or 70% reduction in incidence of fractures, more preferably in at least a 75%, 80%, or 85% reduction in incidence of fractures, and most preferably in at least a 90% or 95% reduction in incidence of fractures.

In one aspect, the present invention provides methods of increasing bone mass in an animal or a human patient by administering intermittently to the patient PTHrP, or an analog thereof, at a dosage between 50 and 3,000 µg/day. A preferred dose range is 400-3,000 µg/day. Other preferred dose ranges included 400-1,500 µg/day, 400-1,200 µg/day, 400-900 µg/day, 400-600 µg/day, 80-500 µg/day, 90-500 µg/day, 100-500 µg/day, 150-500 µg/day, 200-500 µg/day, 250-500 µg/day, 300-500 µg/day, 350-500 µg/day, 400-500 µg/day, and 450-500 µg/day. In a preferred embodiment, PTHrP-(1-36) is administered at a dosage between 50 and 3,000 µg/day. A preferred dose range is 400-3,000 µg/day. Other preferred dose ranges include 400-1,500 µg/day, 400-1,200 µg/day, 400-900 µg/day, and 400-600 µg/day (approximately 6.5-18 µg/kg/day, 6.5-15 µg/kg/day, 6.5-12 µg/kg/day, and 6.5-9 µg/kg/day).

The present invention also provides methods for increasing bone density using administration of PTHrP, or analogs thereof, for periods of time longer than previously administered in animals or humans. In one aspect, the present invention provides methods of increasing bone mass in an animal or a human patient by intermittently administering PTHrP, or an analog thereof, for a period of between 1-36 months. The period of administration is preferably 15, 18, 21, 24, 30, or 36 months, more preferably 7, 8, 9, 10, 11, or 12 months, and most preferably 1, 2, 3, 4, 5, or 6 months.

The methods of the invention can be employed with a patient afflicted with, or at risk of, a metabolic bone disorder including primary or secondary osteoporosis, osteomalacia, renal osteodystrophy, and other types of skeletal disorders with associated bone loss. In one embodiment, the rates of increase in BMD achieved by the methods of the present invention are at least 1.5% per month.

PTHrP, or an analog thereof, used in the methods of the present invention can be defined by SEQ ID NO:2; have at least 70% homology with SEQ ID NO:2; or be encoded by a nucleic acid sequence that hybridizes under stringent conditions to a complementary nucleic acid sequence of SEQ ID NO:1. PTHrP analogs that can be used in the methods of this invention include fragments PTHrP-(1-30) through PTHrP-(1-173). PTHrP analogs can also include analogs with a model amphipathic alpha-helical peptide (MAP) sequence substituted in the C-terminal region of hPTHrP(1-34) such as [MAP1-10]22-31 hPTHrP-(1-34) $NH_2$). PTHrP analogs can also include peptidomimetics and small molecule drugs having skeletal anabolic agonistic biological activities, as defined herein.

PTHrP can be administered by subcutaneous, oral, intravenous, intraperitoneal, intramuscular, buccal, rectal, vaginal, intranasal and aerosol administration. Intermittent administration may be by periodic injections once daily, once every two days, once every three days, once weekly, twice weekly, biweekly, twice monthly, and monthly. Alternatively, the use of pulsatile administration of the skeletal anabolic drug by mini-pump can be employed in the methods of the present invention.

In yet another aspect, the present invention provides methods of increasing bone mass in an animal or a human patient. In one embodiment, the method comprises administering between 1.5 and 90 mg of PTHrP, or an analog thereof, intermittently over a period of one month. In another embodiment, the method comprises administering between 3 and 180 mg of PTHrP, or an analog thereof, intermittently over a period of two months. In yet another embodiment, the method comprises administering between 4.5 and 270 mg of PTHrP, or an analog thereof, intermittently over a period of three months. In yet another embodiment, the method comprises administering between 9 and 540 mg of PTHrP, or an analog thereof, intermittently over a period of six months. In yet another embodiment, the method comprises administering between 18 and 1080 mg of PTHrP, or an analog thereof, intermittently over a period of one year. In yet another embodiment, the method comprises administering between 36 and 2160 mg of PTHrP, or an analog thereof, intermittently over a period of two years. In yet another embodiment, the method comprises administering between 54 and 3240 mg of PTHrP, or an analog thereof, intermittently over a period of three years. According to these methods, the PTHrP, or analog thereof, can be administered at a dosing interval of once daily, once every two days, once every three days, once-weekly, twice-weekly, biweekly, twice-monthly, or monthly.

In yet another aspect, the present invention provides kit for increasing bone mass in an animal or a human patient. In one embodiment, the kit comprises between 1.5 and 90 mg of MMP, or an analog thereof, and written directions providing instructions for intermittent administration of PTHrP, or an analog thereof, to an animal or a human patient over a period of one month. In another embodiment, the kit comprises between 3 and 180 mg of PTHrP, or an analog thereof, and written directions providing instructions for intermittent administration of PTHrP, or an analog thereof, to an animal or a human patient over a period of two months. In yet another embodiment, the kit comprises between 4.5 and 270 mg of PTHrP, or an analog thereof, written directions providing instructions for intermittent administration of PTHrP, or an analog thereof, to an animal or a human patient over a period of three months. In yet another embodiment, the kit comprises between 9 and 540 mg of PTHrP, or an analog thereof, written directions providing instructions for intermittent administration of PTHrP, or an analog thereof, to an animal or a human patient over a period of six months. In yet another embodiment, the kit comprises between 18 and 1080 mg of PTHrP, or an analog thereof, written directions providing instructions for intermittent administration of PTHrP, or an analog thereof, to an animal or a human patient over a period of one year. In yet another embodiment, the kit comprises between 36 and 2160 mg of PTHrP, or an analog thereof, written directions providing instructions for intermittent administration of PTHrP, or an analog thereof, to an animal or a human patient over a period of two years. In yet another embodiment, the kit comprises between 54 and 3240 mg of PTHrP, or an analog thereof, written directions providing instructions for intermittent administration of PTHrP, or an analog thereof, to an animal or a human patient over a period of three years.

The methods of the present invention can further comprise the step of co-administering, either simultaneously or sequentially with PTHrP, a bone resorption inhibiting agent. The bone resorption-inhibiting agent can be a bisphosphonate, estrogen, a selective estrogen receptor modulator, a selective androgen receptor modulator, calcitonin, a vitamin D analog, or a calcium salt. The bone resorption-inhibiting agent can also be alendronate, risedronate, etidronate, pamidronate, tiludronate, zoledronic acid, raloxifene, tamoxifene, droloxifene, toremifene, idoxifene, levonneloxifene, or conjugated estrogens. In one embodiment, the patient receives intermittent administration of the skeletal anabolic drug for a three-month period of time, followed by a three-month period of treatment with a bone resorption-inhibiting agent. A skilled artisan will recognized that the sequential treatment regimen could begin with a treatment period with a bone resorption inhibiting agent followed by a treatment period with the skeletal anabolic drug, that the length of sequential treatment periods can be modified (e.g., 1-18 months), and that the skeletal anabolic drug can be co-administered with the bone resorption inhibiting agent (e.g., sequential treatment period of a skeletal anabolic drug and a bone resorption inhibiting agent followed by a treatment period of a bone resorption inhibiting agent alone). The sequential treatment periods (e.g., three months of the skeletal anabolic drug followed by three month of the bone resorption inhibiting agent) can be repeated until the patient BMD is restored (e.g., a T-score <−2.0 or −2.5 below the mean).

In still another aspect, the invention includes a computer system and methods for the design of peptidomimetics and small molecule drugs having skeletal anabolic agonistic or antagonistic biological activities. In one embodiment, the system includes a processor, memory, a display or data output means, a data input means, and a computer readable instruction set having at least an algorithm capable of rendering a three-dimensional structure of a skeletal anabolic agent, fragment, or derivative thereof, as well as a receptor for such skeletal anabolic agent. In a more preferred embodiment, the system comprises a computer aided design (CAD) algorithm capable of rendering a peptidomimetic or small molecule drug based on the active sites of the skeletal anabolic agent or receptor.

These and other objects of the present invention will be apparent from the detailed description of the invention provided below.

BRIEF DESCRIPTION OF THE DRAWINGS

The present invention will be further understood from the following description with reference to the tables, in which:

FIG. 1 is a homology alignment of human PTHrP-(1-36) with the corresponding sequence in other species, aligned to maximize amino acid identity, and wherein amino acids that differ from the corresponding amino acid in the human sequence are bolded and amino acids that are conservative amino acid substitution variants of the corresponding amino acids in the human sequence are bolded and underlined.

FIG. 2 is a homology alignment of human PTH-(1-34) with the corresponding sequence in other species, aligned to maximize amino acid identity, and wherein amino acids that differ from the corresponding amino acid in the human sequence are bolded and amino acids that are conservative amino acid substitution variants of the corresponding amino acids in the human sequence are bolded and underlined.

FIG. 3 is a homology alignment of human TIP-(1-39) with the corresponding sequence in mouse, aligned to maximize amino acid identity, and wherein amino acids that differ from the corresponding amino acid in the human sequence are bolded and amino acids that are conservative amino acid substitution variants of the corresponding amino acids in the human sequence are bolded and underlined.

FIG. 6 illustrates bone turnover markers in the placebo and PTHrP-treated subjects.

FIG. 9 are line graphs depicting competition binding studies (Top Panels) of $^{125}$I-[Tyr$^{36}$]PTHrP-(1-36)NH$_2$ under equilibrium conditions to human renal cortical membranes (RCM) (Panel A), SaOS-2 membranes (Panel B), and SaOS-2 intact cells (Panel C). Competition curves are shown for unlabeled [Tyr$^{36}$]PTHrP-(1-36)NH$_2$ (Δ), hPTH-(1-34) (○), rPTH-(1-34) (▲), bPTH-(1-34) (●), [Try$^{34}$]bPTH-(7-34)NH$_2$ (■), and hPTHrP-(7-34)NH$_2$ (□). Values are the mean±SEM of replicate determinations for a representative experiment. Bottom Panels are line graphs depicting the corresponding Scatchard transformations of representative binding experiments.

FIG. 10 are line graphs depicting the stimulation of adenylate cylcase activity in human renal cortical membranes (RCM) (Panel A), SaOS-2 membranes (Panel B), and SaOS-2 intact cells (Panel C) by [Tyr$^{36}$]PTHrP-(1-36)NH$_2$ (Δ), [Nle$^{8,18}$,Tyr$^{34}$]hPTH-(1-34) (○), rPTH-(1-34) (▲), and bPTH-(1-34) (●). Assays were performed under the same conditions employed in the respective binding assays. Values are the mean±SEM of replicate determinations for a representative experiment.

FIG. 18 illustrates changes in serum calcium and renal calcium content during the six months. Note that rats treated with SDZ-PTH-893 developed moderate hypercalcemia, and marked increases in renal calcium content.

DETAILED DESCRIPTION OF THE INVENTION

A. General

Figure 4:
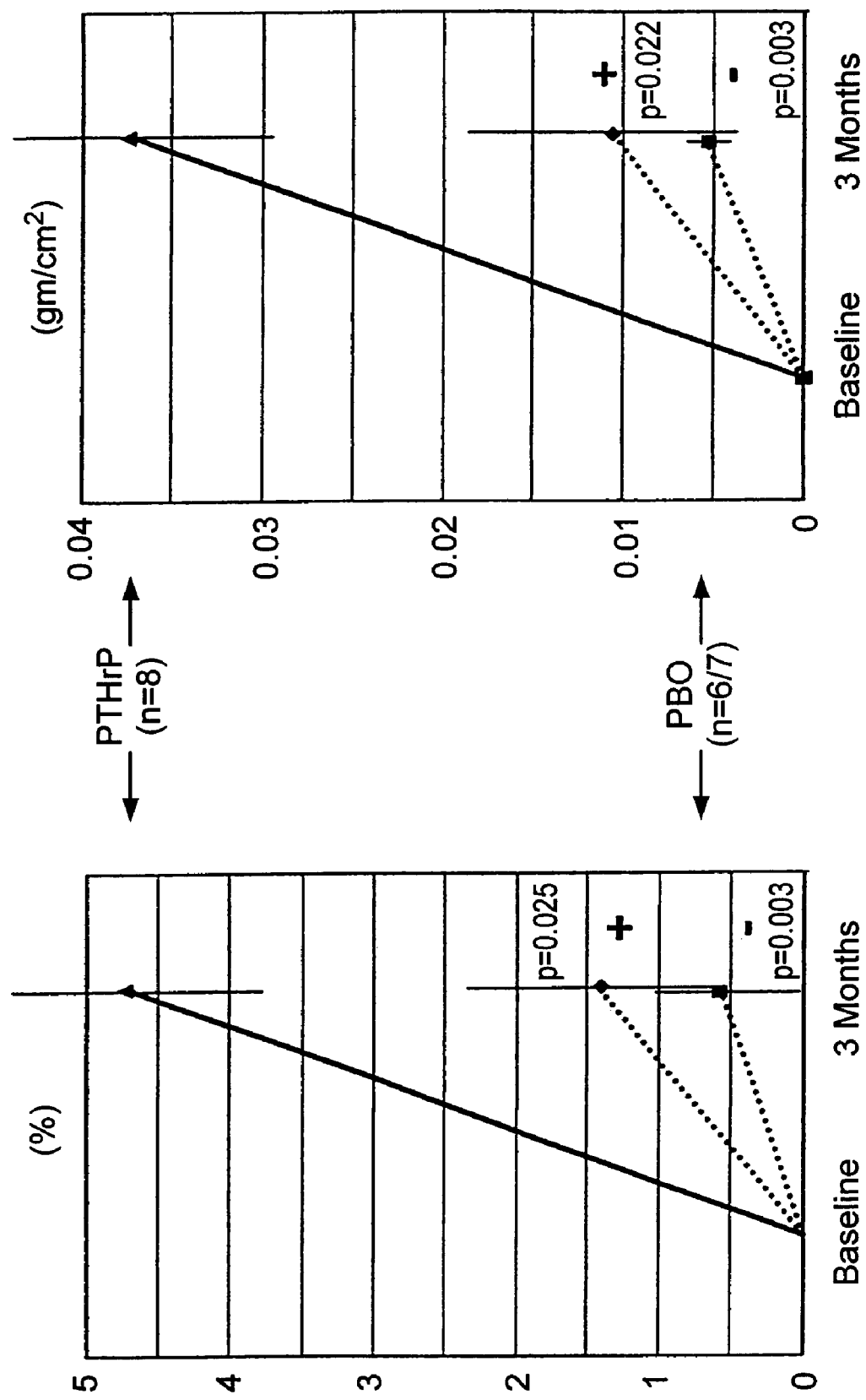
FIG. 4 is a line graph depicting the changes in lumbar vertebral bone mass density (BMD) expressed as % change (left panel) and weight (gram) change (right panel) in postmenopausal women with osteoporosis receiving placebo (N=7) or 410.25 μg/day of PTHrP-(1-36) (N=8).

Throughout adult life, bone is continually undergoing remodeling through the interactive cycles of bone formation and resorption (bone turnover). Bone resorption is typically rapid, and is mediated by osteoclasts (bone resorbing cells), formed by mononuclear phagocytic precursor cells at bone remodeling sites. This process then is followed by the appearance of osteoblasts (bone forming cells), which form bone slowly to replace the lost bone. The activities of the various cell types that participate in the remodeling process are controlled by interacting systemic (e.g., hormones, lymphokines, growth factors, vitamins) and local factors (e.g., cytokines, adhesion molecules, lymphokines and growth factors). The fact that completion of this process normally leads to balanced replacement and renewal of bone indicates that the molecular signals and events that influence bone remodeling are tightly controlled.

The mechanism of bone loss is not well understood but, in practical effect, the disorder arises from an imbalance in the formation of new healthy bone and the resorption of old bone, skewed toward a net loss of bone tissue. This bone loss includes a decrease in both mineral content and protein matrix components of the bone, and leads to an increased fracture rate of the femoral bones and bones in the forearm and vertebrae predominantly. These fractures, in turn, lead to an increase to general morbidity, a marked loss of stature and mobility, and in many cases, an increase in mortality resulting from complications.

A number of bone growth disorders are known which cause an imbalance in the bone remodeling cycle. Chief among these are metabolic bone diseases, such as osteoporosis, rickets, osteomalacia, chronic renal failure and hyperparathyroidism, which result in abnormal or excessive loss of bone mass (osteopenia). Other bone diseases, such as Paget's disease, also cause excessive loss of bone mass at localized sites.

Patients suffering from chronic renal (kidney) failure almost universally suffer loss of skeletal bone mass (renal osteodystrophy). While it is known that kidney malfunction causes a calcium and phosphate imbalance in the blood, to date replenishment of calcium and phosphate by dialysis does not significantly inhibit osteodystrophy in patients suffering from chronic renal failure. In adults, osteodystrophic symptoms often are a significant cause of morbidity. In children, renal failure often results in a failure to grow, due to the failure to maintain and/or to increase bone mass.

Rickets or Osteomalacia ("soft bones"), is a defect in bone mineralization (e.g., incomplete mineralization), and classically is related to vitamin D (1,25-dihydroxy vitamin $D_3$) deficiency or resistance. The defect can cause compression fractures in bone, and a decrease in bone mass, as well as extended zones of hypertrophy and proliferative cartilage in place of bone tissue. The deficiency may result from a nutritional deficiency (e.g., rickets in children), malabsorption of vitamin D or calcium, and/or impaired metabolism of the vitamin.

Hyperparathyroidism (overproduction of the parathyroid hormone) has been known to cause abnormal bone loss since its initial description in the 1920's. In children, hyperparathyroidism can inhibit growth. In adults with hyperparathyroidism, the skeleton integrity is compromised and fractures of the hip, vertebrae, and other sites are common. The parathyroid hormone imbalance typically may result from parathyroid adenomas or parathyroid gland hyperplasia. Secondary hyperparathyroidism may result from a number of disorders such as vitamin D deficiency or prolonged pharmacological use of a glucocorticoid such as cortisone. Secondary hyperparathyroidism and renal osteodystrophy may result from chronic renal failure. In the early stages of the disease, osteoclasts are stimulated to resorb bone in response to the excess hormone present. As the disease progresses, the trabecular and cortical bone may ultimately be resorbed and marrow is replaced with fibrosis, macrophages, and areas of hemorrhage as a consequence of microfractures. This condition, occurring in both primary and secondary hyperparathyroidism, is referred to pathologically as osteitis fibrosa cystica.

Osteoporosis is a structural deterioration of the skeleton caused by loss of bone mass resulting from an imbalance in bone formation, bone resorption, or both, such that the resorption dominates the bone formation phase, thereby reducing the weight-bearing capacity of the affected bone. Osteoporosis affects >10 million individuals in the United States, but only 10 to 20% are diagnosed and treated.

In a healthy adult, the rates at which bone is formed and resorbed are tightly coordinated so as to maintain the renewal of skeletal bone. However, in osteoporotic individuals, an imbalance in these bone-remodeling cycles develops which results in both loss of bone mass and in formation of microarchitectural defects in the continuity of the skeleton. These skeletal defects, created by perturbation in the remodeling sequence, accumulate and finally reach a point at which the structural integrity of the skeleton is severely compromised and bone fracture is likely. The chief clinical manifestations are vertebral and hip fractures, but all parts of skeleton may be affected. Osteoporosis is defined as a reduction of bone mass (or density) or the presence of a fragility fracture. This reduction in bone tissue is accompanied by deterioration in the architecture of the skeleton, leading to a markedly increased risk of fracture. Osteoporosis is defined operationally by the National Osteoporosis Foundation and World Health Organization as a bone density that falls −2.0 or −2.5 standard deviations (SD) below the mean (also referred to as a T-score of −2.0 or −2.5). Those who fall at the lower end of the young normal range (a T-score of >1 SD below the mean) have low bone density and are considered to be "osteopenic" and be at increased risk of osteoporosis.

Although this imbalance occurs gradually in most individuals as they age ("senile osteoporosis"), it is much more severe and occurs at a rapid rate in postmenopausal women. In addition, osteoporosis also may result from nutritional and endocrine imbalances, hereditary disorders and a number of malignant transformations.

Epidemiology

In the United States, as many as 8 million women and 2 million men have osteoporosis T-score <−2.5), and an additional 18 million individuals have bone mass levels that put them at increased risk of developing osteoporosis (e.g., bone mass T-score <−1.0). Osteoporosis occurs more frequently with increasing age, as bone tissue is progressively lost. In women, the loss of ovarian function at menopause (typically after age 50) precipitates rapid bone loss such that most women meet the criteria for osteoporosis by age 70.

The epidemiology of fractures follows similar trends as the loss of bone density. Fractures of the distal radius increase in frequency before age 50 and plateau by age 60, with only a modest age-related increase thereafter. In contrast, incidence rates for hip fractures double every five years after age 70. This distinct epidemiology may be related to the way people fall as they age, with fewer falls on an outstretched hand. At least 1.5 million fractures occur each year in the United States as a consequence of osteoporosis. As the population continues to age, the total number of fractures will continue to escalate.

Pathophysiology

Osteoporosis results from bone loss due to normal age-related changes in bone remodeling as well as extrinsic and intrinsic factors that exaggerate this process. These changes may be superimposed on a low peak bone mass. Consequently, the bone remodeling process is fundamental for understanding the pathophysiology of osteoporosis. The skeleton increases in size by linear growth and by apposition of new bone tissue on the outer surfaces of the cortex. This latter process is the phenomenon of remodeling, which also allows the long bones to adapt in shape to the stresses placed upon them. Increased sex hormone production at puberty is required for maximum skeletal maturation, which reaches maximum mass and density in early adulthood. Nutrition and lifestyle also play an important role in growth, though genetic factors are the major determinants of peak skeletal mass and density. Numerous genes control skeletal growth, peak bone mass, and body size, but it is likely that separate genes control skeletal structure and density. Heritability estimates of 50 to 80% for bone density and size have been derived based on twin studies. Though peak bone mass is often lower among individuals with a family history of osteoporosis, association studies of candidate genes [vitamin D receptor; Type I collagen, the estrogen receptor (ER), interleukin (IL) 6; and insulin-like growth factor (IGF) I] have not been consistently replicated. Linkage studies suggest that several genetic loci are associated with high bone mass.

Once peak skeletal mass has been attained, the process of remodeling remains the principal metabolic activity of the skeleton. This process has three primary functions: (1) to repair microdamage within the skeleton, (2) to maintain skeletal strength, and (3) to supply calcium from the skeleton to maintain serum calcium. Acute demands for calcium involve osteoclast-mediated resorption as well as calcium transport by osteocytes. The activation of remodeling may be induced by microdamage to bone due to excessive or accumulated stress.

Bone remodeling is also regulated by several circulating hormones, including estrogens, androgens, vitamin D, and PTH, as well as locally produced growth factors such as IGF-I and -II, transforming growth factor (TGF) β, PTHrP, ILs, prostaglandins, tumor necrosis factor (TNF), and osteoprotegrin and many others. Additional influences include nutrition (particularly calcium intake) and physical activity level. The end result of this remodeling process is that the resorbed bone is replaced by an equal amount of new bone tissue. Thus, the mass of the skeleton remains constant after peak bone mass is achieved in adulthood. After age 30 to 45, however, the resorption and formation processes become imbalanced, and resorption exceeds formation. This imbalance may begin at different ages and varies at different skeletal sites; it becomes exaggerated in women after menopause. Excessive bone loss can be due to an increase in osteoclastic activity and/or a decrease in osteoblastic activity. In addition, an increase in remodeling activation frequency can magnify the small imbalance seen at each remodeling unit.

Measurement of Bone Mass

Several noninvasive techniques are now available for estimating skeletal mass or density. These include dual-energy x-ray absorptiometry (DXA), single-energy x-ray absorptiometry (SXA), quantitative computed tomography (CT), and ultrasound.

DXA is a highly accurate x-ray technique that has become the standard for measuring bone density in most centers. Though it can be used for measurements of any skeletal site, clinical determinations are usually made of the lumbar spine and hip. Portable DXA machines have been developed that measure the heel (calcaneus), forearm (radius and ulna), or finger (phalanges), and DXA can also be used to measure body composition. In the DXA technique, two x-ray energies are used to estimate the area of mineralized tissue, and the mineral content is divided by the area, which partially corrects for body size. However, this correction is only partial since DXA is a two-dimensional scanning technique and cannot estimate the depths or posteroanterior length of the bone. Thus, small people tend to have lower-than-average bone mineral density (BMD). Newer DXA techniques that measure information BMD are currently under evaluation. Bone spurs, which are frequent in osteoarthritis, tend to falsely increase bone density of the spine. Because DXA instrumentation is provided by several different manufacturers, the output varies in absolute terms. Consequently, it has become standard practice to relate the results to "normal" values using T-scores, which compare individual results to those in a young population that is matched for race and gender. Alternatively, Z-scores compare individual results to those of an age-matched population that is also matched for race and gender. Thus, a 60-year-old woman with a Z-score of −1 (1 SD below mean for age) could have a T-score of −2.5 (2.5 SD below mean for a young control group).

CT is used primarily to measure the spine, and peripheral CT is used to measure bone in the forearm or tibia. Research into the use of CT for measurement of the hip is ongoing. CT has the added advantage of studying bone density in subtypes of bone, e.g., trabecular vs. cortical. The results obtained from CT are different from all others currently available since this technique specifically analyzes trabecular bone and can provide a true density (mass of bone per unit volume) measurement. However, CT remains expensive, involves greater radiation exposure, and is less reproducible.

Ultrasound is used to measure bone mass by calculating the attenuation of the signal as it passes through bone or the speed with which it traverses the bone. It is unclear whether ultrasound assesses bone quality, but this may be an advantage of the technique. Because of its relatively low cost and mobility, ultrasound is amenable for use as a screening procedure.

All of these techniques for measuring BMD have been approved by the U.S. Food and Drug Administration (FDA) based upon their capacity to predict fracture risk. The hip is the preferred site of measurement in most individuals, since it directly assesses bone mass at an important fracture site. When hip measurements are performed by DXA, the spine can be measured at the same time. In younger individuals, such as perimenopausal women, spine measurements may be the most sensitive indicator of bone loss.

B. Structural and Functional Properties of PTHrP Peptides.

Parathyroid hormone-related peptide (PTHrP), a 140+ amino acid protein, and fragments thereof, reproduce the major biological actions of PTH. PTHrP is elaborated by a number of human and animal tumors and other tissues and may play a role in hypercalcemia of malignancy. The nucleotide and amino acid sequences of hPTHrP-(1-36) are provided in SEQ ID NOS:1 and 2, respectively.

Biological activity is associated with the N-terminal portion. The amino acid sequence of the N-terminal segment of human PTHrP (hPTHrP) shows great homology with the N-terminal segment of various species, as illustrated in FIG. 1.

PTH and PTHrP, although distinctive products of different genes, exhibit considerable functional and structural homology and may have evolved from a shared ancestral gene. The structure of the gene for human PTHrP, however, is more complex than that of PTH, containing multiple exons and multiple sites for alternate splicing patterns during formation of the mRNA. Protein products of 141, 139, and 173 amino acids are produced, and other molecular forms may result from tissue-specific cleavage at accessible internal cleavage sites. The biologic roles of these various molecular species and the nature of the circulating forms of PTHrP are unclear. It is uncertain whether PTHrP circulates at any significant level in normal human adults; as a paracrine factor, PTHrP may be produced, act, and be destroyed locally within tissues. In adults PTHrP appears to have little influence on calcium homeostasis, except in disease states, when large tumors, especially of the squamous cell type, lead to massive overproduction of the hormone.

The sequence homology between hPTH and hPTHrP is largely limited to the 13 N-terminal residues, 8 of which are identical; only 1 of 10 amino acids in the (25-34) receptor-binding region of hPTH is conserved in hPTHrP. Conformational similarity may underlie the common activity. Cohen et al. (*J. Biol. Chem.* 266: 1997-2004 (1991)) have suggested that much of the sequence of PTH-(1-34) and PTHrP-(1-34), in particular regions (5-18) and (21-34), assumes an α-helical configuration, while noting that there is some question whether this configuration prevails for the carboxyl terminal end under physiological conditions. Such a secondary structure may be important for lipid interaction, receptor interaction, and/or structural stabilization.

The term "parathyroid hormone related protein" (PTHrP) encompasses naturally-occurring PTHrP, as well as synthetic or recombinant PTHrP (rec PTHrP). Further, the term "parathyroid hormone related protein" encompasses allelic variants, species variants, and conservative amino acid substitution variants. The term also encompasses full-length PTHrP-(1-36), as well as PTHrP fragments, including small peptidomimetic molecules having PTHrP-like bioactivity, for example, in the assays described herein. As with PTH, the biological activity of PTHrP is associated with the N-terminal portion, with residues (1-30) apparently the minimum required. It will thus be understood that fragments of PTHrP variants, in amounts giving equivalent biological activity to PTHrP-(1-36), can be used in the methods of the invention, if desired. Fragments of PTHrP incorporate at least the amino acid residues of PTHrP necessary for a biological activity similar to that of intact PTHrP-(1-36). Examples of such fragments include PTHrP-(1-30), PTHrP-(1-31), PTHrP-(1-32), PTHrP-(1-33), . . . PTHrP-(1-139), PTHrP-(1-140), and PTHrP-(1-141).

The term "parathyroid hormone-related protein" also encompasses variants and functional analogues of PTHrP having an homologous amino acid sequence with PTHrP-(1-36). The present invention thus includes pharmaceutical formulations comprising such PTHrP variants and functional analogs, carrying modifications like substitutions, deletions, insertions, inversions or cyclisations, but nevertheless having substantially the biological activities of parathyroid hormone. According to the present invention, "homologous amino acid sequence" means an amino acid sequence that differs from an amino acid sequence shown in SEQ ID NO:2, by one or more conservative amino acid substitutions, or by one or more non-conservative amino acid substitutions, deletions, or additions located at positions at which they do not destroy the biological activities of the polypeptide. Conservative amino acid substitutions typically include substitutions among amino acids of the same class. These classes include, for example, (a) amino acids having uncharged polar side chains, such as asparagine, glutamine, serine, threonine, and tyrosine; (b) amino acids having basic side chains, such as lysine, arginine, and histidine; (c) amino acids having acidic side chains, such as aspartic acid and glutamic acid; and (d) amino acids having nonpolar side chains, such as glycine, alanine, valine, leucine, isoleucine, proline, phenylalanine, methionine, tryptophan, and cysteine. Preferably, such a sequence is at least 75%, preferably 80%, more preferably 85%, more preferably 90%, and most preferably 95% homologous to the amino acid sequence in SEQ ID NO:2.

According to the present invention, homologous amino acid sequences include sequences that are identical or substantially identical to an amino acid sequence as shown in SEQ ID NO:2. By "amino acid sequence substantially identical" is meant a sequence that is at least 60%, preferably 70%, more preferably 80%, more preferably 90%, and most preferably 95% identical to an amino acid sequence of reference. Preferably the homologous sequence differs from the reference sequence, if at all, by a majority of conservative amino acid substitutions.

The calculation of % homology and % identity are determined by first aligning a candidate PTHrP polypeptide with SEQ ID NO:2, as provided in FIG. 1. Once aligned, the total number of identical amino acids and/or the number of conservative amino acid substitution variants shared between the candidate polypeptide and SEQ ID NO:2 are counted. For the calculation of % identity, the number of identical amino acids between the candidate PTHrP polypeptide and the reference sequence is divided by the total number of amino acids in the reference sequence, and this number is multiplied by 100 to obtain a percentage value. For the calculation of % homology, the total number of identical amino acids and conservative amino acid substitution variants between the candidate PTHrP polypeptide and the reference sequence is divided by the total number of amino acids in the reference sequence, and is multiplied by 100 to obtain a percentage value. FIG. 1 provides a homology alignment of human PTHrP-(1-36) (SEQ ID NO:2) with the corresponding sequence in other species, aligned to maximize amino acid identity. The amino acids in other species that differ from the corresponding amino acid in the human sequence are bolded and amino acids that are conservative amino acid substitution variants of the corresponding amino acids in the human sequence are bolded and underlined. The values of % identity and % homology are provided.

Alternatively, homology can be measured using sequence analysis software (e.g., Sequence Analysis Software Package of the Genetics Computer Group, University of Wisconsin Biotechnology Center, 1710 University Avenue, Madison, Wis. 53705). Similar amino acid sequences are aligned to obtain the maximum degree of homology (i.e., identity). To this end, it may be necessary to artificially introduce gaps into the sequence. Once the optimal alignment has been set up, the degree of homology (i.e., identity) is established by recording all of the positions in which the amino acids of both sequences are identical, relative to the total number of positions.

Similarity factors include similar size, shape and electrical charge. One particularly preferred method of determining amino acid similarities is the PAM25O matrix described in Dayhoff et al., 5 ATLAS OF PROTEIN SEQUENCE AND STRUCTURE 345-352 (1978 & Suppl.), incorporated by reference herein. A similarity score is first calculated as the sum of the aligned pairwise amino acid similarity scores. Insertions and deletions are ignored for the purposes of percent homology and identity. Accordingly, gap penalties are not used in this calculation. The raw score is then normalized by dividing it by the geometric mean of the scores of the candidate compound and the reference sequence. The geometric mean is the square root of the product of these scores. The normalized raw score is the percent homology.

Polypeptides having a sequence homologous to one of the sequences shown in SEQ ID NOS:1 or 2, include naturally-occurring allelic variants, as well as mutants and variants or any other non-naturally-occurring variants that are analogous in terms of bone formation activity, to a polypeptide having a sequence as shown in SEQ ID NO:2.

An allelic variant is an alternate form of a polypeptide that is characterized as having a substitution, deletion, or addition of one or more amino acids that does not substantially alter the biological function of the polypeptide. By "biological function" is meant the function of the polypeptide in the cells in which it naturally occurs, even if the function is not necessary for the growth or survival of the cells. For example, the biological function of a porin is to allow the entry into cells of compounds present in the extracellular medium. A polypeptide can have more than one biological function.

Allelic variants are very common in nature. Allelic variation may be equally reflected at the polynucleotide level. Polynucleotides, e.g., DNA molecules, encoding allelic variants can easily be retrieved by polymerase chain reaction (PCR) amplification of genomic DNA extracted by conventional methods. This involves the use of synthetic oligonucleotide primers matching upstream and downstream of the 5' and 3' ends of the encoding domain. Suitable primers can be designed according to the nucleotide sequence information provided in SEQ ID NO:1. Typically, a primer can consist of 10-40, preferably 15-25 nucleotides. It may be also advantageous to select primers containing C and G nucleotides in a proportion sufficient to ensure efficient hybridization; e.g., an amount of C and G nucleotides of at least 40%, preferably 50% of the total nucleotide amount.

Useful homologs that do not naturally occur can be designed using known methods for identifying regions of a PTHrP peptide that are likely to be tolerant of amino acid sequence changes and/or deletions. For example, stability-enhanced or modified variants of PTHrP are known in the art. For example, Vickery et al, (*J. Bone Miner. Res.*, 11: 1943-1951 (1996)) described a PTHrP analog with a model amphipathic alpha-helical peptide (MAP) sequence substituted in the C-terminal region of hPTHrP(1-34) and reported that the resulting analog, [MAP1-10]22-31 hPTHrP-(1-34) $NH_2$), had greater anabolic activity than the parent peptide in ovariectomized osteopenic rats. Other biologically active synthetic polypeptide analogs of PTH and PTHrP have been described in which amino acid residues (22-31) are substituted with hydrophilic amino acids and lipophilic amino acids forming an amphipathic α-helix. See, e.g., U.S. Pat. Nos. 5,589,452; 5,693,616; 5,695,955; 5,798,225; 5,807,823; 5,821,225; 5,840,837; 5,874,086; and 6,051,686, each of which is incorporated herein by reference. These homologs and other such biologically active peptidomimetic compounds are useful for creating small-molecule agonists or antagonists of PTHrP, PTH, or TIP peptides, as is discussed in Example 6.

Polypeptide derivatives that are encoded by polynucleotides of the invention include, e.g., fragments, polypeptides having large internal deletions derived from full-length polypeptides, and fusion proteins.

Polypeptide fragments of the invention can be derived from a polypeptide having a sequence homologous to any of the sequences shown in SEQ ID NOS:2-13, to the extent that the fragments retain the desired substantial bone formation properties of the parent polypeptide.

A polynucleotide of the invention, having a homologous coding sequence, can hybridize, preferably under stringent conditions, to a polynucleotide having a sequence complementary to the nucleotide sequence in SEQ ID NO:1. Hybridization procedures are described in, e.g., Ausubel et al., CURRENT PROTOCOLS IN MOLECULAR BIOLOGY, John Wiley & Sons Inc. (1994); Silhavy et al., EXPERIMENTS WITH GENE FUSIONS, Cold Spring Harbor Laboratory Press (1984); Davis et al., A MANUAL FOR GENETIC ENGINEERNG: ADVANCED BACTERIAL GENETICS, Cold Spring Harbor Laboratory Press (1980), each incorporated herein by reference. Important parameters that can be considered for optimizing hybridization conditions are reflected in a formula that allows calculation of a critical value, the melting temperature above which two complementary DNA strands separate from each other. Casey and Davidson, *Nucl. Acid Res.* 4: 1539 (1977). This formula is as follows:

$Tm=81.5+0.5\times(\% \ G+C)+1.6 \log(\text{positive ion concentration})-0.6\times(\% \ \text{formamide})$.

Under appropriate stringency conditions, hybridization temperature (Th) is approximately 20-40° C., 20-25° C. or, preferably, 30-40° C. below the calculated Tm. Those skilled in the art will understand that optimal temperature and salt conditions can be readily determined empirically in preliminary experiments using conventional procedures.

For example, stringent conditions can be achieved, both for pre-hybridizing and hybridizing incubations, (i) within 4-16 hours at 42° C., in 6×SSC containing 50% formamide or (ii) within 4-16 hours at 65° C. in an aqueous 6×SSC solution (1 M NaCl, 0.1 M sodium citrate (pH 7.0)).

For polynucleotides containing 30 to 600 nucleotides, the above formula is used and then is corrected by subtracting (600/polynucleotide size in base pairs). Stringency conditions are defined by a Th that is 5 to 10° C. below Tm.

Hybridization conditions with oligonucleotides shorter than 20-30 bases do not exactly follow the rules set forth above. In such cases, the formula for calculating the Tm is as follows:

$Tm=4\times(G+C)+2(A+T)$.

For example, an 18 nucleotide fragment of 50% G+C would have an approximate Tm of 54° C.

Consequently, the methods of the present invention includes the use of a PTHrP peptide selected from the group consisting of:
  (a) full-length PTHrP;
  (b) biologically-active variants of full-length PTHrP;
  (c) biologically active PTHrP fragments;
  (d) biologically active variants of PTHrP fragments;
  (e) biologically active variants having at least 75% homology with SEQ ID NO:2;
  (f) biologically active variants having at least 60% identity with SEQ ID NO:2; and
  (g) biologically active variants encoded by a nucleic acid sequence that hybridizes under stringent conditions to a complementary nucleic acid sequence of SEQ ID NO:1.

PTHrP includes, but is not limited to, human PTHrP (hPTHrP), bovine PTHrP (bPTHrP), and rat PTHrP (rPTHrP). An analog of PTHrP is a peptide which is a structural analog or fragment (preferably, an N-terminal fragment containing 50 or fewer amino acids) of a naturally-occurring PTHrP and, like PTHrP, also capable of binding to PTH receptor and stimulating adenylate cyclase activity, thereby promoting bone formation. Examples of such fragments include, but are not limited to, PTHrP-(1-30), PTHrP-(1-31), PTHrP-(1-32), PTHrP-(1-33), . . . PTHrP-(1-139), PTHrP-(1-140), and PTHrP-(1-141). The following publications disclose the sequences of P peptides: Yasuda et al., *J. Biol. Chem.* 264: 7720-7725 (1989); Schermer, *J. Bone & Min. Res.* 6: 149-155 (1991); and Burtis, *Clin. Chem.* 38: 2171-2183 (1992). More examples can be found in the following publications: German Application 4203040 A1 (1993); PCT Application 94/01460 (1994); PCT Application 94/02510 (1994); EP Application 477885 A2(1992); EP Application 561412 A1 (1993); PCT Application 93/20203 (1993); U.S. Pat. No. 4,771,124 (1988); PCT Application 92/11286 (1992); PCT Application 93/06846 (1993); PCT Application 92/10515 (1992); U.S. Pat. No. 4,656,250 (1987); EP Application 293158 A2 (1988); PCT Application 94/03201 (1994); EP Application 451,867 A1 (1991); U.S. Pat. No. 5,229,489 (1993); and PCT Application 92/00753 (1992).

PTHrP exerts important developmental influences on fetal bone development and in adult physiology. A homozygous knockout of the PTHrP gene (or the gene for the PTH receptor) in mice causes a lethal deformity in which animals are born with severe skeletal deformities resembling chondrodysplasia.

Many different cell types produce PTHrP, including brain, pancreas, heart, lung, mammary tissue, placenta, endothelial cells, and smooth muscle. In fetal animals, PTHrP directs transplacental calcium transfer, and high concentrations of PTHrP are produced in mammary tissue and secreted into milk. Human and bovine milk, for example, contain very high concentrations of the hormone; the biologic significance of the latter is unknown. PTHrP may also play a role in uterine contraction and other biologic functions, still being clarified in other tissue sites.

PTHrP Biological Actions

Because PTHrP shares a significant homology with PTH in the critical amino terminus, it binds to and activates the PTH/PTHrP receptor, with effects very similar to those seen with PTH. However, PTHrP, not PTH, appears to be the predominant physiologic regulator of bone mass, with PTHrP being essential for the development of full bone mass. Demonstrating this, conditional gene knockout strategies, employing mice in which the PTHrP gene was disrupted in osteoblasts prevented the production of PTHrP locally within adult bone, but which had normal PTH levels in adult bone. Absent PTHrP, and these mice developed osteoporosis demonstrating that osteoblast-derived PTHrP exerts anabolic effects in bone by promoting osteoblast function. See, Karaplis, A. C. "Conditional Knockout of PTHrP in Osteoblasts Leads to Premature Osteoporosis." Abstract 1052, Annual Meeting of the American Society for Bone and Mineral Research, September 2002, San Antonio, Tex. *J Bone Mineral Res, Vol* 17 (Suppl 1), pp S138, 2002, incorporated by reference. These findings indicate that PTHrP, and not PTH, is the more important normal regulator of bone mass under normal physiologic conditions, and that PTH treatment for osteoporosis, while effective, serves only as a surrogate for PTHrP, the authentic bone mass regulator.

The 500-amino-acid PTH/PTHrP receptor (also known as the PTH1 receptor) belongs to a subfamily of GCPR that includes those for glucagon, secretin, and vasoactive intestinal peptide. The extracellular regions are involved in hormone binding, and the intracellular domains, after hormone activation, bind G protein subunits to transduce hormone signaling into cellular responses through stimulation of second messengers.

A second PTH receptor (PTH2 receptor) is expressed in brain, pancreas, and several other tissues. Its amino acid sequence and the pattern of its binding and stimulatory response to PTH and PTHrP differ from those of the PTH1 receptor. The PTH/PTHrP receptor responds equivalently to PTH and PTHrP, whereas the PTH2 receptor responds only to PTH. The endogenous ligand of this receptor appears to be tubular infundibular peptide-39 or TIP-39. The physiological significance of the PTH2 receptor-TIP-39 system remains to be defined. Recently, a 39-amino-acid hypothalamic peptide, tubular infundibular peptide (TIP-39), has been characterized and is a likely natural ligand of the PTH2 receptor.

The PTH1 and PTH2 receptors can be traced backward in evolutionary time to fish. The zebrafish PTH1 and PTH2 receptors exhibit the same selective responses to PTH and PTHrP as do the human PTH1 and PTH2 receptors. The evolutionary conservation of structure and function suggests unique biologic roles for these receptors.

G proteins of the $G_s$ class link the PTH/PTHrP receptor to adenylate cyclase, an enzyme that generates cyclic AMP, leading to activation of protein kinase A. Coupling to G proteins of the $G_q$ class links hormone action to phospholipase C, an enzyme that generates inositol phosphates (e.g., $IP_3$) and DAG, leading to activation of protein kinase C and intracellular calcium release. Studies using the cloned PTH/P receptor confirm that it can be coupled to more than one G protein and second-messenger kinase pathway, apparently explaining the multiplicity of pathways stimulated by PTH and PTHrP. Incompletely characterized second-messenger responses (e.g., MAP kinase activation) may be independent of phospholipase C or adenylate cyclase stimulation (the latter, however, is the strongest and best characterized second messenger signaling pathway for PTH and PTHrP).

The details of the biochemical steps by which an increased intracellular concentration of cyclic AMP, $IP_3$, DAG, and intracellular $Ca^{2+}$ lead to ultimate changes in ECF calcium and phosphate ion translocation or bone cell function are unknown. Stimulation of protein kinases (A and C) and intracellular calcium transport is associated with a variety of hormone-specific tissue responses. These responses include inhibition of phosphate and bicarbonate transport, stimulation of calcium transport, and activation of renal 1α-hydroxylase in the kidney. The responses in bone include effects on collagen synthesis; increased alkaline phosphatase, ornithine decarboxylase, citrate decarboxylase, and glucose-6-phosphate dehydrogenase activities; DNA, protein, and phospholipid synthesis; calcium and phosphate transport; and local cytokine/growth factor release. Ultimately, these biochemical events lead to an integrated hormonal response in bone turnover and calcium homeostasis.

C. Other Anabolic Agents

Other agents provide anabolic effects, similar to those demonstrated by PTHrP, for example, PTH, and TIP. Compositions of PTH and TIP, and their uses, are similar to those for PTHrP disclosed herein. These skeletal anabolic agents, PTH and TIP, or analogs thereof, increase bone mass in a human patient in need thereof, when administered to said patient at a dosage between 10 and 3,000 µg/day for a period of 1-36 months. In alternative embodiments, the dosage is preferably 50-1,000 µg/day, more preferably 50-500 µg/day. In yet other alternative embodiments, the period of administration is preferably 12, 15, or 18 months, more preferably 7, 8, 9, 10, or 11 months, and most preferably 1, 2, 3, 4, 5, or 6 months. The increase in bone mass can be monitored by the assays described herein. These skeletal anabolic agents can be combined with PTHrP. They are described below.

PTH Peptides

PTH is an 84 amino-acid single-chain peptide. The amino acid sequence of PTH has been characterized in multiple mammalian species, revealing marked conservation in the amino-terminal portion, which is critical for many biologic actions of the molecule. Biological activity is associated with the N-terminal portion, with residues (1-29) apparently the minimum required. The N-terminal segment of human PTH (hPTH) differs from the N-terminal segment of the bovine (bPTH) and porcine (pPTH) hormones by only three and two amino acid residues, respectively.

PTH is initially synthesized as a larger molecule (preproparathyroid hormone, consisting of 115 amino acids), which is then reduced in size by signal peptide cleavage (proparathyroid hormone, 90 amino acids) and then a second prohormone cleavage before secretion as an 84 amino acid peptide. The hydrophobic regions of the preproparathyroid hormone serve a role in guiding transport of the polypeptide from sites of synthesis on polyribosomes through the endoplasmic reticulum to secretory granules.

Modified, substituted synthetic fragments of the amino-terminal sequence as small as 1-14 residues are sufficient to activate the major receptor. Biologic roles for the carboxyl-terminal region of PTH (e.g., 35-84) are under investigation; a separate receptor or receptors may exist for this region of the molecule. Fragments shortened or modified at the amino terminus still bind to the PTH receptor but lose the capacity to stimulate biologic responses. For example, the peptide composed of the sequence 7-34 is a competitive inhibitor of active hormone binding to receptors in vitro but is a weak inhibitor in vivo.

The term "parathyroid hormone" (PTH) encompasses naturally occurring PTH, as well as synthetic or recombinant PTH (rec PTH). Further, the term "parathyroid hormone" encompasses allelic variants, species variants, and conservative amino acid substitution variants. The term also encompasses full-length PTH-(1-84), as well as PTH fragments. It will thus be understood that fragments of PTH variants, in amounts giving equivalent biological activity to PTH-(1-84), can be used in the methods of the invention, if desired. Fragments of PTH incorporate at least the amino acid residues of PTH necessary for a biological activity similar to that of intact PTH. Examples of such fragments include: PTH-(1-29), PTH-(1-30), PTH-(1-31), PTH-(1-32), PTH-(1-33), PTH-(1-34), PTH-(1-80), PTH-(1-81), PTH-(1-82), PTH-(1-83), and PTH-(1-84).

The term "parathyroid hormone" also encompasses variants and functional analogs of PTH having a homologous amino acid sequence with PTH-(1-34). The present invention thus includes pharmaceutical formulations comprising such PTH variants and functional analogs, carrying modifications like substitutions, deletions, insertions, inversions or cyclisations, but nevertheless having substantially the biological activities of parathyroid hormone. Stability-enhanced variants of PTH are known in the art from, e.g., WO 92/11286 and WO 93/20203, each incorporated herein by reference. Variants of PTH can incorporate, for example, amino acid substitutions that improve PTH stability and half-life, such as the replacement of methionine residues at positions 8 and/or 18, and replacement of asparagine at position 16. Cyclized PTH analogs are disclosed in, e.g., WO 98/05683, incorporated herein by reference. The term "parathyroid hormone" also encompasses amino acid substituted analogs using the PT-(1-11) or PTH-(1-14) backbone. Shimizu et al., *J Biol Chem.*, 276: 49003-49012 (2001); Shimizu et al., *Endocrinology* 42: 3068-3074 (2001); Carter and Gardella, *Biochim Biophys Acta* 1538: 290-304 (2001); Shimizu et al., *J Biol Chem.*, 275: 21836-21843 (2000), each incorporated herein by reference.

FIG. 2 provides a homology alignment of the reference sequence, human PTH-(1-34) (SEQ ID NO: 15), with the corresponding sequence in other species, aligned to maximize amino acid identity. "Homologous amino acid sequence" means an amino acid sequence that differs from an amino acid sequence shown in SEQ ID NO: 15, by one or more conservative amino acid substitutions, or by one or more non-conservative amino acid substitutions, deletions, or additions located at positions at which they do not destroy the biological activities of the polypeptide. Preferably, such a sequence is at least 75%, preferably 80%, more preferably 85%, more preferably 90%, and most preferably 95% homologous to the amino acid sequence in SEQ ID NO: 2. Homologous amino acid sequences also include sequences that are identical or substantially identical to an amino acid sequence as shown in SEQ ID NO: 15. By "amino acid sequence substantially identical" is meant a sequence that is at least 60%, preferably 70%, more preferably 80%, more preferably 90%, and most preferably 95% identical to an amino acid sequence of reference. Preferably the homologous sequence differs from the reference sequence, if at all, by a majority of conservative amino acid substitutions.

PTH peptides useful in the methods of the present invention include the use of a PTH peptide selected from the group consisting of:
(a) full-length parathyroid hormone;
(b) biologically active variants of full-length parathyroid hormone;
(c) biologically active parathyroid hormone fragments;
(d) biologically active variants of parathyroid hormone fragments;
(e) biologically active variants having at least 75% homology with SEQ ID NO:15;
(f) biologically active variants having at least 60% identity with SEQ ID NO:15; and
(g) biologically active variants encoded by a nucleic acid sequence that hybridizes under stringent conditions to a complementary nucleic acid sequence of SEQ ID NO:14.

TIP Peptides

Recently, a 39-amino-acid hypothalamic peptide, tubular infundibular peptide (TIP-39), has been characterized and is a likely natural ligand of the PTH2 receptor. Accordingly, TIP-39, and biologically-active fragments and analogs thereof, can be used in the methods of the present invention.

The term "tubular infundibular peptide" encompasses naturally-occurring TIP, as well as synthetic or recombinant TIP (rec TIP). Further, the term "tubular infundibular peptide" encompasses allelic variants, species variants, and conservative amino acid substitution variants. The term also encompasses full-length TIP-(1-39), as well as TIP fragments. It will thus be understood that fragments of TIP variants, in amounts giving equivalent biological activity to TIP-(1-39), can be used in the methods of the invention, if desired. Fragments of TIP incorporate at least the amino acid residues of TIP necessary for a biological activity similar to that of intact TIP-(1-39). Examples of such fragments are TIP-(1-29), TIP-(1-30), TIP-(1-31), . . . TIP-(1-37), TIP-(1-38), and TIP-(1-39).

The term "tubular infundibular peptide" also encompasses variants and functional analogues of TIP having an homologous amino acid sequence with TIP-(1-39). The present invention thus includes pharmaceutical formulations comprising such TIP variants and functional analogs, carrying modifications like substitutions, deletions, insertions, inversions or cyclisations, but nevertheless having substantially the biological activities of TIP-(1-39).

The calculation of % homology and % identity are determined by first aligning a candidate TIP polypeptide with SEQ ID NO:26, as provided in FIG. 3. "Homologous amino acid sequence" means an amino acid sequence that differs from an amino acid sequence shown in SEQ ID NO: 15, by one or more conservative amino acid substitutions, or by one or more non-conservative amino acid substitutions, deletions, or additions located at positions at which they do not destroy the biological activities of the polypeptide. Preferably, such a sequence is at least 75%, preferably 80%, more preferably 85%, more preferably 90%, and most preferably 95% homologous to the amino acid sequence in SEQ ID NO: 26. Homologous amino acid sequences also include sequences that are identical or substantially identical to an amino acid sequence as shown in SEQ ID NO: 26. By "amino acid sequence substantially identical" is meant a sequence that is at least 60%, preferably 70%, more preferably 80%, more preferably 90%, and most preferably 95% identical to an amino acid sequence of reference. Preferably the homologous sequence differs from the reference sequence, if at all, by a majority of conservative amino acid substitutions.

The methods of the present invention includes the use of a TIP peptide selected from the group consisting of:
(a) full-length TIP;
(b) biologically-active variants of full-length TIP;
(c) biologically active TIP fragments;
(d) biologically active variants of TIP fragments;
(e) biologically active variants having at least 75% homology with SEQ ID NO:26;
(f) biologically active variants having at least 60% identity with SEQ ID NO:26; and
(g) biologically active variants encoded by a nucleic acid sequence that hybridizes under stringent conditions to a complementary nucleic acid sequence of SEQ ID NO:25.

D. Formulations and Methods of Treatment

Compositions of the present invention (i.e., PTHrP peptide, and the skeletal anabolic agents described above) may be administered intermittently by any route which is compatible with the particular molecules and, when included, with the particular bone resorption inhibiting agent. Thus, as appropriate, administration may be oral or parenteral, including subcutaneous, intravenous, inhalation, nasal, and intraperitoneal routes of administration. In addition, intermittent administration may be by periodic injections of a bolus of the composition once daily, once every two days, once every three days, once weekly, twice weekly, biweekly, twice monthly, and monthly Therapeutic compositions of the present invention may be provided to an individual by any suitable means, directly (e.g., locally, as by injection, implantation or topical administration to a tissue locus) or systemically (e.g., parenterally or orally). Where the composition is to be provided parenterally, such as by intravenous, subcutaneous, intramolecular, ophthalmic, intraperitoneal, intramuscular, buccal, rectal, vaginal, intraorbital, intracerebral, intracranial, intraspinal, intraventricular, intrathecal, intracisternal, intracapsular, intranasal or by aerosol administration, the composition preferably comprises part of an aqueous or physiologically compatible fluid suspension or solution. Thus, the carrier or vehicle is physiologically acceptable so that in addition to delivery of the desired composition to the patient, it does not otherwise adversely affect the patient's electrolyte and/or volume balance. The fluid-medium for the agent thus can comprise normal physiologic saline (e.g., 0.9% aqueous NaCl, 0.15 M, pH 7-7.4). Alternatively, the use of pulsatile administration of the skeletal anabolic drug by mini-pump can be employed in the methods of the present invention.

Useful solutions for parenteral administration may be prepared by any of the methods well known in the pharmaceutical art, described, for example, in REMNGTON'S PHARMACEUCAL SCIENCES (Gennaro, A., ed.), Mack Pub., 1990. Formulations of the therapeutic agents of the invention may include, for example, polyalkylene glycols such as polyethylene glycol, oils of vegetable origin, hydrogenated naphthalenes, and the like. Formulations for direct administration, in particular, may include glycerol and other compositions of high viscosity to help maintain the agent at the desired locus. Biocompatible, preferably bioresorbable, polymers, including, for example, hyaluronic acid, collagen, tricalcium phosphate, polybutyrate, lactide, and glycolide polymers and lactideiglycolide copolymers, may be useful excipients to control the release of the agent in vivo. Other potentially useful parenteral delivery systems for these agents include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, methoxysalicylate for rectal administration, or cutric acid for vaginal administration. Suppositories for rectal administration may also be prepared by mixing the PTHrP peptide (alone or in combination with a bone resorption-inhibiting agent) with a non-irritating excipient such as cocoa butter or other compositions that are solid at room temperature and liquid at body temperatures.

Formulations for topical administration to the skin surface may be prepared by dispersing the molecule capable of releasing the PTHrP peptide (alone or in combination with a bone resorption-inhibiting agent, or an anabolic agent) with a dermatologically acceptable carrier such as a lotion, cream, ointment or soap. Particularly useful are carriers capable of forming a film or layer over the skin to localize application and inhibit removal. For topical, administration to internal tissue surfaces, the agent may be dispersed in a liquid tissue adhesive or other substance known to enhance adsorption to a tissue surface. For example, hydroxypropylcellulose or fibrinogen/thrombin solutions may be used to advantage. Alternatively, tissue-coating solutions, such as pectin-containing formulations may be used.

The method of treatment can constitute a single period of intermittent administration of a skeletal anabolic drug (e.g., for a period of time varying between 1-3 months to 15-18 months). The period of administration is preferably 12, 15, or 18 months, more preferably 7, 8, 9, 10, or 11 months, and most preferably 1, 2, 3, 4, 5, or 6 months. Alternatively, in another embodiment, the method of treatment can constitute a series of administration periods followed by periods of no administration (e.g., sequential periods of three months of intermittent administration of a skeletal anabolic drug and three months of no drug administration). The sequential treatment periods can be repeated until the patient BMD is restored (e.g., a T-score <−2.0 or −2.5 below the mean or preferably <−1.0 below the mean).

In yet another embodiment, the method of treatment further includes the step of co-administering, either simultaneously or sequentially to said patient a bone resorption inhibiting agent. The bone resorption-inhibiting agent can be a bisphosphonate, estrogen, a selective estrogen receptor modulator, a selective androgen receptor modulator, calcitonin, a vitamin D analog, or a calcium salt. The bone resorption-inhibiting agent can also be alendronate, risedronate, etidronate, pamidronate, tiludronate, zoledronic acid, raloxifene, tamoxifene, droloxifene, toremifene, idoxifene, levormeloxifene, or conjugated estrogens. In one embodiment, the patient receives intermittent administration of the skeletal anabolic drug for a period of time, followed by a period of treatment with a bone resorption inhibiting agent, either alone or in combination with the skeletal anabolic drug. In a currently preferred embodiment, an anabolic agent such as PTHrP is first administered, for example, over a three month period or longer, followed by administration of an antiresorptive agent either alone or in combination with the skeletal anabolic drug, for example, over an additional three month period or longer. Without being restricted to theory, reverse administration, i.e., giving the antiresorptive agent before administration of the anabolic agent, diminishes the efficacy of the anabolic agent. Hence, according to the present invention, anabolic agents such as PTHrP should be the primary osteoporosis therapeutics, with antiresorptives used later to maintain and enhance the PTHrP/PTH/TIP effects, and for example, estrogen or bisphosphonates osteoporosis administered as second line agents after the anabolics.

However, a skilled artisan will recognized that the sequential treatment regimen could begin with a treatment period with a bone resorption inhibiting agent followed by a treatment period with the skeletal anabolic drug, that the length of sequential treatment periods can be modified (e.g., 1-18 months), and that the skeletal anabolic drug can be co-administered with the bone resorption inhibiting agent (e.g., sequential treatment period of a skeletal anabolic drug and a bone resorption inhibiting agent followed by a treatment period of a bone resorption inhibiting agent alone). Again, as stated above, the sequential treatment periods (e.g., three months of the skeletal anabolic drug followed by three month of the bone resorption inhibiting agent) can be repeated until the patient BMD is restored (e.g., a T-score <−2.0 or −2.5 below the mean or preferably <−1.0 below the mean).

Skeletal anabolic agents are commonly believed to demonstrate numerous adverse side effects, and as a result, the dosage and administration of these agents is carefully controlled, and the patient carefully monitored for emergence of unwanted side effects. For example, PTHrP was originally thought to be responsible for most instances of hypercalcemia of malignancy, a syndrome that resembles hyperparathyroidism, with a toxicity profile believed to be similar to or even greater to that of PTH.

However, the toxicity profiles of other skeletal anabolic agents do not appear to be applicable to PTHrP. The findings of the present invention indicate that despite being administered in doses, for example, at least 20 times higher than those considered safe for PTH, PTHrP does not cause significant side effects. For example, intermittent doses of PTHrP of about 50 micrograms to about 400 micrograms given subcutaneously (Q2H for 8 hours after a dose), does not appear to cause hypercalcemia. In fact, administration of PTHrP has never been observed to cause hypercalcemia at any dose yet given, such as doses exceeding 450 micrograms. Therapeutic doses up to 1 milligram are safe and efficacious, and in certain cases, doses of 3 milligrams or greater are also possible given proper patient monitoring.

Specifically, there have been no examples of the development of hypercalcemia (defined in the studies described in Example 1 and Example 5 as a serum calcium above 9.9 mg/dl, a very conservative definition of hypercalcemia) in 18 PTHrP-treated patients despite the comparatively higher doses employed. This contrasts with the Neer, et al. study demonstrating an 11% incidence of hypercalcemia reported among patients treated with PTH at the 20 microgram dose and a 28% incidence of hypercalcemia reported among patients who received the 40 microgram dose. Interestingly, Neer, et al. defined hypercalcemia as a serum calcium greater than 10.6 mg/dl. Recalculation of the results of the Neer, et al study using the more rigorous 9.9 mg/dl criteria for hypercalcemia described herein, would have resulted in a much higher hypercalcemia incidence in the Neer, et al. study. Other researchers have seen even more severe hypercalcemia, up to 15 mg/dl, which is near lethal, using PTH(1-84) at doses of approximately 40 micrograms.

Thus, PTHrP offers many advantages over PTH as a therapeutic. It is a pure anabolic skeletal agent which is non-hypercalcemic, and has no other adverse effects even when administered in the comparatively higher doses explored to date. Second it appears far more efficacious than PTH in increasing bone mass density. Third, it is more stable than PTH. Fourth, it has markedly different and more favorable pharmacokinetics than PTH. Fifth, it is responsible for maintaining bone mass in adults, in contrast to PTH, which is not required to maintain bone mass. Sixth, it can achieve therapeutic endpoints in shorter time-frames, and is thereby safer for human administration, for example use for only 3-9 months can achieve dramatic effects on BMD without crossing the 12-month osteosarcoma threshold.

E. Bioassay of Anabolic Efficacy of PTHrP Analogs

The synthesis, selection and use of PTHrP or analogs thereof and other anabolic agents, which are capable of promoting bone formation, are within the ability of a person of ordinary skill in the art. For example, well-known in vitro or in vivo assays can be used to determine the efficacy of various candidate PTHrP analogs to promote bone formation in human patients. For in vitro binding assays, osteoblast-like cells which are permanent cell lines with osteoblastic characteristics and possess receptors for PTHrP of either rat or human origin can be used. Suitable osteoblast-like cells include ROS 17/2 (Jouishomme et al., *Endocrinology*, 130: 53-60 (1992)), UMR 106 (Fujimori et al., *Endocrinology*, 130: 29-60 (1992)), and the human derived SaOS-2 (Fukuyama et al., *Endocrinology*, 131: 1757-1769 (1992)). The cell lines are available from American Type Culture Collection, Rockville, Md., and can be maintained in standard specified growth media. Additionally, transfected human embryonic kidney cells (HEK 293) expressing the human PTH1 or PTH2 receptors can also be utilized for in vitro binding assays. See, Pines et al., *Endocrinology*, 135: 1713-1716 (1994).

For in vitro functional assays, PTHrP-like analog activities of peptide fragments or derivatives of PTHrP can be tested by contacting a concentration range of the test compound with the cells in culture and assessing the stimulation of the activation of second messenger molecules coupled to the receptors, e.g., the stimulation of cyclic AMP accumulation in the cell or an increase in enzymatic activity of protein kinase C, both of which are readily monitored by conventional assays. See, Jouishomme et al., *Endocrinology*, 130: 53-60 (1992); Abou-Samra et al., *Endocrinology*, 125: 2594-2599 (1989); Fujimori et al., *Endocrinology*, 128: 3032-3039 (1991); Fukayama et al., *Endocrinology*, 134: 1851-1858 (1994); Abou-Samra et al., *Endocrinology*, 129: 2547-2554 (1991); and Pines et al., *Endocrinology*, 135: 1713-1716 (1994). Other parameters of PTH action include increase in cytosolic calcium and phosphoinositols, and biosynthesis of collagen, osteocalcin, and alteration in alkaline phosphatase activity.

Agonist activities of subfragments of PTH have been successfully analyzed by contacting peptides with rat kidney cells in culture and assessing cyclic AMP accumulation (Blind et al., *Clin. Endocrinol.*, 101: 150-155 (1993)) and the stimulation of 1,25-dehydroxyvitamin $D_3$ production (Janulis et al., *Endocrinology*, 133: 713-719 (1993)).

As demonstrated in Examples 2 and 3 below, PTH and PTHrP with bone formation activity bind specifically with PTH/PTHrP receptors and produce a dose-dependent stimulation of cAMP accumulation in human renal cortical membranes, in human osteoblast-like osteosarcoma membranes and intact cells (Example 2), and in canine renal cortical membranes (Example 3). With $[Nle^{8,18},Tyr^{34}]$ hPTH-(1-34) $NH_2$ or hPTHrP-(1-36) as the reference standard analogs, a dose-response relationship can be generated using standard non-linear regression analysis. The relative potency for various PTHrP analogs (in units/mg) can be determined from the ratio of the $EC_{50}$ of the reference standard analog to that of the PTHrP analog. $EC_{50}$ is defined as the dose that evokes a half-maximal response—cAMP accumulation herein. The detailed procedure for handling the cells, setting up the assay, as well as methods for cAMP quantitation, is described in Sistane et al., *Pharmacopeial Forum* 20: 7509-7520 (1994).

For in vivo assays, candidate PTHrP analogs can be characterized by their abilities to increase trabecular and cortical bone mass in ovariectomized, osteopenic rats, as described in Example 4.

Example 5 describes a three-month double blind, prospective, placebo-controlled randomized clinical trial, demonstrating the effectiveness of PTHrP as a skeletal anabolic agent. PTHrP displays minimal side effects, for example, despite the comparatively high doses, no significant increase in hypercalcemia is observed.

Example 6 describes a computer system and methods of using the same, for structural based design of peptidomimetics and small molecules having skeletal anabolic biological activity.

The following examples are provided for illustrative purposes only, and are in no way intended to limit the scope of the present invention.

EXAMPLE 1

Short-Term, Very High-Dose Treatment of Postmenopausal Osteoporosis with the Skeletal Anabolic Agent PTHrP Parathyroid hormone-related protein, or "PTHrP", is the quintessential skeletal catabolic agent. It was initially discovered as the cause of the common lethal paraneoplastic syndrome, humoral hypercalcemia of malignancy or "HHM". Hypercalcemia occurring among patients with HHM results principally from a striking activation of osteoclastic bone resorption. Thus, PTHrP would seem an unlikely candidate as a skeletal anabolic agent.

The purpose of the present study was to determine whether the administration of intermittent high doses of a PTHrP peptide, for a short period of time could produce significant increases in BMD without negative side effects, and that as such, PTHrP might be an effective skeletal anabolic agent in women with postmenopausal osteoporosis. Reasoning that parathyroid hormone (PTH) can cause demonstrable increases in bone mineral density within three months of treatment, and that PTHrP would need to be at least as effective as PTH in increasing bone mass to be useful therapeutically, the study described herein as Example 1 is three month double-blinded, randomized placebo-controlled pilot clinical trial in which PTHrP was compared to placebo treatment.

The rate of increase, as well as the absolute increase, observed in lumbar spine bone mineral density with PTHrP are large, and may equal or exceed those reported to date using currently available osteoporosis drugs.

PTHrP administered subcutaneously in high doses for only three months appears to be a potent anabolic agent, producing a 4.7% increase in lumbar spine BMD. This compares very favorably to available anti-resorptive drugs for osteoporosis, and PTH. Despite the high doses, PTHrP was well tolerated.

Materials and Methods

Preparation of hPTHrP-(1-36) and Placebo for Human Injection

Synthetic hPTHrP-(1-36) was prepared by solid-phase synthesis, as previously described (Everhart-Caye et al. *J Clin Endocrinol Metab* 81: 199-208 (1996)).

Briefly, hPTHrP-(1-36) was weighed, dissolved in 10 mM acetic acid, filtered through a sterile 0.2 μm syringe filter, aseptically aliquoted into 5-600 μg aliquots in sterile glass vials, aseptically sealed into the vials, frozen at –80° C., and lyophilized. Placebo vials were prepared in exactly the same manner. The vials were stored at –80° C. Peptide content was confirmed by amino acid analysis, PTHrP-(1-36) RIA (described below) or PTHrP-(1-36) RNA, and adenylyl cyclase bioassay (described below). Pyrogen testing was performed by *limulus amebocyte* lysate gel-clot assay method (Associates of Cape Cod, Falmouth, Mass.), using standard endotoxin from *Escherichia coli* 0113 as a control. The endotoxin concentration in the vials was below the lower limit of detection (<0.03 endotoxin units/mL). The vials were labeled in coordination with the University of Pittsburgh Medical Center Investigational Pharmacy. Immediately previous to the beginning of each injection, the PTHrP-(1-36) from a vial was reconstituted in 1.0 mL 0.9% saline. The mass of hPTHrP (1-36) is 4260.6 Da. The structures of the peptides were confirmed by mass spectroscopy and amino acid analysis. Greater than 99% purity was confirmed by reverse-phase high performance liquid chromatography.

Adenylyl Cyclase Bioassay

The biological potency of hPTHrP-(1-36) was tested using an adenylyl cyclase assay performed in confluent SaOS2 human osteosarcoma cells, using a method previously described in detail (Everhart-Caye et al. *J Clin Endocrinol Metab* 81: 199-208 (1996); Orloff et al. *Endocrinol* 131: 1603-1611 (1992); Merendino et al. *Science* 231: 388-390 (1986)). Briefly, SaOS2 cells were obtained from American Type Culture Collection, Rockville, Md., and were maintained in McCoy's medium supplemented with 10% FBS, 2 mmol/L L-glutamine, penicillin (50 U/mL), and streptomycin (50 μg/mL). Cells were plated approximately 10 days before assay in 24-well plates and had been confluent for approximately 7 days previous to assay. The cells were incubated at 25° C. with isobutylmethylxanthine (500 mmol/L) for 10 min, the peptides added, and the incubation continued at 25° C. for another 10 min. Medium was aspirated, the cells solubilized in 5% trichloroacetic acid, and the extracts neutralized using 25:75% trioctylamine:Freon. Content of cAMP in the extracts was measured by RIA (Biomedical Technologies, Stoughton, Mass.). The peptide was examined in at least three different assays.

PTHrP RIA

The hPTHrP-(1-36) RIA using antiserum S2 has been described in detail previously (Yang et al., *Biochem.*, 33: 7460-7469 (1994); Burtis et al., *N. Engl. J. Med.*, 322: 1106-1112 (1990)). Briefly, the lactoperoxidase method was used to prepare $^{125}$I-labeled Tyr$^{36}$PTHrP-(1-36) amide for use as radioligand (see below) as described previously (Orloff et al. *J. Biol. Chem.*, 264: 6097-6103 (1989)). Duplicates of assay standard or sample (100 μL) were incubated overnight at 4° C. with (100 μL) of a 1:1500 dilution of S-2 in P10BT buffer (PBS containing 10% BSA and 0.1% Triton X-100). Iodinated Tyr$^{36}$ of a 1:1500 dilution of S2 in P10BT buffer (PBS containing 10% BSA and 0.1% Triton X-100). Iodinated Tyr$^{36}$hPTHrP-(1-36)amide (2000-

8000 cpm) in PBT buffer was added to the tubes, and the mixture was incubated overnight at 4° C. Phase separation was accomplished using dextran-coated charcoal. The sensitivity of the assay is 50 pmol/L. The antiserum recognizes hPTHrP-(1-74), (1-36) and (1-141) with equal affinity, but fails to cross-react with hPTHrP-(37-74) or with hPTH-(1-34) or hPTH-(1-84) (Yang et al., *Biochem.*, 33: 7460-7469 (1994)).

Serum and Urine Biochemistries

Blood was analyzed for routine chemistry and hematology studies in the University of Pittsburgh Medical Center Clinical Chemistry Laboratory, as were plasma 25-vitamin D concentrations. Osteocalcin was measured as described in Gundberg, et al., J Clin Endocrinol Metab 83:3258-3266, (1998), incorporated by reference. Serum N-telopeptide (N-Tx) (Osteomark) and urinary deoxypyridinolines (DPD) (Pyrilinks-D) were measured using commercial kits from Ostex International, Seattle Wash., and Quidel Corp, Santa Clara Calif., respectively.

Study Subjects

Sixteen consecutive healthy postmenopausal women with osteoporosis were identified for this study. All study subjects provided informed consent. The participants in the experimental and control groups were of similar age (mean age approximately 65), weight, height, BMI, years since menopause, years on estrogen, calcium intake, and had similar plasma 25 vitamin D concentrations. Both groups displayed osteoporosis at the lumbar spine.

Before beginning the study, each subject underwent a bone mineral density scan (DXA) of the lumbar spine and hip at the beginning and at the conclusion of the study. Inclusion criteria included a T-score of less than −2.5 at the lumbar spine, being more than three years postmenopausal, being on estrogen replacement for at least three years, and being in generally excellent health. Exclusion criteria included use in the past of any osteoporosis medication, including bisphosphonates, calcitonin, or selective estrogen receptor modifiers. Current use of medications or agents that might influence calcium or bone metabolism (e.g., thiazides, non-physiologic doses of thyroid hormone, glucocorticoids, lithium, alcohol, etc.) was also an exclusion criterion. All study subjects provided informed consent. The protocol was approved by the University of Pittsburgh Institutional Review Board.

Study Protocol

The use of PTHrP in human clinical trials was approved by the FDA (IND # 49175, incorporated herein by reference). The protocol was approved by the University of Pittsburgh Institutional Review Board. This was a randomized, double-blinded placebo-controlled clinical trial. The primary outcome measure was lumbar spine bone mineral density. Secondary outcome measures were hip and femoral neck bone mineral density, markers of bone turnover, serum calcium, serum creatinine, renal phosphorus handling and adverse events.

The sixteen subjects were randomized to receive three months of treatment with either PTHrP or placebo (identically prepared empty vials containing no PTHrP). Each subject also received 400 IU of vitamin D and 1000 mg of calcium as calcium carbonate per day (Os-Cal, Smith Kline Beecham/Glaxo, King of Prussia, Pa.), and this was started two weeks before the initiation of PTHrP or placebo treatments. Subjects were taught in the home storage at −20° C., reconstitution and self-injection of P or placebo. Vials were reconstituted by the study subjects in 1.0 ml of sterile bacteriostatic saline immediately prior to use, to an average dosage of PTHrP of 410.25 μg per day, or saline placebo, and was self-administered into the abdominal subcutaneous fat. Subjects returned for blood and urine studies at 0, 14, 30, 60 and 90 days of the study. A final bone density study was performed on day 90 of the study.

Study Compliance

One patient in the placebo group dropped out of the study after three days. The remaining subjects in each group completed the study without event. The data analysis which follows includes all 16 patients at baseline, and the eight PTHrP and seven placebo subjects who completed the three months of the study.

Safety Considerations

Study subjects were monitored at 0, 2, 4, 8, and 12 weeks for hypercalcemia, rashes, GI complaints, cardiovascular complaints or symptoms, or other non-specific complaints. Subjects were questioned regarding adverse effects at each visit, i.e., 0, 14, 30, 60 and 90 days of the study.

Bone Densitometry

Bone densitometry at the spine and hip was measured blindly using a Model 2000 densitometer (Hologic Inc. Bedford Mass.). The results were blindly and independently reviewed by two physicians experienced bone densitometrists.

Statistical Analysis

Statistical analysis was performed using Student's unpaired T-test, using Excel software (Microsoft, Seattle, Wash.). P-values less than 0.05 are considered significant.

Results

Baseline Demographics.

The baseline demographics in the two groups are shown in Table I. The subjects were of similar age, weight, height, BMI, years since menopause, years on estrogen, calcium intake, and had similar plasma 25 vitamin D concentrations. In the placebo group, two were smokers and one was on a normal replacement dose of thyroid hormone for hypothyroidism. Both groups displayed osteoporosis at the lumbar spine.

Study Compliance.

One patient in the placebo group dropped out of the study after three days because of shortness of breath and chest tightness following a subcutaneous injection. The remaining subjects in each group completed the study without event. The following data analysis includes all 16 patients at baseline, and the eight PTHrP and seven placebo subjects who completed the three months of the study.

Primary Outcome

L/S BMD

The changes in BMD at the lumbar spine over the three months of the study are shown in FIG. 4. The left panel shows the changes in bone mineral density as measured by DXA as percent changes from baseline. The right panel shows the same data as absolute changes in bone mineral density from baseline in gm/cm$^2$. In each panel, the bold line represents the subjects treated with PTHrP (n=8 indicates that all eight PTHrP treated patients are included), and the dotted line, those receiving placebo.

In the placebo group, the data are presented including the outlier (+) and with the outlier excluded (−), as described in the text (n=6/7 indicates the numbers of subjects receiving placebo including or excluding he outlier). The error bars represent SEM. P-values were determined using Student's paired T-test. As can be seen in the left panel, the increase in BMD at the lumbar spine in the PTHrP group was 4.72% over three months. In contrast, the change in the placebo group was smaller, 1.4%, p=0.025. This surprisingly large increment in the placebo group reflected a 6.5% increase in one subject. The reason for the marked increase, 6.5%, in BMD in the single placebo outlier is unknown. The increase was confirmed by independent blinded review of DXA scans, and was not due to positioning or other technical considerations. This subject was no different than the other placebo subjects in total hip or femoral neck BMD at baseline or at the conclusion, and was no different with regard to baseline spine BMD. There was no evidence of a vertebral compression fracture before or after the study, and there was no aortic or arthritic calcification. This subject had one of the lowest plasma 25 vitamin D concentrations in the study (16 ng/ml), and it is possible that a component of this subject's marked increase reflected correction of mild osteomalacia. If this subject is excluded, the increase in the placebo group was 0.6%, p=0.003. Similar findings were obtained when the results are expressed as absolute changes in BMD in grams per $cm^2$ (right panel), with the increment in the PTHrP group being 0.0375 $gm/cm^2$, and 0.011 or 0.005 $gm/cm^2$ in the placebo group, depending on whether the outlier is included (p=0.022) or excluded (0.003).

Secondary Outcomes

Femoral Neck and Total Hip BMD

Figure 5:
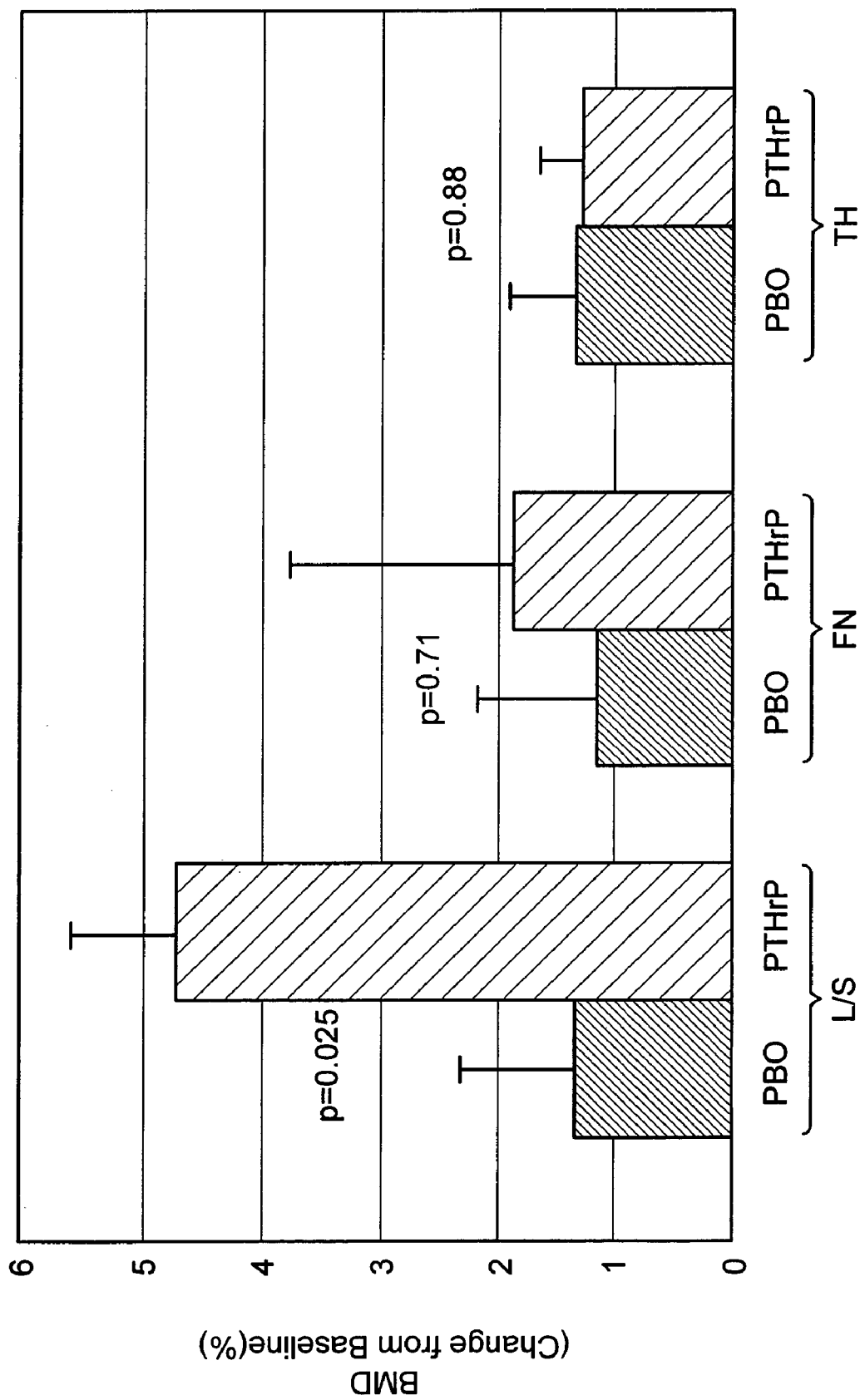
FIG. 5 illustrates changes in bone mineral density as percent changes from baseline, following treatments with PTHrP or a placebo (PBO), as measured at the lumbar spine (US), the femoral neck (FN) and the total hip (TH). There is a marked increase in bone mineral density at the lumber spine in response to PTHrP treatment, a more moderate increase at the femoral neck, and approximately no increase in bone mineral density at the total hip.

The changes in BMD expressed as percent change from baseline at the total hip and femoral neck are shown in FIG. 5, and are compared to the changes at the lumbar spine. The light gray bars indicate the placebo group (PBO), and the black bars indicate the experimental group (PTHrP). The IUS data are the same as those presented in FIG. 4 and include the outlier. The error bars indicate SEM, and P-values were determined using Student's paired T-test. There was no significant difference between the PTHrP or PBO groups at either hip site during the study.

Bone Turnover Markers

Figure 6A:
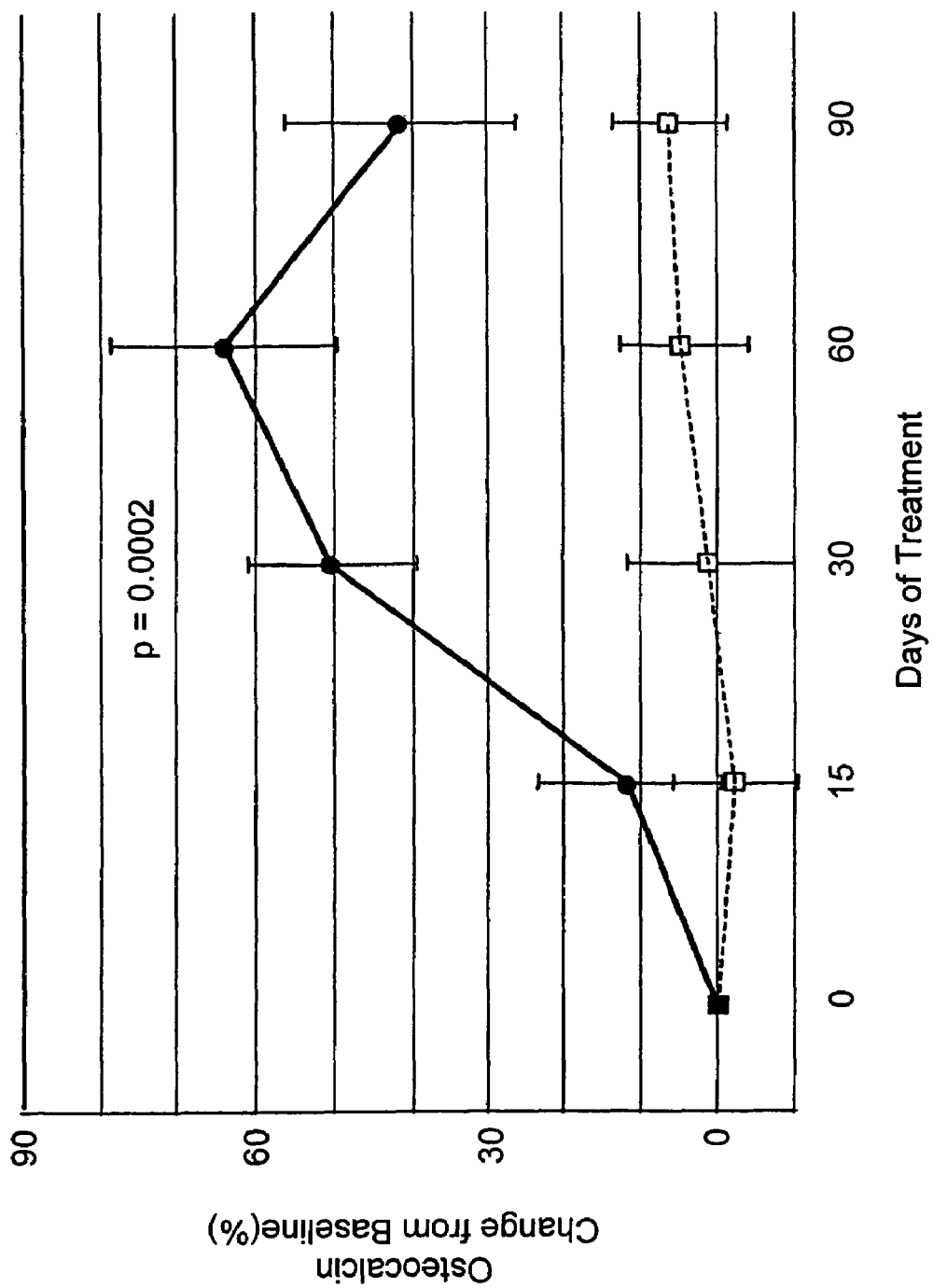
FIG. 6(a) demonstrates the serum osteocalcin results expressed as change from baseline.

FIG. 6 illustrates three different bone turnover markers in the placebo and PTHrP-treated subjects. FIG. 6(a) illustrates serum osteocalcin, a marker of bone formation, increased in a statistically significant fashion during the study in the PTHrP-treated subjects but not the placebo controls. Indeed, as illustrated in FIG. 6(a), increases in serum osteocalcin were apparent as early as day 15 (the earliest time period blood samples were obtained).

Figure 6B:
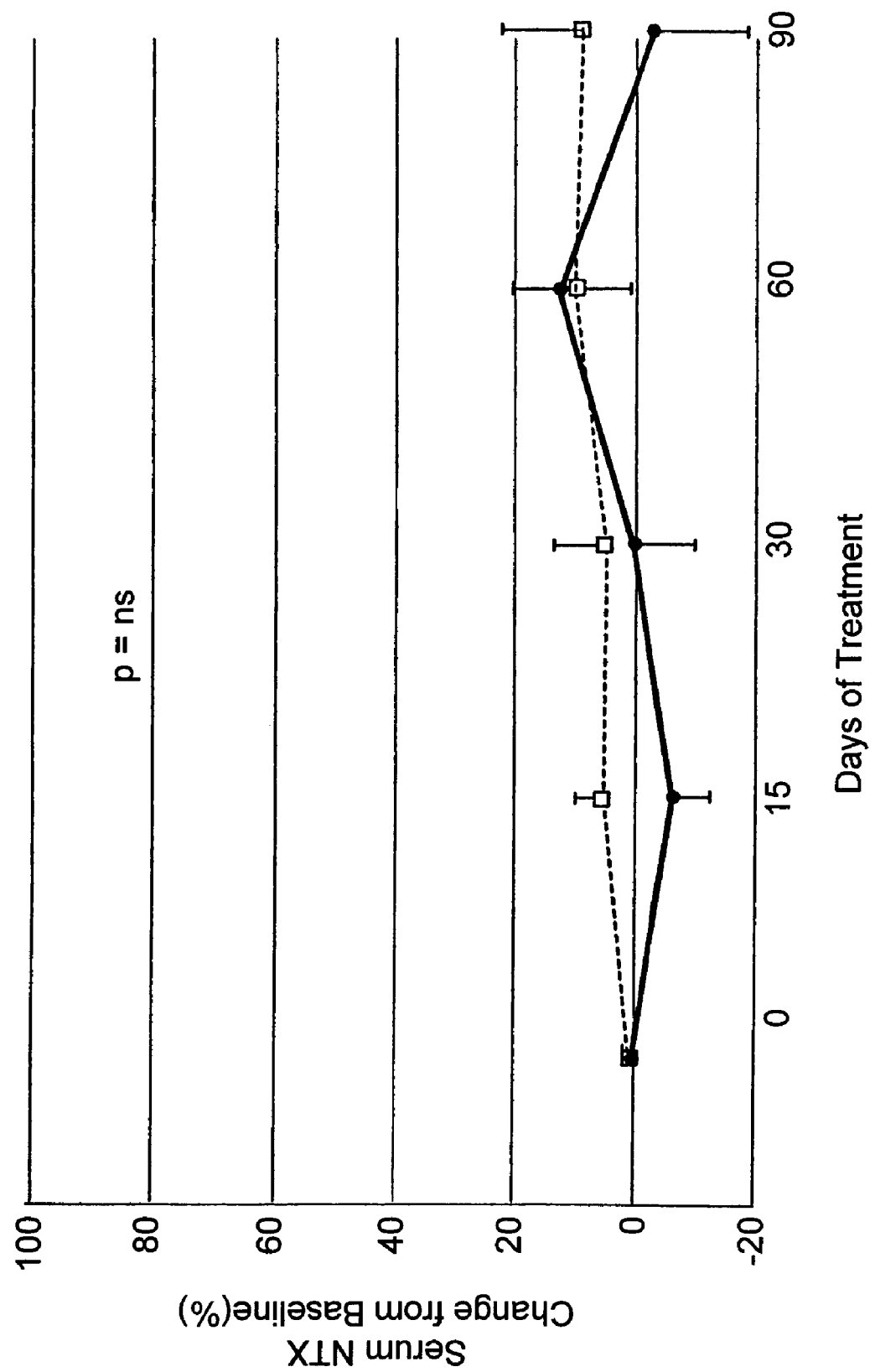
FIG. 6(b) indicates the serum N-telopeptide (NTX) values in the two groups.
Figure 6C:
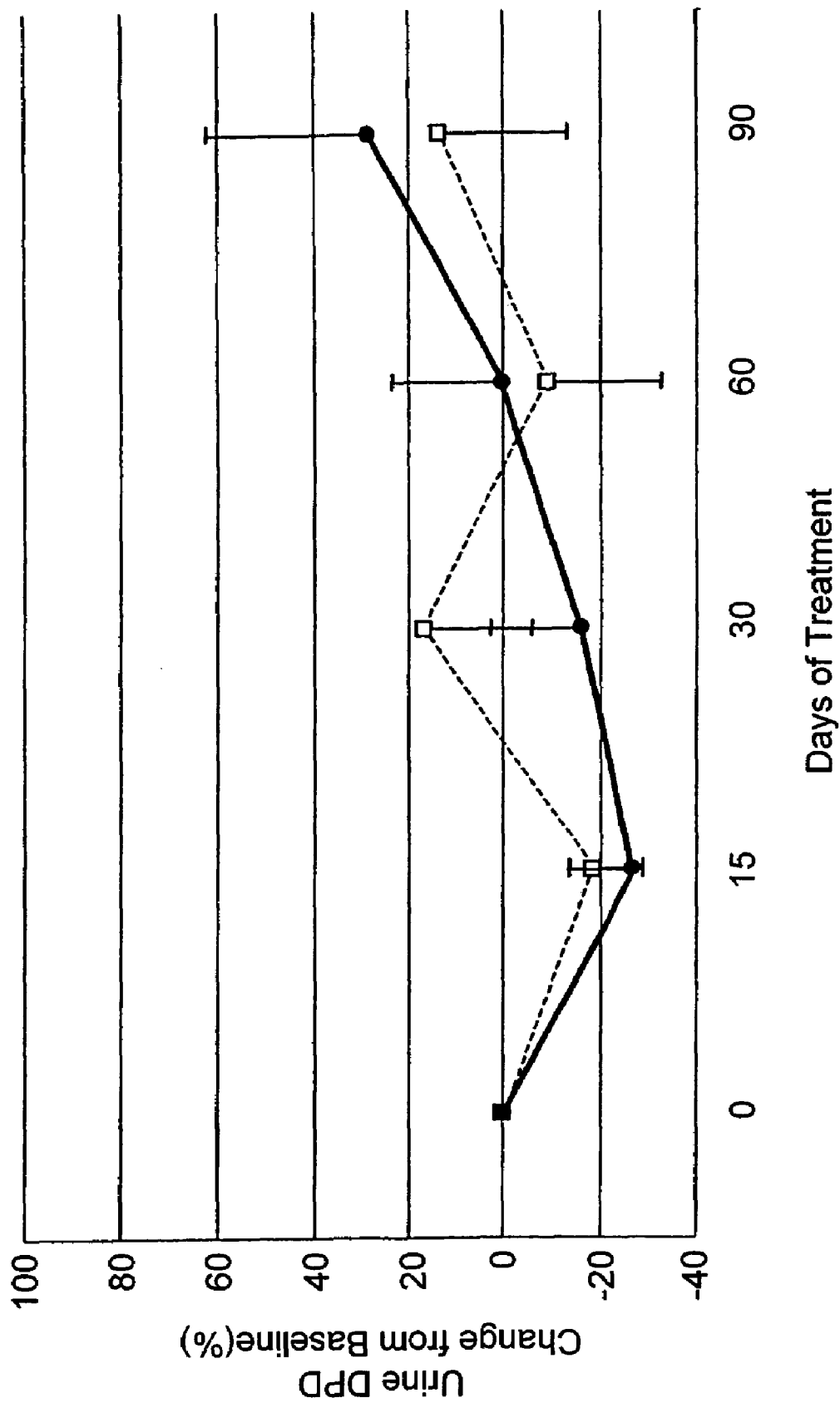
FIG. 6(c) indicates the urinary deoxypyridinolines in the two groups. The results demonstrate that PTHrP stimulates serum osteocalcin, and by inference, bone formation, but not bone resorption.

In contrast, serum NTX, a marker of bone resorption, remained unchanged during the study in the PTHrP-treated subjects, as it did in the placebo controls, as shown in FIG. 6(b). Urinary DPD excretion, a second marker of bone resorption, was also unchanged, see, FIG. 6(c). In all three figures, the dotted line indicates the placebo group and the sold line the PTHrP group. The error bars indicate SEM, and the P-values were determined using ANOVA for repeated measures. These findings suggest that PTHrP selectively stimulates bone formation without further stimulating normal rates of bone resorption.

Serum and Urine Chemistries

Figure 7:
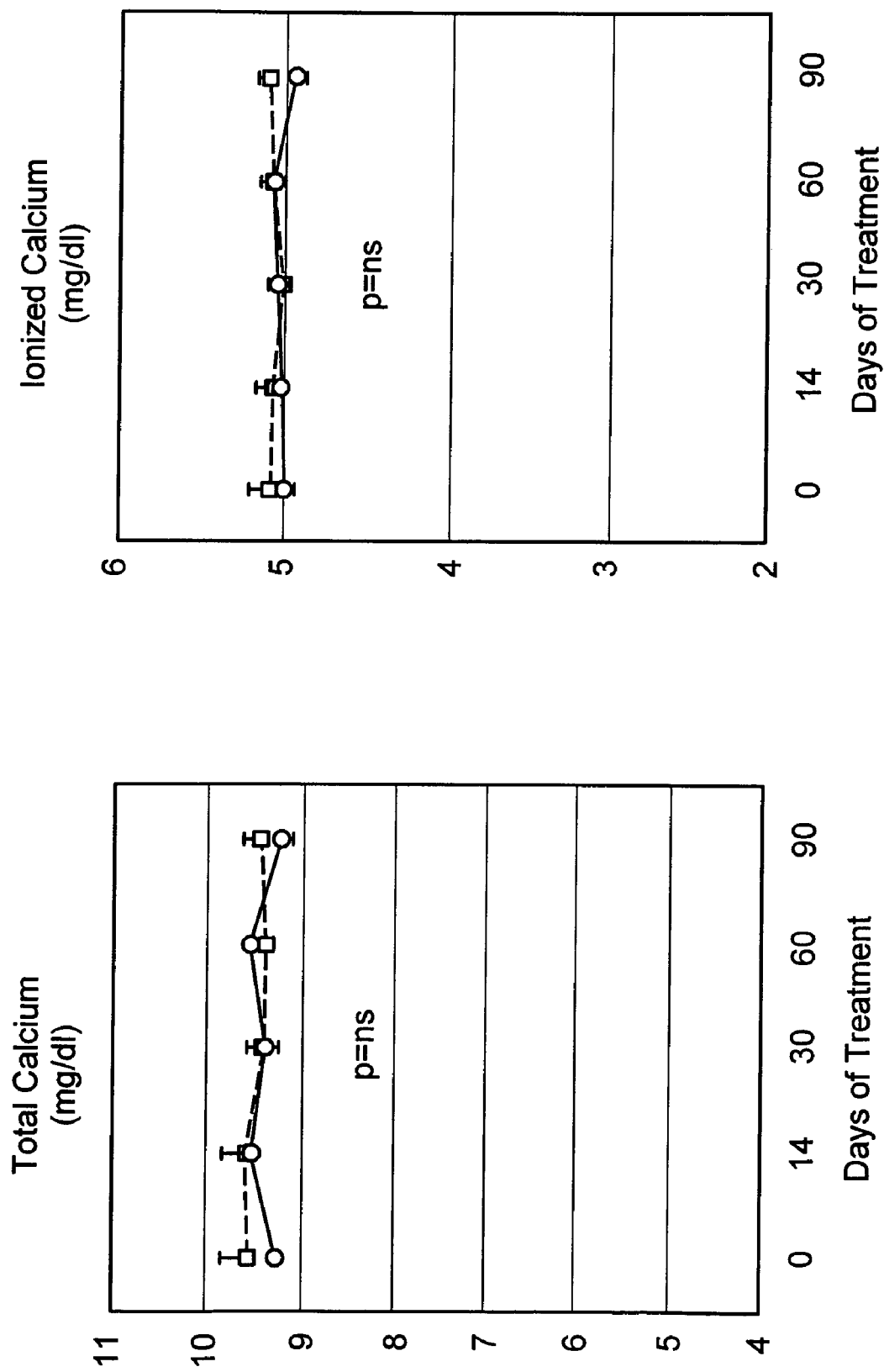
FIG. 7 illustrates serum total calcium (left panel) and ionized calcium (right panel) in the PTHrP and placebo groups. There is no difference in serum total or ionized calcium between the, PTHrP and control groups, and no patient in either group developed hypercalcemia as measured by total or ionized serum calcium.

FIG. 7 illustrates serum total and ionized serum calcium in the placebo and PTHrP-treated subjects. The dotted line indicates the placebo group and the sold line, the PTHrP group. The error bars indicate SEM, and the P-values were determined using ANOVA for repeated measures. Calcium levels remained normal and constant in both the PTHrP-treated subjects as well as in the placebo controls. No subject developed a significant increase in serum total or ionized calcium. Serum creatinine remained normal as well in both the PTHrP and placebo subjects (mean serum creatinine, ±SEM, on day 90=0.825±0.05 mg/dl in the PTHrP group vs. 0.84±0.06 in the placebo group, p=ns). Serum phosphorus was also similar in both groups throughout the study (3.2 mg/dl±0.18 in the PTHrP group vs. 2.9±0.17 in the placebo group, p=ns), as was the tubular maximum for phosphorus (3.3 mg/dl±0.27 in the PTHrP group vs. 2.6±0.24 in the placebo group, p=ns).

Figure 8:
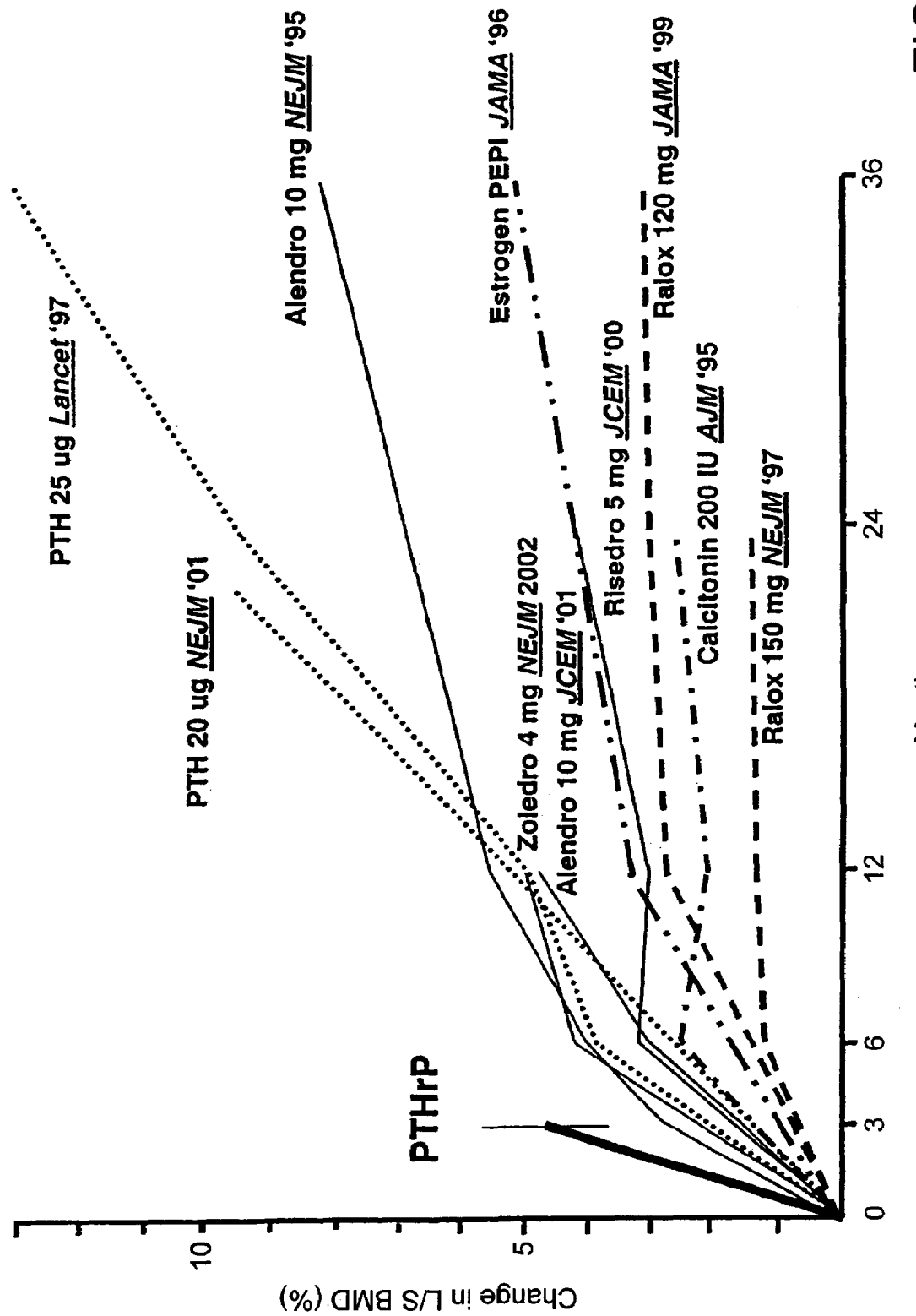
FIG. 8 is a line graph depicting the changes in lumbar vertebral bone mass density (BMD) expressed as % change in postmenopausal women with osteoporosis receiving placebo (N=7) or 410.25 μg/day of PTHrP-(1-36) (N=8) compared to the effects of various other osteoporosis drugs reported in other published clinical studies.

FIG. 8 illustrates a comparison of the anabolic activity of PTHrP with results from selected previously published osteoporosis clinical trials. "Ralox 150" refers to Delmas P D, et al., N Engl J Med 337:1641-7, (1997); "Ralox 120" to Ettinger B, et al., JAMA 282:63745, (1999); and "calcitonin" to Chestnut C, et al., Osteoporosis Int 8(suppl 3):13 (1998); "alendro", "risedro" and "zoledro" refer to studies employing alendronate (Liberman U A, et al., N Engl J Med 333:1437-43, (1995) and Murphy M G, et al., J Clin Endocrinol Metab 86:1116-25, (2001), to risedronate (Fogelman I, et al., J Clin Endocrinol Metab., 85:1895-1900, (2000) and McClung M R, et al, N Engl J Med 344:333-40, (2001), and to zoledronate, Reid I R, et al., N Engl J Med 346:653-61, 2002.). "PTH" refers to two studies employing parathyroid hormone, Lindsay R, et al., Lancet 350:550-5 (1997), and Neer R M, et al., N Engl J Med 344:1434-41 (2001), and "PTHrP" refers to the current study. Each of the foregoing references are hereby incorporated herein by reference in their entirety.

Adverse Events

No subject in the PTHrP group experienced weakness, nausea, vomiting, diarrhea, constipation, flushing, muscle cramps or allergic phenomena. One PTHrP subject experienced 30 seconds of heart palpitations with standing after the third injection, which did not recur with subsequent injections. All PTHrP subjects completed the study. In contrast, one subject in the placebo group experienced flushing, dizziness and nausea after her injection on day three of the study, and this subject withdrew from the study.

Discussion

These studies indicate that PTHrP, administered subcutaneously in very large doses over a very brief period of time, can cause statistically and biologically important increments in spine bone density. This is surprising for a number of reasons. First, PTHrP was originally identified as a result of its skeletal catabolic actions in humoral hypercalcemia of malignancy. Second, the rate and absolute increment in spine BMD, almost 5% in three months, is larger than those observed using many currently available anti-resorptive osteoporosis medications, (see, FIG. 8). Indeed, increments of this magnitude have never been reported using calcitonin nor raloxifene, even when these agents are given for as long as three years. Estrogen causes similar increments in spine BMD, but a change of 5% requires three years of treatment. The changes observed using some bisphosphonates, including etidronate, alendronate, risedronate, and zoledronate, may equal or exceed 5%, but require far longer than three months, typically one or more years. Indeed, the changes observed compare favorably to, and may possibly exceed those observed in studies reported to date using PTH over a three month period. Viewed from the perspective of available anti-resorptive therapies, the effects of short-term high dose PTHrP are striking.

The doses of PTHrP employed in this study were large compared to those used in similar PTH studies. Subjects in this study received 6.56 micrograms/kg/day, which on average was 410.25 micrograms per day in the eight subjects who received PTHrP. This is some 10- to 20-fold larger than doses of hPTH(1-34) (20-40 micrograms/day) commonly employed in osteoporosis studies. Doses of PTH in excess of 20 micrograms/day are associated with hypercalcemia and other adverse effects in humans. It is surprising, therefore, that healthy subjects would tolerate doses of this magnitude without developing hypercalcemia, postural hypotension, nausea, flushing or other adverse effects. The differences cannot be ascribed to differences in molar amounts of the two peptides employed, for PTHrP(1-36) is very close in molecular weight to PTH(1-34) (approximately 4200 Mr). Nor can the differences be ascribed to different interactions with the common PTH/PTHrP receptor: both hPTH(1-34) and hPTHrP(1-36) display similar or identical binding kinetics and signal transduction activation characteristics. Importantly, in head-to-head comparison with hPTH(1-34) in vitro and also in vivo given intravenously to human volunteers, PTHrP(1-36) is equal in potency to hPTH(1-34). Different serum metabolic clearance rates are an unlikely explanation as well, for we have demonstrated that the $T_{1/2}$ of intravenously infused PTHrP(1-36) is six minutes, indistinguishable from the five to six minutes reported for hPTH(1-34).

The differences in skeletal effects of the two peptides relate to differing pharmacokinetic characteristics of PTH and PTHrP following subcutaneous injection. Human PTH (1-34) has been reported in two studies to reach peak plasma levels at 30-45 minutes following injection, whereas we have reported that peak plasma levels of PTHrP occur at or before 15 minutes following a subcutaneous dose. Indeed, since the 15 minute time point was the first we examined, and since circulating PTHrP values appeared to be in a sharp decline at this initial 15 minute time point, it is very likely that the peak occurs much earlier, perhaps at five to ten minutes. Thus, hPTHrP(1-36) is absorbed more rapidly than PTH following subcutaneous injection, and plasma levels of PTHrP reach their peak and therefore decline more rapidly than those of PTH.

The different absorption and clearance kinetics of PTHrP vs. PTH underlie the requirement for large dose of PTHrP as well as the lack of hypercalcemia and other toxicities observed in the patients studied despite these large doses. This apparent safety is supported by our a prior studies in which an additional seven subjects received the same 6.56 micrograms/kg/day dose for two weeks with no adverse events, and another study in which this dose was administered as a single dose to three health individuals. Thus, no adverse events have been encountered in a total of 18 healthy human subjects receiving these large doses of PTHrP for periods of one day, two weeks or three months.

Mechanistically, the bone turnover marker data (see, FIGS. 6(a), (b), and (c)) suggest that PTHrP may have purely anabolic effects on the skeleton, without the accompanying increase in bone resorption observed using PTH. Thus, in contrast to PTH, which displays both formation- and resorption-stimulating properties, PTHrP appears to have selective osteoblastic or anabolic effects, without concomitant resorption-stimulating effects. The lack of a resorptive effect is unlikely to be due to concomitant estrogen use since the resorptive response to PTH is not abolished by estrogen. Interestingly, while the rate of increase in BMD in the current study was very large, the total increase in the formation marker osteocalcin was either similar to, or significantly lower than that reported using PTH. The apparent relatively lower increase in formation, in the setting of a rather dramatic increase in BMD, supports the biochemical evidence for an apparent lack of a resorption-stimulating effect. Confirmation of these finding can be made using skeletal biopsies and quantitative bone histomorphometry.

The lack of a resorptive effect is not likely due to the brief duration (three months) of administration of PTHrP, since prior studies have shown that PTH increases bone resorption significantly at or well before three months. For example, in a study Lindsay et al. (*Lancet* 350: 550-555 (1997)), resorption as assessed using urinary NIX, was already elevated at two weeks, and was increased by 25% at three months. Finkelstein et al. (*N Engl J Med* 331: 1618-1623 (1994)) demonstrated that urinary hydroxyproline and pyridinolines, two different markers of bone resorption, were increased by approximately 200% at three months following treatment with PTH. Similarly, Hodsman (*J Clin Endocrinol Metab* 82: 620-628 (1997)) has demonstrated that both urinary hydroxyproline and NTX are significantly increased by only four weeks of treatment using PTH.

Similarly, the lack of a resorptive effect is unlikely to be due to concomitant estrogen use. First, the same type of dissociation was observed in our earlier study in postmenopausal women without estrogen use (Plotkin et al., *J Clin Endocrinol Metab* 83: 2786-2791 (1998)). Second, the resorptive response to PTH is easily apparent in estrogenized women in both the Roe and the Lindsay studies at three months (Roe et al., *Program and Abstracts of the 81st Annual Meeting of the Endocrine Society*, San Diego, Calif., Jun. 12-15, 1999, p. 59; Lindsay et al., *Lancet* 350: 550-555 (1997)). Thus, from the data available to date, it appears that PTHrP, in the doses employed thus far, and for the duration observed to date, may be different from PTH and may display purely anabolic affects.

Assuming that the selective anabolic effect is reproducible in longer and larger studies as described above, it is hypothesized that the differences in bone formation and resorption between PTH and PTHrP also may result from their different pharmacokinetics following subcutaneous absorption as described above. It is well known that longer exposure of osteoblasts or their precursors in vitro or in vivo to PTH diminishes the anabolic response, whereas it augments the osteoclastic resorptive response (see, Rosen & Bilezikian, *J Clin Endocrinol Metab*. 86: 957-964 (2001); Dempster et al., *Endocrine Reviews* 14: 690-709 (1993); Dobnig & Turner, *Endocrinology* 138: 4607-4612 (1997)). By serendipity, the accelerated absorption and clearance of PTHrP following subcutaneous injection, as compared to those of PTH, may further favor the formation vs. resorption balance.

The doses of PTHrP employed in this study were very large. Subjects in this study received an average dosage 410.25 μg per day in the eight subjects who received PTHrP. This is some 10- to 20-fold larger than doses of hPTH(1-34) (20-40 μg/day) commonly employed in osteoporosis studies. Doses of PTH in excess of 20 μg/day are known to be associated with hypercalcemia and other adverse effects. It is surprising, therefore, that healthy subjects would tolerate PTHrP doses of this magnitude without developing hypercalcemia, postural hypotension, nausea, flushing or other adverse effects. The differences cannot be ascribed to differences in molar amounts of the two peptides employed, for PTHrP(1-36) is very close in molecular weight to PTH(1-34) (approximately 4200 Mr). Nor can the differences be ascribed to different interactions with the common PTH/PTHrP receptor: both hPTH(1-34) and hPTHrP(1-36) display similar or identical binding kinetics and signal transduction activation characteristics, in humans. Different serum metabolic clearance rates are an unlikely explanation as well, for it has been demonstrated that the $T_{1/2}$ of intravenously infused PTHrP(1-36) is about six minutes, indistinguishable from the approximately five to six minutes reported for hPTH(1-34). Without being restricted to theory, one possible explanation is that the differences in skeletal effects of the two peptides relate to differing pharmacokinetic characteristics of PTH and PTHrP following subcutaneous injection. Human PTH(1-34) reaches peak plasma levels at about 30-45 minutes following injection, whereas peak plasma levels of PTHrP occur at or before about 15 minutes following a subcutaneous dose. Thus, hPTHrP(1-36) is likely more rapidly absorbed than PTH following subcutaneous injection, and plasma levels of PTHrP reach their peak and decline more rapidly than those of PTH.

These pharmacokinetic differences may also account for the selective or pure anabolic response observed. It is well known that longer exposure of osteoblasts in vitro or in vivo to PTH diminishes the anabolic response, whereas it augments the osteoclastic resorptive response. The accelerated absorption and clearance of PTHrP following subcutaneous injection, as compared to those of PTH, may further favor the formation vs. resorption balance.

In this study, subjects in both the placebo and PTHrP groups were concomitantly receiving estrogen, in addition to calcium and vitamin D supplements, in part, for ethical reasons, so that the placebo group would receive some form of currently accepted treatment for osteoporosis. As for PTH, it remains to be determined whether the anabolic effect of PTHrP is enhanced by concomitant use of estrogen. Studies using PTH in humans in general show similar efficacy whether the subjects are receiving estrogen or not (see, FIG. 8), although there have been no studies to date directly addressing this question for PTHrP. Whether PTHrP might be more or less effective when given concomitantly with other anti-resorptive agents (bisphosphonates, selective estrogen receptor modulators, etc.) remains to be determined.

Short-term, very high dose treatment with PTHrP(1-36) causes a remarkable increase in spine BMD. In contrast to the combined or net resorptive and anabolic skeletal effects of intermittently administered PTH, PTHrP appears to have predominantly anabolic effects with little or no resorptive component. The differences between PTH and PTHrP are not likely to reflect differences in receptor interactions or signaling between the two molecules, but likely reside in the differing pharmacokinetic properties of the two molecules following subcutaneous administration.

Of the seven subjects receiving placebo for four months, six subjects demonstrated no significant change in bone mineral density (BMD) at either the hip or spine. One placebo subject did display a 6% increase in spine BMD. This is clearly not the expected or typically encountered response to placebo (The writing group for the PEPI trial, JAMA 276: 1389-1396 (1996); Delmas et al., N Engl J Med 337: 1641-1647 (1997); Chestnut et al., Osteoporosis Int 8 (suppl 3): 13 (1998); Liberman et al., N Engl J Med 333: 1437-1443 (1995); McClung et al., N Engl J Med 344: 33340 (2001); Finkelstein et al., N Engl J Med 331: 1618-1623 (1994); Hodsman et al., J Clin Endocrinol Metab 82: 620-28 (1997); Lindsay et al., Lancet 350: 550-555 (1997); Neer et al., N Engl J Med 344: 1434-1441 (2001); Roe et al., Program and Abstracts of the 81st Annual Meeting of the Endocrine Society, p. 59 (1999); Lane et al., J Clin Invest 102: 1627-1633 (1998)), suggesting that this subject may have had baseline vitamin D deficiency, or an incidental radiologically non-apparent vertebral compression fracture.

As illustrated in FIG. 4, the eight subjects receiving PTHrP demonstrated important increases in lumbar spine BMD, with a mean value of approximately 4.75%. When compared to all seven controls, including the placebo outlier, the results are significant (p=0.026). When compared to the six truly normal placebo controls, the results are highly significant (p=0.003).

These results are quite extraordinary and surprising for several reasons. First, none of the available osteoporosis drugs, the anti-resorptives, yield these kinds of increments in BMD in such a short time frame (The writing group for the PEPI trial, JAMA 276: 1389-1396 (1996); Delmas et al., N Engl J Med 337: 1641-1647 (1997); Chestnut et al., Osteoporosis Int 8 (suppl 3): 13 (1998); Liberman et al., N Engl J Med 333: 1437-1443 (1995); McClung et al., N Engl J Med 344: 333-40 (2001)). As illustrated in FIG. 8, the rate of increase in BMD observed in the present study are greater than the rates of BMD increase reported in previous clinical studies. The results are extremely rapid: three months of PTHrP-(1-36) therapy yielded increases not generally observed for two to three years with anti-resorptives as described above. Indeed, several available anti-resorptives (SERMs, calcitonin, vitamin D, calcium) never achieve these increments in BMD.

Second, the results are comparable, or superior, to those achieved using PTH, the best studied anabolic skeletal agent to date (Finkelstein et al., N Engl J Med 331: 1618-1623 (1994); Hodsman et al., J Clin Endocrinol Metab 82: 620-28 (1997); Lindsay et al., Lancet 350: 550-555 (1997); Neer et al., N Engl J Med 344: 1434-1441 (2001); Roe et al., Program and Abstracts of the 81st Annual Meeting of the Endocrine Society, p. 59 (1999); Lane et al., J Clin Invest 102: 1627-1633 (1998)).

Third, the doses required are surprisingly high: as noted earlier, standard doses of PTH-(1-34) are in the 20-40 µg/day range (Finkelstein et al., N Engl J Med 331: 1618-1623 (1994); Hodsman et al., J Clin Endocrinol Metab 82: 620-28 (1997); Lindsay et al., Lancet 350: 550-555 (1997); Neer et al., N Engl J Med 344: 1434-1441 (2001); Roe et al., Program and Abstracts of the 81st Annual Meeting of the Endocrine Society, p. 59 (1999); Lane et al., J Clin Invest 102: 1627-1633 (1998)), some 10-20-fold lower than those employed herein for PTHrP-(1-36).

Fourth, despite the relatively enormous doses of PTHrP administered in the present study, no adverse events have been encountered, whereas such adverse events have been noted with far smaller doses of PTH (Finkelstein et al., N Engl J Med 331: 1618-1623 (1994); Hodsman et al., J Clin Endocrinol Metab 82: 620-28 (1997); Lindsay et al., Lancet 350: 550-555 (1997); Neer et al., N Engl J Med 344: 1434-1441 (2001); Roe et al., Program and Abstracts of the 81st Annual Meeting of the Endocrine Society, p. 59 (1999); Lane et al., J Clin Invest 102: 1627-1633 (1998)). The absence of toxicity and the requirement for high doses in humans appears comparable to the findings in rats described above, in which equimolar doses of PTHrP had less efficacy and less toxicity as compared to PTH. These observations, as noted above, appear to reflect the serendipitous and non-predictable differences in pharmacokinetics of PTHrP as compared to PTH following subcutaneous administration.

Fifth, PTHrP is widely viewed as the quintessential catabolic skeletal hormone responsible for dramatic skeletal mineral losses in patients with HHM. The observation that PTHrP is actually markedly anabolic for the skeleton when administered "intermittently" (e.g., once per day) was not anticipated. This is evidenced by the fact that many investigators and pharmaceutical firms have worked for more than 10 years (and likely as long as 70 years) with PTH in osteoporosis, but none has embraced PTHrP despite its having been in the public domain since its initial description in 1987.

Finally, the treatment regimen of the present invention for the treatment of osteoporosis has one additional unanticipated and unpredictable strength relating to safety. In preclinical toxicity studies, PTH was administered to growing rats for two years. Some rats developed osteosarcomas after approximately one year of PTH therapy. This suggests that anabolic agent use for periods of less than one year may put humans at less risk than those used for longer periods of time. The early efficacy of PTHrP in human studies suggests that briefer durations of treatment are likely to be effective in humans. Supporting this is the observation that despite the very high doses of PTHrP employed in this study, adverse events have not been observed in human subjects. In addition, the availability of a purely or predominantly anabolic agent may permit combined approaches to treating osteoporosis using concomitant, intermittent or sequential regimens with anti-resorptive agents. According to the methods of the present invention, patients can be treated, for example, initially with a several month course of PTHrP, or an analog or fragment thereof, and then switched to an oral anti-resorptive formulation with no osteosarcoma risk.

In summary, short-term, high dose treatment with PTHrP (1-36) causes a remarkable increase in spine BMD. In contrast to the combined or net resorptive and anabolic skeletal effects of intermittently administered PTH over the same time period, PTHrP may have predominantly anabolic effects with little of a resorptive component. The differences between PTH and PTHrP are not likely to reflect differences in receptor interactions or signaling between the two molecules, but likely reside in the differing pharmacokinetic properties of the two molecules following subcutaneous administration. Despite the very high doses of PTHrP employed, adverse events have not been observed in 18 human subjects. The availability of a purely or predominantly anabolic agent, in addition to PTH, may permit additional combined approaches to treating osteoporosis using concomitant, intermittent or sequential regimens with anti-resorptive agents.

EXAMPLE 2

Characterization of PTHrP Analogs Using Human Bone and Renal Receptors

The purpose of the present study was to characterize various PTH and PTHrP analogs using human bone and human renal receptors. The ability of these analogs to stimulate adenylate cyclase was also examined. For a detailed description of the methods in the present example, see e.g., Orloff et al. *Endocrinol.*, 131: 1603-1611 (1992), incorporated herein by reference.

Materials and Methods

Peptides (Tyr$^{36}$)hPTHrP-(1-36)amide [hPTHrP-(1-36)], hPTHrP-(1-74), and hPTHrP-(37-74) were prepared by solid phase synthesis as previously described (Orloff et al. *J. Biol. Chem.*, 131: 1603-1611 (1992); Stewart et al. *J. Clin. Invest.*, 81: 596-600 (1988)). Synthetic hPTH-(1-34), (Nle$^{8,18}$, Tyr$^{34}$)hPTH-(1-34), bovine (b)PTH-(1-34), rat (r)PTH-(1-34), hPTHrP-(1-86), (Nle$^{8,18}$,Tyr$^{34}$) bPTH-(3-34)amide, (D-Trp$^{12}$, Tyr$^{34}$)bPTH-(7-34)amide, (Tyr$^{34}$)bPTH-(7-34) amide, hPTHrP-(7-34)amide, and hPTH-(13-34) were purchased from Bachem, Inc. (Torrance, Calif.). bPTH-(1-84) was obtained from the National Hormone and Pituitary Program through the National Institute of Diabetes and Digestive and Kidney Diseases (NIDDK). (Tyr$^{36}$) chicken (c)PTHrP-(1-36)amide was purchased from Peninsula Laboratories, Inc., Belmont, Calif. hPTHrP-(1-141) was provided by Genentech, Inc., So. San Francisco, Calif., and transaminated rPTH-(1-34) was provided by Dr. David L. Carnes, Jr. (San Antonio, Tex.). Chicken PTH-(1-34)amide, [Nle$^{8,18}$, D-Trp$^{13}$]bPTH-(7-18)-hPTHrP-(19-34)NH$_2$ and [D-Trp$^{12}$]hPTHrP-(7-18) [Tyr$^{34}$]bPTH-(19-34)NH$_2$ were prepared by solid phase synthesis as described (Caufield et al. *Endocrinol* 123: 2949-2951 (1988); Chorev et al. *J Bone Min Res* 4: S270 (1989)). The peptide concentration for all peptides used is given as the value determined by amino acid analysis. The same batches of peptides were used in all studies.

Radioiodination

Radioiodination of hPTHrP-(1-36) was performed using a modification of the lactoperoxidase method as previously described (Orloff et al. *J. Biol. Chem.*, 264: 6097-6103 (1989); Orloff et al. *J Bone Min Res* 6: 279-287 (1991)). Purification of radioligand was accomplished by reverse-phase HPLC using a 30 cm µ-Bondapak C18 column (Waters Associates, Milford, Mass.). The radioligand prepared and purified in this manner is composed almost exclusively of the monoiodinated form. The specific activity ranged from 300-450 µCi/µg at the time of iodination. The radioligand displayed full biological activity in the canine renal adenylate cyclase assay when compared to the unlabeled peptide (Orloff et al. *J. Biol. Chem.*, 264: 6097-6103 (1989)).

Cell Culture

The human osteoblast-like osteosarcoma cell line, SaOS-2 (American Type Culture Collection, Rockville, Md.), was maintained in McCoy's medium supplemented with 10% fetal bovine serum, 2 mM L-glutamine, penicillin (50 U/ml), and streptomycin (50 µg/ml). The medium was changed every other day, and studies were performed at 5-7 days post confluence. Cell numbers were determined using a Coulter counter.

Preparation of Membranes

Highly purified human RCM were prepared using discontinuous sucrose gradient ultracentrifugation as previously described (Orloff et al. *J Bone Min Res* 6: 279-287 (1991)). All steps were performed in the presence of the following protease inhibitors: aprotinin [10 Kallikrein inhibitor units (KIU/ml], pepstatin (5 µg/ml), leupeptin (45 µg/ml), and phenylmethanesulfanylfluoride (10 µg/ml). Normal human kidney cortex was from four separate nephrectomy specimens removed for localized transitional cell carcinoma, renal cell carcinoma, or benign cysts. Renal function in all individuals was normal as assessed by serum creatinine and pyelography. Membranes were pooled, aliquoted, and stored at −70° C. for later use.

SaOS-2 cell membranes were prepared as previously described in detail. Briefly, postconfluent cells in 150 cm$^2$ flasks were scraped into membrane buffer [10 mM Tris HCl (pH 7.5), 0.2 mM MgCl$_2$, 0.5 mM EGTA, 1 mM dithiothreitol, leupeptin 45 µg/ml, pepstatin 5 µg/ml, aprotinin 10 KIU/ml, and phenylmethane sulfanyl-fluoride 10 µg/ml] at 0° C. Cell disruption was achieved by sonification and the suspension was centrifuged at 13,000×g for 15 min at 4° C. The pellet was resuspended with a Dounce glass homogenizer in membrane buffer (minus dithiothreitol) containing 250 mM sucrose. The suspension was layered onto a cushion of the membrane buffer containing 45% sucrose and centrifuged at 70,000×g for 30 min at 4° C. The membrane fraction layering at the interface was collected, diluted 5-fold with membrane buffer containing 250 mM sucrose, and recentrifuged. The pellet was resuspended in membrane buffer containing 250 mM sucrose, aliquoted, and stored at −70° C. Protein concentrations were determined by the method of Lowry using BSA as standard.

Receptor Binding Studies

The membrane binding assay utilizing human RCM at 30° C. has been described previously (Orloff et al. *J Bone Min Res* 6: 279-287 (1991)). Human RCM were added to a final concentration of 90 µg/ml. Total binding (TB) of $^{125}$I-(Tyr$^{36}$) hPTHrP-(1-36)NH$_2$ to human RCM varied between 11% and 20% of total counts added and nonspecific binding (NSB) ranged from 2.4-4.0%. Specific binding of $^{125}$I-(Tyr$^{36}$) hPTHrP-(1-36)NH$_2$ reached equilibrium by 30 min at 30° C. The incubation time of 30 min was used for subsequent equilibrium binding competition studies.

The binding assay for SaOS-2 membranes was conducted as for human RCM. Membranes were added to a final concentration of 112.5 µg/ml and specific binding reached equilibrium by 60 min at 30° C. TB ranged from 15-20% and NSB from 4.0-4.3%.

Binding to intact SaOS-2 cells was performed as described (Orloff et al. *Am J Physiol* 262: E599-E607 (1992)) with the following modifications. Binding studies were conducted at 15° C. in the presence of chymostatin (100 µg/ml) and bacitracin (200 µg/ml). Specific binding of $^{125}$I-(Tyr$^{36}$)hPTHrP-(1-36)NH$_2$ reached equilibrium by 150 min at 15° C. The incubation time of 150 min was therefore used for competitive binding studies. Cell viability, as assessed by exclusion of trypan blue, was greater than 95% at the end of a standard incubation. Total binding (TB) ranged from 18-23% of total radioactivity added and nonspecific binding (NSB) consistently ranged between 5-7%.

Stability of radioligand during incubation under respective assay conditions for each membrane preparation (human kidney and SaOS-2 membranes) and for the intact cell assay (SaOS-2) was examined by the ability of $^{125}$I-(Tyr$^{36}$) hPTHrP-(1-36) exposed to cells to rebind as compared to binding of "fresh" radioligand (Orloff et al., *J Biol Chem* 264:6097-6103, (1989); Orloff et al. *J Bone Min Res* 6: 279-287 (1991)). Specific rebinding of $^{125}$I-(Tyr$^{36}$) hPTHrP-(1-36) to human RCM, SaOS-2 membranes, and SaOS-2 intact cells was 92%, 98%, and 83% respectively. This indicated that significant degradation of radioligand did not occur under the respective assay conditions.

Adenylate Cyclase Assay

Adenylate cyclase-stimulating activity was examined in confluent SAOS-2 cells as previously described for ROS 17/2.8 cells (Merendino et al., *Science* 231:388-390, (1986)), with the following modification. The intact cell assay was conducted at 15° C., the same conditions employed for binding to intact SaOS-2 cells (vide supra). Time course experiments demonstrated that peak cAMP stimulation for PTHrP and PTH occurred after a 60 min incubation. Dose response curves for each peptide were thus generated using 60 min incubations at 15° C. under binding assay conditions. Under these conditions, maximal stimulation varied between 80- and 200-fold above basal activity.

Adenylate cyclase activity was examined in human kidney membranes and SaOS-2 cell membranes as previously described in detail for canine renal membranes (Orloff et al., *J Biol Chem* 264:6097-6103, (1989); Orloff et al. *J Bone Min Res* 6: 279-287 (1991)), with the following modifications: Time course experiments conducted at 30° C. demonstrated peak cAMP accumulation at 10 min for human kidney membranes and 30 min for SaOS-2 membranes. Therefore, dose response curves for each peptide were generated at 30° C. for 10 min in human kidney and 30° C. for 30 min in SaOS-2 membranes. As with the intact cell adenylate cyclase assays, kidney and bone cell membrane adenlyate cyclase assays were performed under binding assay conditions. Results are expresses as percentage of maximal cAMP stimulation in order to compare peptide dose responses from different experiments. Maximal cAMP stimulation varied from 3- to 8-fold above basal for human RCM, and from 2- to 7-fold for SaOS-2 membranes.

Data Analysis

IC$_{50}$ values for competitive binding experiments and EC$_{50}$ values for adenylate cyclase dose response curves were determined from the concentration of peptide yielding 50% of the maximal response. Statistical differences were assessed by paired and unpaired two-tailed Student's t test. Further analysis of competition binding data was carried out with the LIGAND computerized least-squares nonlinear curve-fitting program (Munson et al. *Anal Biochem* 107: 220-239 (1980)).

Results

Binding Studies

Competitive binding data using $^{125}$I-hPTHrP-(1-36) as radioligand in each of the three tissue preparations is shown in FIG. 9 and Table II (below). Binding of radioligand was completely displaced by all PTH and PTHrP analogs in each tissue examined, except for hPTHrP-(37-74), which, as expected, did not inhibit binding of $^{125}$I-hPTHrP-(1-36). Scatchard analysis of the data (FIG. 9, bottom panels) with the LIGAND computer program was compatible with a single class of high-affinity receptor sites in each tissue. Receptor numbers, calculated from the B$_{max}$ values, were 0.24±0.06 and 0.36±0.08 pmol/mg membrane protein for human RCM and SaOS-2 membranes, respectively, and 25,900±1500 receptors per cell for SaOS-2 intact cells.

Competition of radiolabeled P binding with PTH and PTHrP agonists was first compared in RCM and SaOS-2 membranes (Table II and FIG. 9, Panels A and B). In general, the relative affinity of selected agonists in RCM closely paralleled that observed in SaOS-2 membranes. rPTH-(1-34), bPTH-(1-34), and cPTHrP-(1-36) displayed similar relative affinities as compared to hPTHrP-(1,36), while (Nle$^{8,18}$Tyr$^{34}$)hPTH-(1-34) and cPTH-(1-34)NH$_2$ were less potent than hPTHrP-(1-36) in both assay systems. The relative affinity of bPTH-(1-84) was approximately 10-fold less than the amino-terminal analogs. Overall, these studies disclosed no important differences between PTH/ PTHrP binding in bone as compared to kidney.

Adenylate Cyclase Assay

The relative affinity of the agonist analogs in the binding assays was reflected in their adenylate cyclase-stimulating potency, with two notable exceptions (Table II and FIG. 10). Although rPTH-(1-34) was similar in binding affinity to hPTHrP-(1-36) in RCM and SaOS-2 membranes, it was 10-fold more potent in stimulating adenylate cyclase in both membrane preparations. bPTH-(1-84), which displayed lower binding affinity, retained its lower relative potency as compared to hPTHrP-(1-36) in the SaOS-2 membrane adenylate cyclase assay, but it was essentially equipotent to hPTHrP-(1-36) in stimulating cAMP production in RCM.

In order to investigate whether differences existed between intact and broken cell preparations, SaOS-2 intact cells were also studied (Table III and FIGS. 9C and 10C). In general, the relative affinity and cAMP-stimulating potency of the peptide agonists that were tested closely paralleled the results in RCM and SaOS-2 membranes. However, the absolute potency for some of the amino-terminal analogs varied between 2- to 4-fold less than that observed in either SaOS-2 membranes or RCM. Interestingly, rPTH-(1-34) did not demonstrate enhanced second messenger coupling relative to its binding affinity in SaOS-2 cells (Table III), a pattern which had been observed in RCM and SaOS-2 membranes (Table II). The affinity of hPTHrP-(1-74) was substantially less than that of hPTHrP-(1-36), although this difference was greater for RCM (25-fold) than for SaOS-2 cells (9-fold). Interestingly, hPTHrP-(1-141) had 5-fold greater affinity than hPTHrP-(1-74) in both assays, but it remained less potent than hPTHrP-(1-36). The relative affinity of bPTH-(1-84) was similar to that of hPTHrP-(1-74), but as noted in the preceding paragraph, it did not display the enhanced coupling to adenylate cyclase in SaOS-2 cells or membranes as it had in RCM.

EXAMPLE 3

Characterization of PTHrP Analogs Using Canine Renal Receptors

The purpose of the present study was to compare the properties of renal receptors for PTH and PTHrP and determine if the two peptides interact with the same receptors. To accomplish this aim, the PTH-related peptide, $[Tyr^{36}]$ PTHrP-(1-36)amide (PTHrP-(1-36)), and $[Nle^{8,18},Tyr^{34}]$ hPTH-(1-34)amide (NNT-hPTH-(1-34)) were radioiodinated and used in competition binding studies using canine renal cortical membranes (CRMC) to assess the binding of several PTH and PTHrP analogs. The ability of these PTH and PTHrP analogs to stimulate adenylate cyclase was also examined. For a detailed description of the methods in the present example, see e.g., Orloff et al. *J. Biol. Chem.*, 264: 6097-6103 (1989), incorporated herein by reference.

Materials and Methods

Peptides

The PTH-related peptide $(Tyr^{36})$ PTHrP-(1-36)amide (PTHrP-(1-36)) was prepared by solid-phase synthesis as previously described (Stewart et al., *J. Clin. Invest.*, 81: 596-600 (1988)). PTHrP-(49-74) and $(Cys^5,Trp^{11},Gly^{13})$ PTHrP-(5-18) (P1-peptide) were prepared using similar solid-phase methods. Synthetic $[Nle^{8,18},Tyr^{34}]hPTH-(1-34)$ amide (NNT-hPTH-(1-34)) and bovine PTH (bPTH)(1-34) were purchased from Bachem Inc., Torrance, Calif. The peptide concentration for all peptides used is given as the value determined by amino acid analysis and not as the dry weight of the peptide.

Radio-iodination

Radio-iodination of the peptides PTHrP (1-36) and NHT-hPTH (1-34) was performed using a modification (Thorell et al., *Biochim. Biophys. Acta*, 251: 363-369 (1971)) of the lactoperoxidase method (Marchalonis, *Biochem. J.*, 113: 299-305 (1969)). The peptide (10 µg/10 µl) was mixed with Na$^{125}$I (1 mCi/10 µl) (Amersham, Arlington Heights, Ill.) and lactoperoxidase (2 µg) (Sigma Chemicals, St. Louis, Mo.). The reaction was initiated by the addition of hydrogen peroxide (20 µl of 0.03% H$_2$O$_2$) and was maintained by three further 20 µl at additions of 0.03% H$_2$O$_2$ at 2.5 min intervals for a total of 10 min. The iodination mixture was then applied to a C18 Sep-Pak cartridge (Waters Associates, Milford, Mass.). The cartridge was washed with 3 ml 0.1% TFA, and then eluted with 3 ml 75:25% acetonitrile: H$_2$O (v:v) containing 0.1% TFA into borosilicate glass test tubes containing 30 µL of 2% BSA. The eluate was lyophilized and purified by reverse-phase HPLC using a 30 cm u-Bondapak C18 column (Waters Associates). The column was equilibrated with H$_2$O containing 0.1% TFA and developed with acetonitrile in 0.1% TFA. For $^{125}$I NNT-PTH (1-34), the gradient employed was a 60 min linear gradient of 33-43% acetonitrile. For $^{125}$I PTHrP-(1-36), elution was accomplished with a 50 min linear 27-34% acetonitrile gradient. Eluted fractions were collected in borosilicate glass tubes (12×75 mm) containing 30 µl of 1% BSA and monitored for radioactivity in a gamma spectrometer.

Analysis of Radioligand

HPLC-purified radioligand was subjected to complete enzymatic digestion in 100 µl of a buffer consisting of Tris-HCl (50 mM) pH 7.5, NaCl (75 mM), and sodium aside (0.005%) (Brown et al., *Biochem.*, 20: 4538-4546 (1981)). A mixture of trypsin (1 µg/10 µl), carboxypeptidase Y (1 µg/10 µl), leucine aminopeptidase (1 µg/10 µl), and pronase E (2 µg/10 µl) (all from Sigma, St. Louis, Mo.) was added and digestion carried out at 37° C. for 24 hours. The reaction was stopped by adding 100 µl of 0.1% TFA. A 100 µl aliquot of the digest was injected, along with 2 nmol each of non-oiodotyrosine and diiodotyrosine standard, onto a C18 u-Bondapak column. The column was eluted with a linear gradient of 15-30% methanol in 0.1% TFA over 30 mm at a flow rate of 1.5 ml/mm, and fractions (600 µl) were counted. UV absorbance at 214 nm was monitored.

Preparation of Membranes

Highly purified canine renal cortical membranes (CRCM) were prepared using a modification of the procedure of Fitzpatrick et al. (*J. Biol. Chem.*, 244: 3561-3569 (1969)). The renal cortex from adult mongrel dogs was homogenized in 3 volumes (ml:gm) of 0.25 M sucrose containing 5.0 mM Tris HCl (pH 7.5), 1.0 mM EDTA, 6.5 KIU/ml aprotinin and 50 µg/ml bacitracin (SET buffer) at 4° C. with ten 30 second strokes of a motor-driven teflon pestle at 2000 RPM. The homogenate was filtered through one thickness of nylon mesh and centrifuged at 1475×g for 10 mm. The supernatant was discarded and the pellet resuspended in 1 volume of 2.0 M sucrose, 5 mM Tris HCl, 1 mM EDTA (pH 7.5), 6.5 KIU/ml aprotinin, and 50 µg/ml bacitracin. This was centrifuged at 13,300×g for 10 minutes and the pellet discarded. The supernatant was diluted 8-fold with ET buffer (5 mM Tris HCl, 1 mM EDTA (Ph 7.5), 6.5 KIU/ml aprotinin, and 50 µg/ml bacitracin) and centrifuged at 20,000×g for 15 min. The supernatant was discarded and the white upper layer of the pellet removed and resuspended in one volume of SET buffer. The 20,000×g centrifugation was repeated two more times, and the white pellet suspended in one volume of SET buffer. These are referred to as "crude CRCM."

Membranes were purified further by a modification of the procedure described by Segre et al. (*J. Biol. Chem.*, 254: 6980-6986 (1979)). The white pellet described above was centrifuged at 2200×g for 15 mm and the supernatant and upper portion of the resulting double-layered pellet was removed and resuspended in SET buffer. This was centrifuged at 20,000×g for 15 mm and the supernatant discarded. The pellet was then layered onto a discontinuous gradient of sucrose in 0.01 M Tris, 0.001 M Na$_2$EDTA (pH 7.5), 6.5 KIU/ml aprotinin, and 50 µg/ml bacitracin. The gradient consisted of 39% sucrose (2 ml), 37% sucrose (4 ml), and 32% sucrose (2 ml). The membranes were centrifuged at 25,000 rpm (75,000×g) for 90 mm at 4° C. Major bands were present at each interface in addition to a pellet at the bottom of the tube. Preliminary studies of the lightest fraction (not entering the sucrose) and the fraction at the 32%-37% interface indicated the highest specific binding and lowest non-specific binding. The lightest fraction, however, demonstrated less degradation of the radioligand in rebinding studies. Therefore, all subsequent experiments were conducted with this fraction except where specifically indicated.

The above membranes were diluted with three volumes of ET buffer, centrifuged for 15 min at 7,800×g, suspended in one volume SET, aliquoted into 750 µl aliquots and stored at −70° C. Membranes so prepared retained full receptor binding activity for at least a 6-month storage period. A single membrane preparation was used for all conventional binding experiments.

A second membrane preparation was performed using the same procedure as above, but in the presence of leupeptin (5 µg/ml), pepstatin (5 µg/ml), aprotinin (10 KIU/ml), N-ethylmaleimide (NEM) (1.0 mM), and phenylmethanesulfanyl fluoride (PMSF) (10 µg/ml) in all steps (Nissenson et al., Biochem., 26: 1874-1878 (1987)). Protein was measured by the method of Lowry using BSA as standard.

Receptor Binding Studies

Binding assays were conducted in siliconized 12×75 mm borosilicate glass test tubes at 20° C. in a final volume of 0.2 ml. The binding buffer consisted of 50 mM Tris HCl (pH 7.5), 4.2 mM $MgCl_2$, 0.3% BSA, 26 mM KCl, approximately 60-80×$10^3$ cpm/tube of radioligand, and, where appropriate, unlabeled peptides. Based on radioligand stability studies described below, bacitracin was added to a final concentration of 100 µg/ml for experiments conducted with $^{125}$I NNT-hPTH-(1-34) and 200 µg/ml for $^{125}$I PTHrP-(1-36). Binding was initiated by adding 50 µg membrane. At the end of the incubation periods described, 50 µl triplicate aliquots were layered onto 300 µl of iced binding buffer containing 1.0% BSA in 500 µl polypropylene tubes. The tubes were centrifuged at approximately 16,000×g for three min at 4° C. in a microcentrifuge. The supernatant was aspirated and the tip of the tube containing the membrane-associated radioligand was cut off. Radioactivity in both the pellet and supernatant was measured.

Total binding (TB) of radioligand varied between 7.2-14.6% of total counts added for $^{125}$I NNT-hPTH-(1-34) and 25.5-30.0% for $^{125}$I PTHrP-(1-36). Nonspecific binding (NSB) was 1.8±0.3% (±SEM) for $^{125}$I NNT-hPTH-(1-34) and 9.9±0.8% for $^{125}$I PTHrP-(1-36). Recovery of both radioligands from incubation and wash tubes was routinely in excess of 95%.

Adenylate Cyclase Assay

Adenylate cyclase-stimulating activity was examined using a guanyl nucleotide-amplified canine renal cortical membrane (CRCM) PTH-sensitive adenylate cyclase assay, performed as previously described in detail (Stewart et al., Proc. Natl. Acad. Sci. USA, 80: 1454-1478 (1987)). Briefly, synthetic PTHrP-(1-36) or bPTH-(1-34) was added in duplicate to assay tubes containing crude CRCM, and the conversion of α-[$^{32}$P]cAMP to [$^{32}$P]cAMP at 30° C. for 30 min was examined. Results are expressed as the percent increment in adenylate cyclase activity in tubes containing the peptides as compared with tubes containing vehicle only.

Adenylate cyclase-stimulating activity of both peptides was also examined using highly purified 32% interface membranes. Incubation was carried out under binding conditions at 20° C. for 20 min in the presence of the protease inhibitor, bacitracin (200 µg/ml). All other aspects of this assay were identical to the standard assay.

Data Analysis

Dissociation constants (Kd) were determined by Scatchard analysis of the data obtained from competitive binding experiments using radioligand and increasing concentrations of unlabeled ligand. In competition studies using an unlabeled competitor different from the radioligand, binding affinities (Ki) were derived from the $IC_{50}$ (concentration of unlabeled ligand displacing 50% of specific radioligand binding) using the computer program EBDA (McPherson, KINETIC, EBDA, LIGAND, LOWRY: A COLLECTION OF RADIOLIGAND BINDING ANALYSIS PROGRAMS, pp. 14-97, Elsevier, Amsterdam (1985)). Statistical differences were assessed by paired Student's t test. Further analysis of competition curves was carried out with the LIGAND computerized least squares nonlinear curve-fitting program of Munson and Rodbard (Anal. Biochem., 107: 220-239 (1980)), modified for microcomputer use by McPherson (Ibid.). Computer fits of a one- or two-binding site model were compared, indicating the statistically preferred model. Significance was determined using a partial F-test.

Results

Chacterization of Ligand Binding; Association

Figure 11:
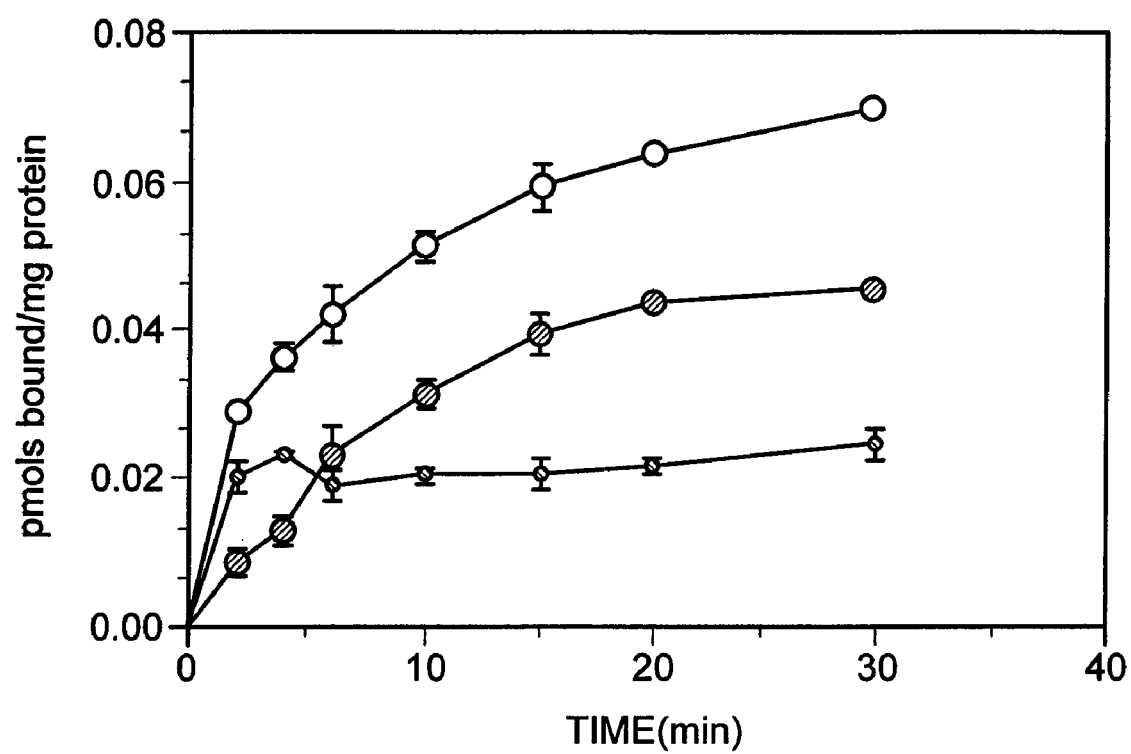
FIG. 11 illustrates a line graph depicting the time course for binding of PTHrP and PTH peptides including $^{125}$I [Nle$^{8,18}$, Tyr$^{34}$]-hPTH-(1-34)NH$_2$ to canine renal membranes at 20° C.: --□-- total binding of radioligand; --♦-- binding of radioligand in the presence of 10$^{-6}$M unlabeled bPTH-(1-34) (nonspecific binding); --●-- specific binding of radioligand. Points represent the mean±SEM of triplicate determinations. The SEM was too small to indicate in those points without error bars. Results are representative of those obtained in three experiments.

Specific binding of $^{125}$I NNT-hPTH-(1-34) reached equilibrium of 20 min at 20° C. (FIG. 11). Nonspecfic binding became relatively content by a 5 min at 2.5±0.1% (SEM) of total radioactivity added. For all subsequent equilibrium experiments, the incubation time was 20 min. Specific binding under these conditions ranged from 65-85% of total bound radioactivity for $^{125}$I NNT-hPTH-(1-34) and 55-75% of the total binding of $^{125}$I PTHrP(1-36)

Binding Studies

Figure 12:
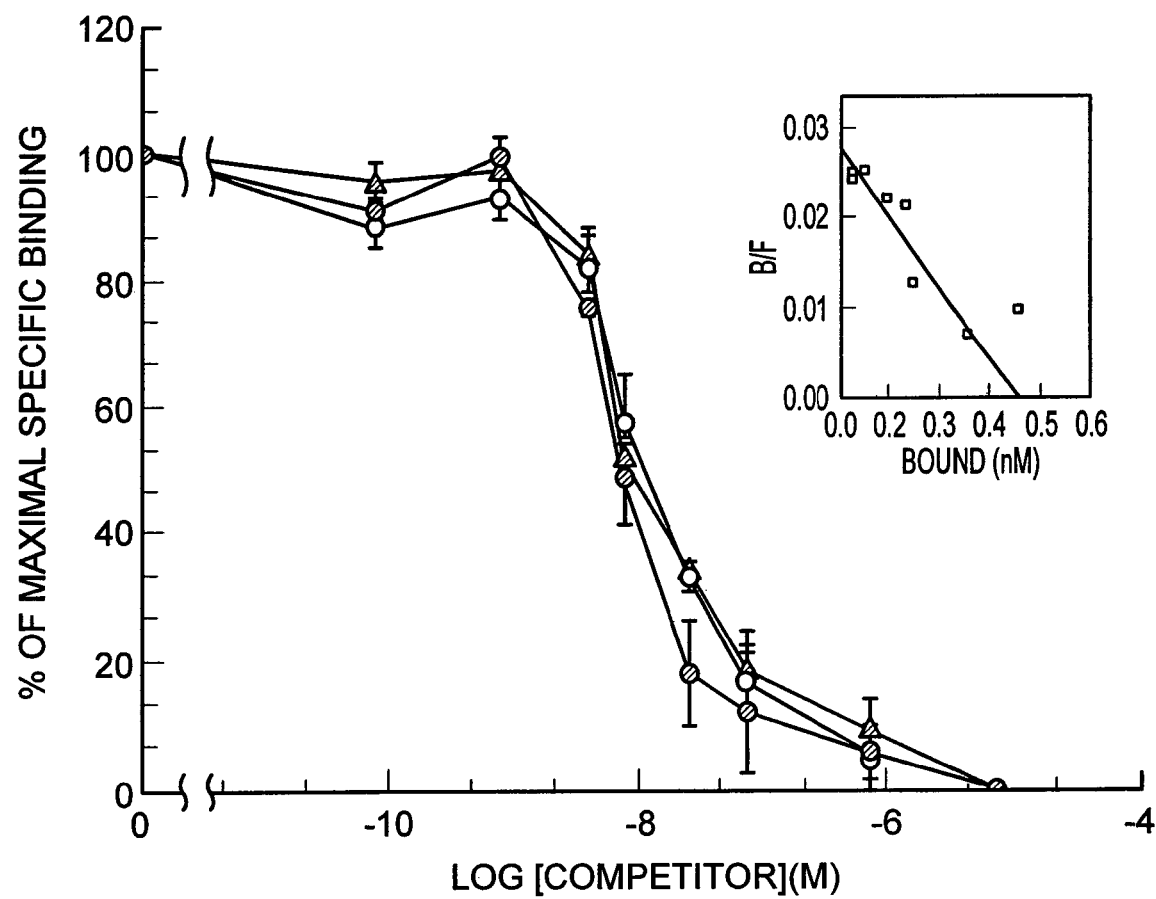
FIG. 12 is a line graph depicting competition binding studies of $^{125}$I-[Nle$^{8,18}$, Tyr$^{34}$] hPTH-(1-34)NH$_2$ to canine renal membranes at 20° C. with unlabeled [Nle$^{8,18}$, Tyr$^{34}$] hPTHh-(1-34)NH$_2$ (▲), bPTH-(1-34) (●), and [Tyr$^{36}$] PTHrP-(1-36)NH$_2$ (○). Points represent the mean±S.E. of triplicate determinations in three separate experiments (bPTH-(1-34) and [Tyr$^{36}$]PTHrP-(1-36) amide) or in two separate experiments [Nle$^{8,18}$, Tyr$^{34}$]hPTH-(1-34)NH$_2$). Individual points were expressed as a percentage of the specific binding determined in the absence of unlabeled peptide (percentage of maximal binding). Inset indicates Scatchard analysis of a representative experiment. B/F, bound/free.

Inhibition of binding of $^{125}$I-[Nle$^{8,18}$,Tyr$^{34}$]hPTH-(1-34) amide was performed using increasing concentrations of unlabeled [Nle$^{8,18}$,Tyr$^{34}$]hPTH-(1-34)amide, bPTH-(1-34), and PTHrP-(1-36) under equilibrium conditions (FIG. 12). The PTH analogues were slightly more potent than PTHrP-(1-36) in inhibiting binding (less than 2-fold) with a mean $K_i$ of 7.5 nM for [Nle$^{8,18}$, Tyr$^{34}$]hPTH-(1-34)amide and 6.1 nM for bPTH-(1-34). The binding affinity constant ($K_i$) for PTHrP-(1-36) was 11.5 nM (Table II, top).

Figure 13:
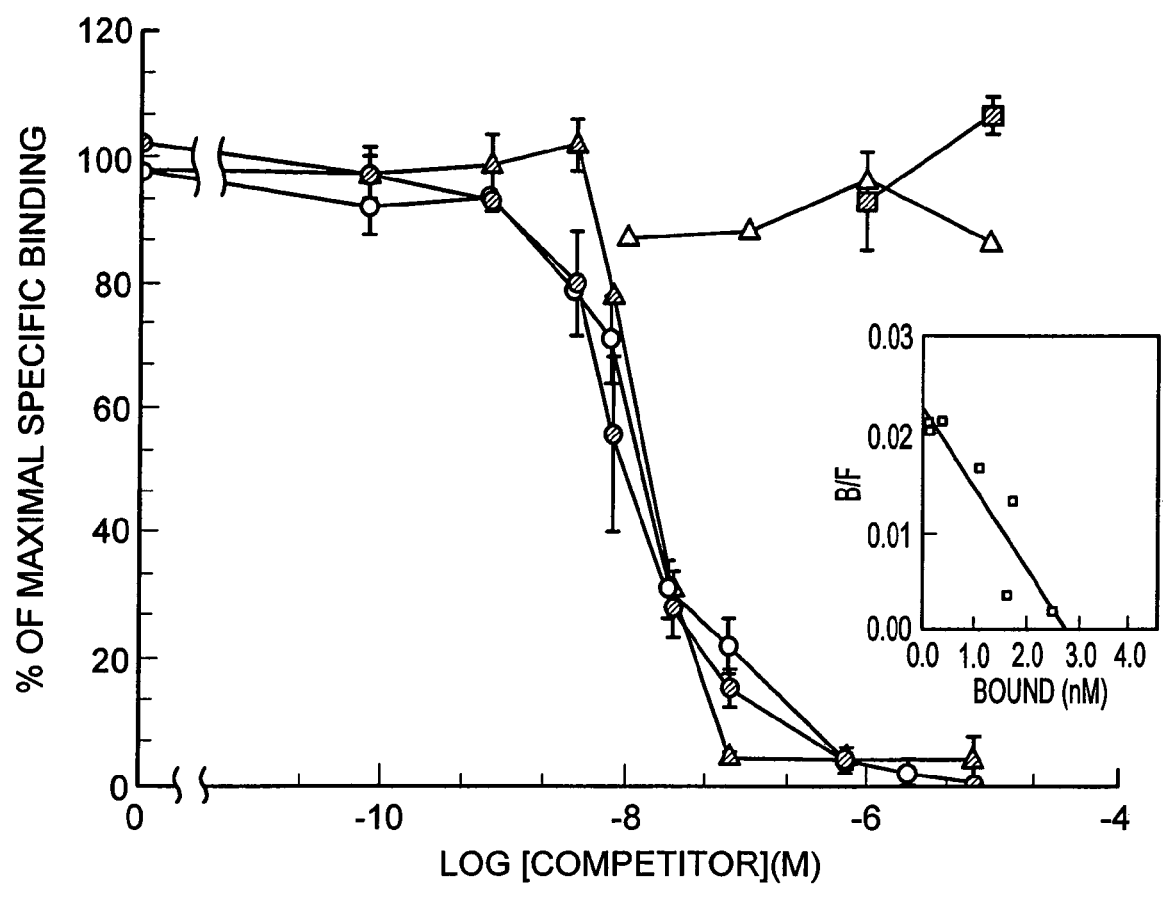
FIG. 13 is a line graph depicting competition binding studies of $^{125}$I-[Tyr$^{36}$]PTHrP-(1-36) NH$_2$ to canine renal membranes at 20° C. with unlabeled [Nle$_{8,18}$,Tyr$^{34}$]hPTH-(1-34)NH$_2$ (▲), bPTH-(1-34) (●), [Tyr$_{36}$]PTHrP-(1-36)NH$_2$ (○), PTHrP-(49-74) (Δ) and [Cys$^5$,Trp$^{11}$,Gly$^{13}$] PTHrP-(5-18) (P1-PEPTIDE) (■). Points represent the mean±S.E. of triplicate determinations in three separate experiments (bPTH-(1-34) and [Tyr$^{36}$] PTHrP-(1-36) amide) or in one experiment [Nle$^{8,18}$,Tyr$^{34}$]hPTH-(1-34)NH$_2$). Individual points were expressed as a percentage of the specific binding determined in the absence of unlabeled peptide (percent of maximal specific binding). Scatchard analysis (inset) of a representative experiment is shown. B/F, bound/free.

When $^{125}$I-PTHrP-(1-36) was used as the radioligand, all three synthetic peptides were approximately equipotent in inhibiting binding (FIG. 13). Binding dissociation constants for [Nle$^{8,18}$,Tyr$^{34}$]hPTH-1-34)amide, bPTH-(1-34), and PTHrP-(1-36) were 8.5, 10.5, and 14.1 nM, respectively (Table II, top). Both PTHrP-(49-74) and a synthetic 13-amino acid bio-inactive amino-terminal PTHrP ($P_1$ peptide) failed to inhibit binding of $^{125}$I-PTHrP-(1-36) to canine renal membranes (FIG. 13).

Representative Scatchard plots of the equilibrium binding data are presented in FIGS. 12 and 13. The $B_{max}$ value for PTH analogue was 2.73±0.31 pmol/mg protein and for PTHrP-(1-36) was 5.08±0.56 pmol/mg protein. Analysis of both sets of data with the LIGAND program demonstrated a single class of high affinity receptor sites; the data would not fit a two-site model.

In summary, each unlabeled PTH/PTHrP analog reduced the binding of each radioligand to the same degree, suggesting that the PTH/PTHrP analogs are binding to a similar or identical receptor. Scatchard analysis indicated a homogeneous class of high affinity receptor sites without significant cooperative binding interactions. Biologically inactive PTHrP fragments failed to displace the radioligand. These data, demonstrating similar binding affinities and $B_{max}$ values for PTHrP and PTH analogs in canine renal membranes, have also been observed in bone derived cells (Juppner et al., *J. Biol. Chem.*, 263: 8557-8560 (1988)), in canine renal membranes and UMR-106 osteosarcoma cells (Nissenson et al., *J. Biol. Chem.*, 263: 12866-12871 (1988)).

Adenylate Cyclase Assay

In contrast to their similar affinities in the binding assay, bPTH-(1-34) was substantially more potent than PTHrP-(1-36) in the canine renal cortical adenylate cyclase assay (Table II). This relationship was seen in both the standard assay conditions (30° C. for 30 min) and under binding assay conditions (20° C. for 20 min, with bacitracin). In the standard assay (30 min, 30° C.), bPTH-(1-34) had greater than 6-fold the potency of PTHrP-(1-36) with $K_m$ values of 0.06 and 0.40 nM, respectively. To exclude the possibility that selective destruction of PTHrP occurred during the assay in the presence of renal membranes, the adenylate cyclase assay was performed under binding conditions which had been demonstrated to result in negligible proteolysis of radioligands. Under conditions identical to the equilibrium binding assay (20° C., 20 min, with bacitracin), adenylate cyclase stimulation by bPTH-(1-34) was 15-fold greater than for PTHrP-(1-36). The $K_m$ values under binding assay conditions were 0.13 and 2.00 nM, respectively.

EXAMPLE 4

Characterization of PTHrP Analogs Using Ovariectomized, Osteopenic Rats

Candidate PTHrP analogs are evaluated for their effect on bone mass in ovariectomized rats, generally in accord with the procedures of Stewart et al., *J. Bone Min Res*, 15: 1517-1525 (2000), incorporated by reference herein. In the present Example, three PTH/PTHrP molecules were selected for direct comparison: PTH(1-34), PTHrP(1-36) and the PTH analog, SDZ-PTH-893 (Leu$^8$, Asp$^{10}$, Lys$^{11}$, Ala$^{16}$, Gln$^{18}$, Thr$^{33}$, Ala$^{34}$hPTH(1-34)). A six month study was performed in which adult (six month old) vehicle-treated ovariectomized (OVX) and sham OVX rats were compared to OVX rats receiving 40 µg/kg per day of either PTH(1-34), PTHrP(1-36) or PTH-SDZ-893.

Methods

Peptides and Peptide Administration

Recombinant human PTH(1-34) (rec hPTH(1-34) or LY333334) was prepared as described previously (Hirano et al., *J Bone Min Res* 14: 536-545 (1999); Frolick et al., *J Bone Min Res* 14: 163-72 (1999)). PTHrP(1-36) was prepared using solid phase synthesis as described previously (Everhart-Caye et al., *J Clin Endocrinol Metab* 81: 199-208 (1996); Henry et al., *J Clin Endocrinol Metab* 82: 900-906 (1997); Plotkin et al., *J Clin Endocrinol Metab* 83: 2786-2791 (1998)). The human and rat sequences of PTHrP(1-36) are identical. SDZ-PTH-893 (Leu$^8$, Asp$^{10}$, Lys$^{11}$, Ala$^{16}$, Gln$^{18}$, Thr$^{33}$, Ala$^{34}$hPTH(1-34) (Gamse et al., *J Bone Min Res* 12(*suppl*): S317 (1997)) was prepared using solid phase synthesis. The mass spectrum and amino acid composition were determined to be correct for each peptide and purity greater than 97% was confirmed by analytical reversed-phase HPLC. Peptides were administered subcutaneously in 0.001N HCl in saline containing 2% heat-inactivated ovariectomized (OVX) rat serum at pH 4.2.

Animals

All studies were performed using virus- and antibody-negative female Sprague-Dawley rats from Harlan Sprague-Dawley (Indianapolis, Ind.). All rats underwent sham ovariectomy or ovariectomy at 5 months of age. Studies began at six months of age, one month following ovariectomy or sham operation. Rats were maintained on a diet containing 0.5% calcium and 0.4% phosphorus. The light cycle was 12 hours.

Protocol

The protocol employed is described in schematic form in Table IV. Animals were randomly assigned to 17 groups of 10 as described in the Table. Except for animals in the first group which were sacrificed at five months of age, the remaining animals were observed for one month, and treatment with the various test peptides or vehicle was begun at six months of age. For the peptide-treated animals, the peptide was administered daily, subcutaneously at a dose of 40 µg/kg/day, in the vehicle described above. For vehicle-treated animals, vehicle alone was administered in an identical fashion.

Chemistries

Serum and urine chemistries as described in Table XI were performed using standard autoanalyser methods (Boehringer-Mannheim-Hitachi, Indianapolis, Ind.). Kidney calcium content was determined following extraction of whole kidneys in 5% trichloroacetic acid, followed by calcium measurement by calcium analyzer (Calcette, Midfield, Mass.).

Bone Mass Measurements

Bone mass was assessed using bone ash weight as well as DEXA measurements of the radius, femur and whole body. Whole body bone mineral content was determined using a Norland DXA Eclipse densitometer, and results are expressed in mg. Left femur bone mineral density in mg/cm$^2$ (BMD), bone mineral content in mg (BMC), and cross sectional area in cm$^2$ (X-area) were determined using a calibrated Hologic QDR 4500A densitometer coupled to Small Animal Regional High Resolution software, as performed by S. Orwoll at Oregon Health Sciences University, Portland Oreg. Left radius maximal length measurements were performed using Fowler/Sylvac Ultra-Cal II calipers (Newton, Mass.). Radius ash weight was determined as described (Hock et al., *J Bone Min Res* 7: 65-72 (1992); Hock et al., *Endocrinology* 125: 2022-2027 (1989)) following careful cleaning of the radius of non-skeletal tissue, dehydration in ether for 48 hours, followed by air drying for 24 hours, and ashing in a muffle furnace (Barnstead/Thernodyne, Dubuque, Iowa) at 850° C. for 16 hours. Ash weights were recorded in mg using a microbalance.

Bone Histomorphometry

Bone histomorphometry was performed on methyl methacrylate embedded sections of the right tibia of each animal following sacrifice as described in Table IV. Animals were labeled using calcein, 30 mg/kg, administered subcutaneously seven and three days prior to sacrifice. Standard histomorphometric measures were performed as shown in Tables IV-VI (Parfitt et al., *J Bone Min Res* 2: 595-610 (1987)).

Biomechanical Measures of Strength

Three-point bending on the femoral mid-shaft and compression of the L5 vertebral body were done at 37° C. Shearing of the femoral neck was done at room temperature. Complete methods for these tests have been reported previously (Sato et al., *Endocrinology* 138: 4330-4337 (1997); Turner and Burr, *Bone* 14: 595-608 (1993); Sato et al., *Endocrinology* 139: 4642-51 (1998), each incorporated herein by reference).

Statistical Analysis

Statistical analyses were performed using SAS software. Two-way analysis of variance was performed to determine if there were significant interactions between treatments and time, and if there were differences between agents. Pair-wise comparisons were done by contrast T-tests if significant interactions were present, and by Dunnett's test if no significant interactions were found. Level of significance was set at $p<0.05$.

Results

Figure 14:
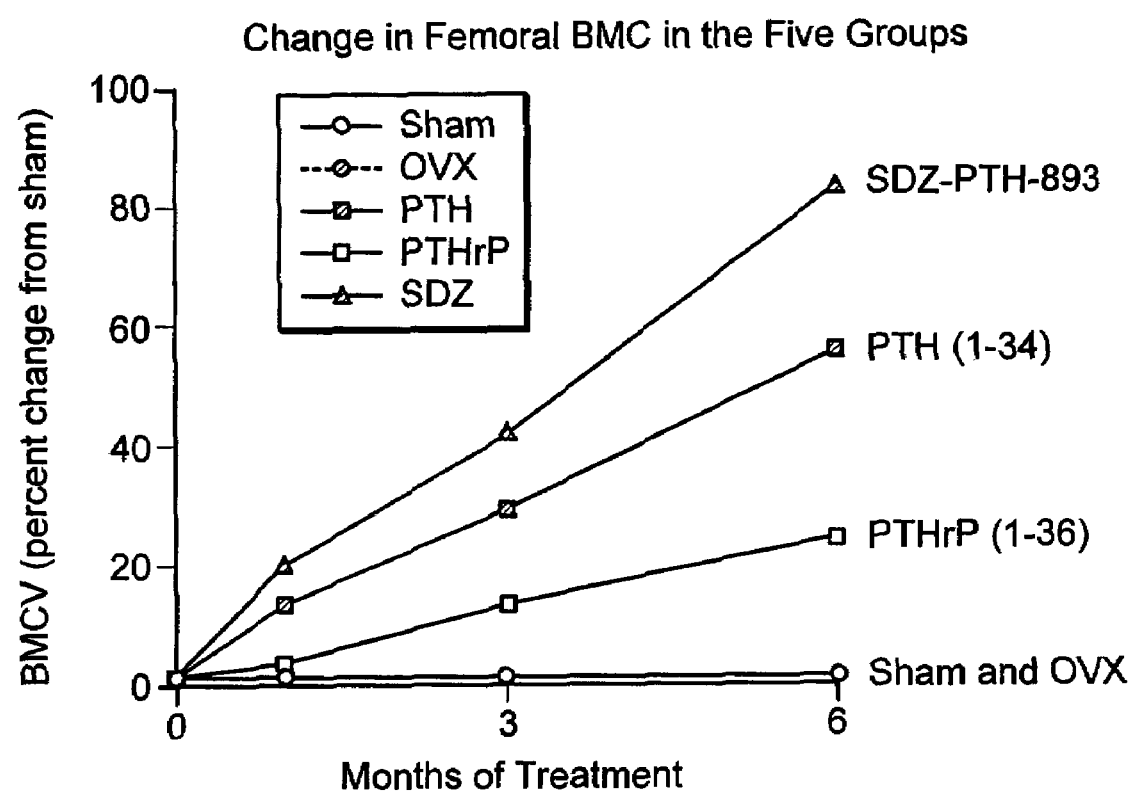
FIG. 14 illustrates the change in femoral bone mineral content in the five groups. BMC is shown as a percent change from the sham animals at each time point. Note that there is a progressive increase in femoral bone mineral content in each group of peptide-treated rats, and that the changes are highly significant in statistical terms.
Figure 15B:
FIG. 15 is a series of photomicrographs of the right proximal tibia following 90 days of treatment. A. Sham; B. OVX; C. SDZ-PTH-893; D. rhPTH(1-34); E. hPTHrP(1-36). Following ovariectomy, bone is lost in the proximal tibia. Treatment with either SDZ-PTH-893 or PTH(1-34) for 90 days not only restores lost bone but significantly increases trabecular bone volume over Sham. PTHrP(1-36) only partially restores lost bone. Magnification 5.5×.
Figure 15A:
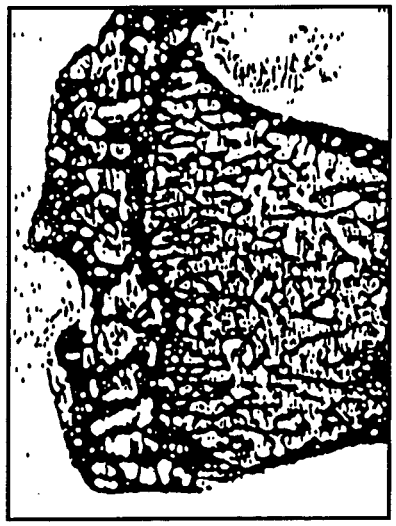
Figure 15E:
Figure 15D:
Figure 15C:

Statistically and quantitatively significant increases were observed in femur cross-sectional area, femoral bone mineral content, and bone mineral density of the PTH, PTHrP and SDZ-PTH groups, with a rank order of SDZ-PTH>PTH>PTHrP (see Table VIII). Femoral bone mineral content (FIG. 14) increased significantly and markedly in each of the peptide-treated groups, at each of the three time points assessed. No changes in femur length were observed due to treatment (see Table VIII).

There was no important difference in whole body BMC in the three peptide-treated groups as compared to their time-matched OVX controls (see Table VIII for details). Radius ash weight (see Table VIII) increased significantly during the study in the peptide-treated animal groups, increasing beyond the values observed in both the OVX and sham control groups.

Figure 16:
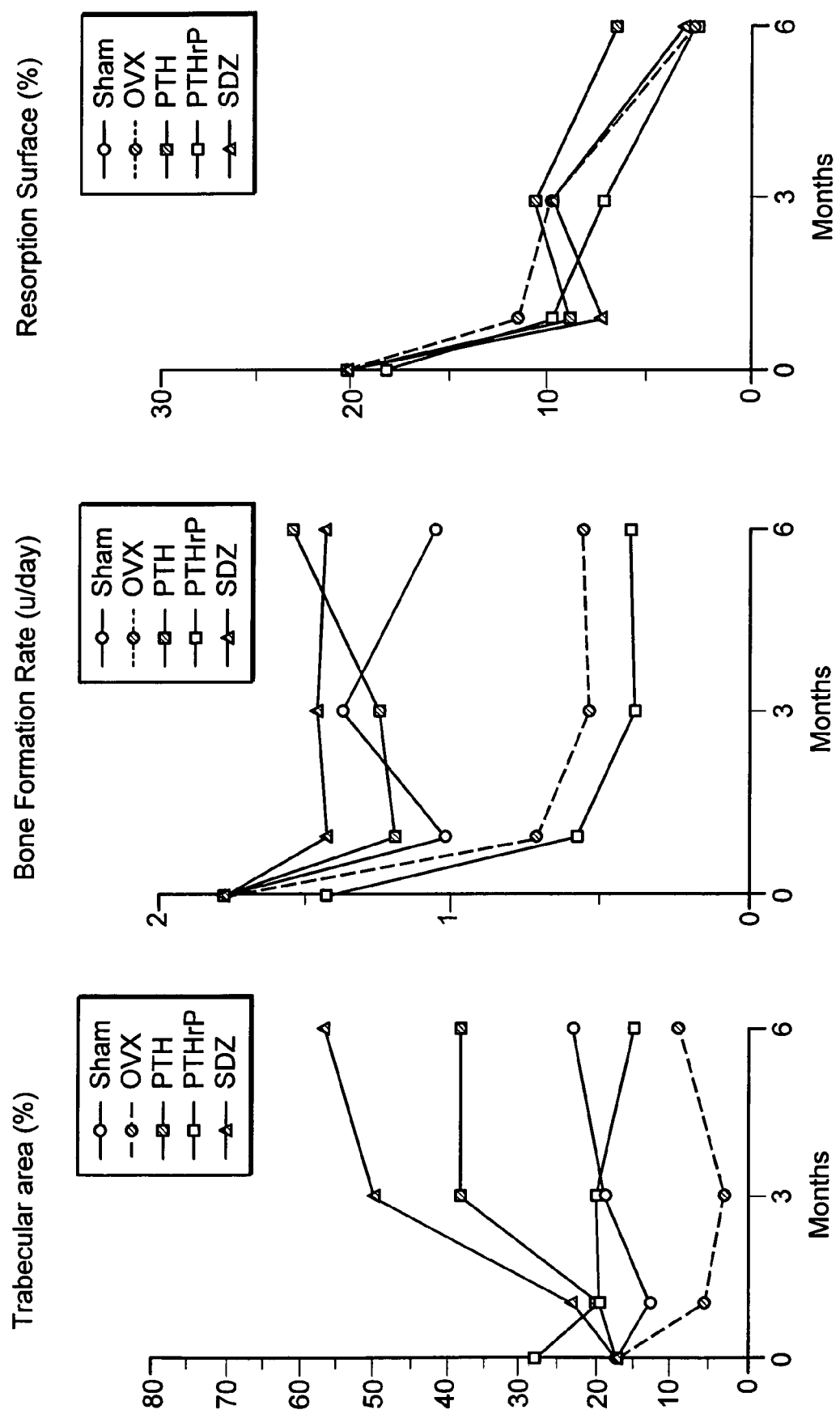
FIG. 16 depicts selected bone histomorphometric changes during the six month period. The key points are that: a) trabecular area, bone formation rate and resorption surface decline with age in the OVX groups; b) all three peptides had markedly positive effects compared to OVX controls on trabecular area and bone formation rate; and, c) despite this marked increase in bone formation rate, bone resorption rates were similar in months 1-6 among the treated and control groups.

Bone histomorphometry was performed in order to assess structural features of the skeletal changes as well as changes in bone turnover. As can be seen in FIGS. 15 and 16, trabecular area (Tb.Ar) declined markedly in the OVX control animals and remained depressed throughout the study, as compared to the sham animals. In contrast, marked increases in trabecular area occurred in all three peptide-treated groups, with the same rank order observed in the bone mass measures: SDZ-PTH>PTH>PMHrP. The increased Tb.Ar in treated animals was principally the result of increased trabecular thickness, which resulted in reduced trabecular separation (see Table V).

Bone formation (MS/BS) declined with age over the first 30 days in all animals (FIG. 15; see Table VI for greater detail). However, at each time point following initiation of treatment, bone formation parameters were significantly increased in all three peptide-treated animal groups as compared to the age-matched OVX and sham animals (Table VI, FIG. 15).

Bone resorption parameters declined with age in all five groups (FIG. 16; see Table VII for greater detail). In contrast to the differences in bone formation among the groups, there were no important differences in resorption parameters between OVX and sham animals at any time point.

Figure 17:
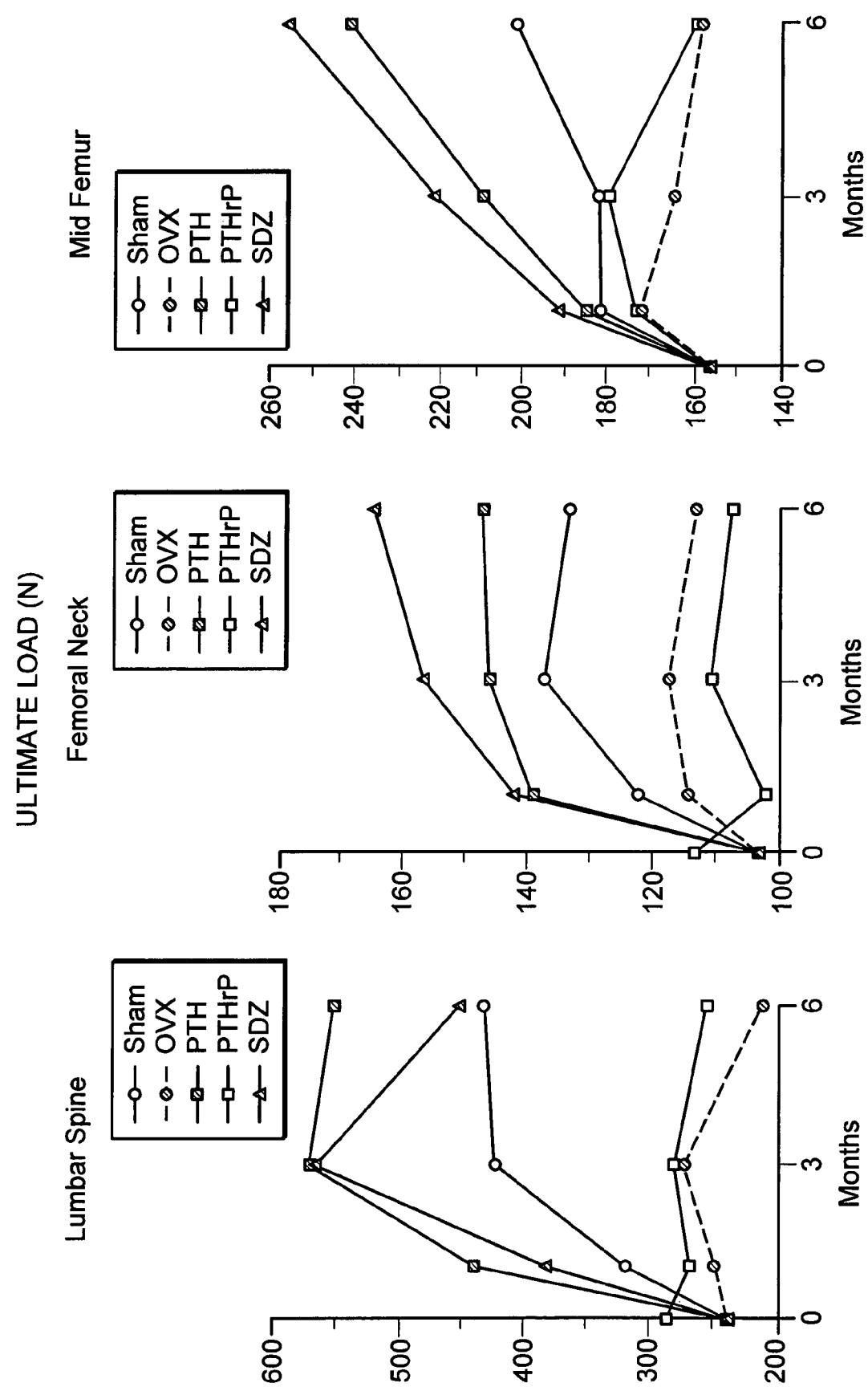
FIG. 17 illustrates changes in biomechanical strength (load to failure) during the six months of treatment. The key points are that: a) marked improvements in biomechanical measures occurred in all three groups for each of the three peptides; and b), improvements occurred at both predominantly trabecular and predominantly cortical sites.

Biomechanical measures improved in all three peptide treated groups (FIG. 17, and see Table IX and X for additional detail). At the lumbar spine, measures of biomechanical strength increased with each of the peptides. At the femoral neck, ultimate load also increased with all three peptides. The changes were statistically significant and quantitatively large. Importantly, for all three peptides, biomechanical measures at the lumbar spine and femoral neck exceeded those found not only in the OVX controls, but also the sham controls.

At the mid-shaft of the femur, a cortical bone site, similar findings were observed (FIG. 17). In general, the three peptide-treated groups showed augmented or improved biomechanical parameters as compared to both the sham and OVX control groups, and these changes were statistically, quantitatively, and functionally very significant (see Table X for complete details).

Body weight increased with increasing age in all groups throughout the study but there were no significant differences among the treated and control groups. Animals gained weight at approximately the same rate (see Table XI for details).

The mean serum calcium remained normal in the sham and OVX animals throughout the study (FIG. 18, see Table XI for complete details). This was true for the PTH- and PTHrP-treated animals as well. In contrast to these two treatment groups, frank hypercalcemia occurred in the SDZ-PTH-treated animals, with mean calcium concentrations of 11.3, 11.6 and 11.7 mg/dl at months 1, 3 and 6, respectively. These differences were significant statistically. They were also significant biologically in that four of the 30 SDZ-PTH-893-treated animals (13%) died during the study at 75, 83, 130 and 133 days of treatment. While the mean serum calcium was normal in the PTH group, one PTH-treated animal (3%) died with hypercalcemia at day 171. No PTHrP-treated animals died during the study.

Discussion

Candidate PTHrP analogs, or other skeletal anabolic agents, can be tested using the methods described above. PTHrP analogs, or other skeletal anabolic agents, useful in the methods of the present invention are expected to significantly increase the total bone calcium, trabecular calcium, cortical bone calcium, trabecular thickness, and bone volume over untreated OVX controls.

EXAMPLE 5

System and Methods for Design of Peptidomimetics and Small Molecules Having Biological Activity Similar to PTHrP and Skeletal Anabolic Agents As described above, PTHrP, PTH, and TIP peptides, as well as their receptors and resultant metabolic pathways, may be used to develop peptidomimetics and small molecule drugs, that are useful as agonists and antagonists of these skeletal anabolic agents. As used herein, a "peptidomimetic" refers to derivatives of the fragments or full length peptides of the skeletal anabolic agents PTHrP, PTH, or TIP, described above, that demonstrate biological activity involving modulation of bone mass, as well as mixtures, pharmaceutical compositions, and compositions comprising the same. A "small molecule drug" refers to a non-naturally occurring low-molecular weight compound, having similar activity. In either case, the biological activity of a peptidomimetic or small molecule drug can be agonistic or antagonistic to that of PTHrP, PTH, or TIP, or may include a spectrum of activity, i.e., may be antagonistic to PTH activity and agonistic to PTHrP activity.

As with PTH, the biological activity of PTHrP is associated with the N-terminal portion, with residues (1-30) minimally providing the biological activity. Truncated forms of the 39 amino acid tubular infundibular peptide (TIP) are also being assayed for biological activity.

Receptors for these agents are also targets for structural-based drug design. As described above, the 500-amino-acid PTH/PTHrP receptor (also known as the PTH1 receptor) belongs to a subfamily of GCPR that includes those for glucagon, secretin, and vasoactive intestinal peptide. The extracellular regions are involved in hormone binding, and the intracellular domains, after hormone activation, bind G protein subunits to transduce hormone signaling into cellular responses through stimulation of second messengers. These second messengers likewise provide drug targets.

Also described above, a second PTH receptor (PTH2 receptor) is expressed in brain, pancreas, and several other tissues. Its amino acid sequence and the pattern of its binding and stimulatory response to PTH and PTHrP differ from those of the PTH1 receptor. The PTH/PTHrP receptor responds equivalently to PTH and PTHrP, whereas the PTH2 receptor responds only to PTH. The endogenous ligand of this receptor appears to be tubular infundibular peptide-39 or TIP-39.

In one aspect of the invention, these compositions modulate, i.e., upregulate or downregulate PTH1 or PTH2 receptor activity. In another aspect, a system comprising structural information relating to the atomic coordinates obtained by x-ray diffraction of a PTHrP, PTH, or TIP peptide, fragment, peptidomimetic or small molecule drug is provided. In another embodiment, and antibody to a PTHrP, PTH, or TIP peptide, fragment, peptidomimetic or small molecule drug is provided. In even another embodiment, a purified crystalline preparation of a PTHrP, PTH, or TIP peptide, fragment, peptidomimetic or small molecule drug is provided.

Structures of PTH1 or PTH2 receptors, or a PTHrP, PTH, or TIP peptide, fragment, peptidomimetic or small molecule drug are obtained by x-ray diffraction of crystallized polypeptides, 2-D nuclear magnetic resonance spectroscopy of the same, or by similar methods of obtaining high resolution structures of biological materials. High resolution structures refer to structures solved to greater than 2.8 angstroms, and preferable greater than 2.3 angstroms, and are used to map the active sites of these receptors and their ligands. Structures are determined and interpreted using computer systems described in the art, e.g., having at least a memory bank, a display, a data input means, a processor and an instruction set comprising an algorithm for reading, interpreting and rendering the structural data, all of which are well known in the art, for example see, U.S. Pat. No. 6,273,598 to Keck et al., entitled, Computer system and methods for producing morphogen analogs of human OP-1, incorporated herein by reference. According to the present invention, such systems may be standalone or networked, i.e., through a packet switched network. Computer aided design (CAD) programs are employed to design peptidomimetics and small molecule agents having the appropriate receptor antagonist or agonist activities, based upon the obtained structural maps. Candidate agents are assayed for PTHrP, PTH, and TIP-like biological activity using the assays described herein, as well as similar assays known in the art.

TABLE I

| | Baseline Demographics | | |
|---|---|---|---|
| | PBO (n = 8) | PTHRP (n = 8) | p |
| Age (years) | 56.5 ± 1.3 | 61.5 ± 2.4 | ns |
| Height (cm) | 162.5 ± 2.3 | 161.6 ± 2.3 | ns |
| Weight (kg) | 62.1 ± 2.7 | 62.3 ± 3.0 | ns |
| BMI | 23.6 ± 1.1 | 24.0 ± 1.5 | ns |
| Plasma 25 D (nmol/L) | 61.9 ± 2.1 | 63.1 ± 2.1 | ns |
| Calcium intake (mg/day) | 940 ± 186 | 1438 ± 296 | ns |
| Yrs post Menopause | 13.5 ± 2.9 | 12.3 ± 2.3 | ns |
| Yrs on Estrogen | 8.4 ± 1.7 | 8.0 ± 1.5 | ns |
| # on Thyroxine | 1/8 | 0/8 | |
| Smoker | 2/8 | 0/8 | |
| L/S BMD (gm/cm$^2$) | 0.748 ± .03 | 0.763 ± .01 | ns |
| L/S BMD (T-score) | −2.71 ± .26 | −2.58 ± .12 | ns |
| T. Hip BMD (gm/cm$^2$) | 0.710 ± .02 | 0.722 ± .02 | ns |
| T. Hip BMD (T-score) | −1.9 ± .15 | −1.77 ± 021 | ns |
| FN BMD (gm/cm$^2$) | 0.572 ± .02 | 0.654 ± .03 | .05 |
| FN BMD (T-score) | −2.5 ± .21 | −1.95 ± .27 | ns |

TABLE II

In vitro activity of [Tyr$^{36}$] PTHrP-1-36) amide compared to bPTH-(1-34)

| | $K_d/K_i$ | | $K_m$ Standard assay nM | Binding conditions |
|---|---|---|---|---|
| Peptide | $^{125}$I-PTH | $^{125}$I-PTHrP | | |
| bPTH-(1-34) | 6.1 ± 1.5$^a$ | 10.5 ± 4.4$^b$ | 0.06 ± 0.01$^c$ | 0.13 ± 0.01$^a$ |
| PTHrP-(1-36) | 11.5 ± 2.5$^a$ | 14.0 ± 5.4$^b$ | 0.40 ± 0.07$^c$ | 2.00 ± 0.17$^a$ |

$^a$p = 0.03.
$^c$Not significant.
$^c$p < 0.002.
Binding studies were conducted at 20° C. using monoiodinated [Nle$^{8,18}$-Tyr$^{34}$]hPTH-(1-34) amide ($^{125}$I-PTH) or Tyr$^{36}$]PTHrP-(1-36)amide ($^{125}$I-PTHrP) as the radioligand. The K$_d$ values were determined by Scatchard analysis, and the K$_i$ values were derived from the IC$_{50}$ values. Adenylate cyclase stimulation was evaluated under standard assay conditions, employing partially purified canine renal membranes and 30-min incubations at 30° C. Adenylate cyclase stimulation was also evaluated under binding assay conditions, using highly purified canine renal membranes in the presence of bacitracin (200 μg/ml) and 20-min incubations at 20° C.

TABLE II-continued

In vitro activity of PTH and PTHrP agonists in human RCM (kidney membranes) as compared to SaOS-2 membranes

| Peptide | Binding (IC$_{50}$) (nM) | | Adenylate cyclase (EC$_{50}$) (nM) | |
|---|---|---|---|---|
| | Kidney membranes | SaOS membranes | Kidney membranes | SaOS membranes |
| (Tyr$^{36}$)hPTHrP-(1-36)NH$_2$ | 0.42 ± 0.07 | 0.64 ± 0.02 | 0.50 ± 0.10 | 0.51 ± 0.07 |
| (Nle$^{8,18}$Tyr$^{34}$)hPTH-(1-34) | 3.6 ± 0.7$^a$ | 2.0 ± 0.3$^a$ | 1.1 ± 0.1$^b$ | 1.9 ± 0.4$^c$ |
| bPTH-(1-34) | 0.39 ± 0.06 | 1.5 ± 0.4 | 0.26 ± 0.14 | 0.50 ± 0.06 |
| rPTH-(1-34) | 0.35 ± 0.15 | 0.56 ± 0.06 | 0.05 ± 0.01$^b$ | 0.09 ± 0.03$^b$ |
| cPTH-(1-34)NH$_2$ | 21.5 ± 8.5$^a$ | 20.0 ± 5.0$^b$ | 5.4 ± 0.1 | 16.3 ± 4.8$^d$ |
| (Tyr$^{36}$)cPTHrP-(1-36)NH$_2$ | 0.47 ± 0.22 | 1.1 ± 0.3 | 0.49 ± 0.06 | 0.87 ± 0.34 |
| bPTH-(1-84) | 5.1 ± 2.3$^b$ | 8.0 ± 2.0$^b$ | 0.59 ± 0.21 | 2.4 ± 0.2$^d$ |

Values are the mean ± SEM of two or more experiments for each peptide. Statistical analysis vs. (Tyr$^{36}$)hPTHrP-(1-36)NH$_2$:
$^a$P < 0.01.
$^b$P < 0.05.
$^c$P < 0.001.
$^d$P < 0.0001.

TABLE III

In vitro activity of PTH and PTHrP agonists in human RCM (kidney membranes) as compared to SaOS-2 intact cells

| Peptide | Binding (IC$_{50}$) (nM) | | Adenylate cyclase (EC$_{50}$) (nM) | |
|---|---|---|---|---|
| | Kidney membranes | SaOS cells | Kidney membranes | SaOS cells |
| [Tyr$^{36}$] hPTHrP-(1-36) NH$_2$ | 0.42 ± 0.07 | 1.5 ± 0.1 | 0.50 ± 0.10 | 1.0 ± 0.1 |
| hPTH-(1-34) | 1.9 ± 0.4$^a$ | 3.1 ± 0.3$^b$ | 0.70 ± 0.40 | 1.6 ± 0.0$^a$ |
| [Nle$^{8,18}$, Tyr$^{34}$] hPTH-(1-34) | 3.6 ± 0.7$^a$ | 2.8 ± 0.1$^b$ | 1.1 ± 0.1$^c$ | 2.3 ± 0.4$^b$ |
| bPTH-(1-34) | 0.39 ± 0.06 | 1.3 ± 0.1 | 0.26 ± 0.14 | 1.2 ± 0.1 |
| rPTH-(1-34) | 0.35 ± 0.15 | 0.9 ± 0.2$^c$ | 0.05 ± 0.01$^c$ | 0.9 ± 0.1$^b$ |
| cPTH-(1-34)NH$_2$ | 21.5 ± 8.5$^a$ | ◊$^d$ | 5.4 ± 0.1$^e$ | 3.9 ± 0.1$^b$ |
| [Tyr$^{36}$] cPTHrP-(1-36) NH$_2$ | 0.47 ± 0.22 | ◊$^d$ | 0.49 ± 0.06 | 0.8 ± 0.1 |
| hPTHrP-(1-74) | 9.5 ± 3.5$^a$ | 12.9 ± 1.4$^b$ | 7.8 ± 0.8$^a$ | 9.2 ± 1.0$^b$ |
| hPTHrP-(1-141) | 2.0 ± 0.1$^c$ | 2.4 ± 0.1$^a$ | 1.3 ± 0.4 | 1.9 ± 0.4$^e$ |
| bPTH-(1-84) | 5.1 ± 2.3$^c$ | 17.5 ± 2.5$^b$ | 0.59 ± 0.21 | 7.7 ± 1.4$^b$ |

Values are the mean ± SEM of two or more experiments for each peptide. Statistical analysis vs. [Tyr$^{36}$] hPTHrP-(1-36) NH$_2$:
$^a$P < 0.01.
$^b$P < 0.0001.
$^c$P < 0.05.
$^d$ ◊, These peptides were tested in SaOS-2 membranes, not in SaOS-2 cells (see Table II).
$^e$P < 0.001.

TABLE IV

| | | | Protocol | | | | | | |
|---|---|---|---|---|---|---|---|---|---|
| | | | Months of treatment | | | | | | |
| ID | Surgery | No/group | 1 | 2 | 3 | 4 | 5 | 6 | 7 |
| SB | Sham | 10 | kill | | | | | | |
| V0 | OVX | 10 | kill | | | | | | |
| S30 | Sham | 10 | hold | vehicle | | | | | |
| V30 | OVX | 10 | hold | vehicle | | | | | |
| P30 | OVX | 10 | hold | PTH | | | | | |
| R30 | OVX | 10 | hold | PTHrP | | | | | |
| A30 | OVX | 10 | hold | STZ | | | | | |
| S90 | Sham | 10 | hold | vehicle | vehicle | vehicle | | | |
| V90 | OVX | 10 | hold | vehicle | vehicle | vehicle | | | |
| P90 | OVX | 10 | hold | PTH | PTH | PTH | | | |
| R90 | OVX | 10 | hold | PTHrP | PTHrP | PTHrP | | | |
| A90 | OVX | 10 | hold | STZ | STZ | STZ | | | |
| S180 | Sham | 10 | hold | vehicle | vehicle | vehicle | vehicle | vehicle | vehicle |

TABLE IV-continued

Protocol

| | | | Months of treatment | | | | | | |
|---|---|---|---|---|---|---|---|---|---|
| ID | Surgery | No/group | 1 | 2 | 3 | 4 | 5 | 6 | 7 |
| V180 | OVX | 10 | hold | vehicle | vehicle | vehicle | vehicle | vehicle | vehicle |
| P180 | OVX | 10 | hold | PTH | PTH | PTH | PTH | PTH | PTH |
| R180 | OVX | 10 | hold | PTHrP | PTHrP | PTHrP | PTHrP | PTHrP | PTHrP |
| A180 | OVX | 10 | hold | STZ | STZ | STZ | STZ | STZ | STZ |

TABLE V

Structural Histomorphometry of the Right Proximal Tibia in Mature Ovariectomized (OVX) Rats Given Once Daily rec hPTH-(1-34), PTHrP-(1-36), or SDZ-PTH-893, for 30, 90, or 180 Days

| | Trabecular Area Tb.A. % | Trabecular Number Tb.N. #/min | Trabecular Space Tb.Sp. Φm | Trabecular Thickness Tb.Th. Φm |
|---|---|---|---|---|
| Baseline OVX | 17 ± 2 | 3.1 ± 0.2 | 281 ± 24 | 54 ± 4 |
| Baseline Sham | 28 ± 2 | 4.7 ± 0.2 | 156 ± 10 | 60 ± 2 |
| 30 Days | | | | |
| Sham | 20 ± 1[a] | 3.9 ± 0.2[a] | 206 ± 13[a] | 51 ± 2 |
| OVX | 6 ± 1 | 1.3 ± 0.3 | 847 ± 98 | 46 ± 2 |
| PTH(1-34) | 19 ± 2[a] | 2.3 ± 0.1[a,c] | 367 ± 28[a,c] | 81 ± 5[a,c] |
| PTHrP(1-36) | 13 ± 1[a,b,c] | 2.1 ± 0.1[a,c] | 436 ± 36[a,c] | 62 ± 3[a,b,c] |
| SDZ PTH 893 | 23 ± 3[a] | 2.5 ± 0.2[a,c] | 348 ± 42[a,c] | 93 ± 4[a,c] |
| 90 Days | | | | |
| Sham | 20 ± 2[a] | 3.7 ± 0.3[a] | 230 ± 27[a] | 52 ± 3 |
| OVX | 3 ± 1 | 0.6 ± 0.1 | 2178 ± 363 | 51 ± 6 |
| PTH(1-34) | 38 ± 3[a,c] | 2.4 ± 0.2[a,c] | 274 ± 34[a] | 158 ± 6[a,c] |
| PTHrP(1-36) | 19 ± 3[a,b] | 2.1 ± 0.2[a,c] | 398 ± 35[a,b,c] | 89 ± 5[a,b,c] |
| SDZ PTH 893 | 50 ± 5[a,c] | 2.4 ± 0.1[a,c] | 210 ± 23[a] | 205 ± 20[a,c] |
| 180 Days | | | | |
| Sham | 15 ± 3[a] | 2.7 ± 0.3[a] | 374 ± 78[a] | 53 ± 4 |
| OVX | 9 ± 7 | 0.7 ± 0.2 | 1923 ± 492 | 77 ± 32 |
| PTH(1-34) | 38 ± 3[a,c] | 2.3 ± 0.1[a] | 279 ± 29[a] | 163 ± 8[a,c] |
| PTHrP(1-36) | 23 ± 2[a,b,c] | 2.3 ± 0.2[a] | 361 ± 43[a] | 97 ± 4[a,b,c] |
| SDZ PTH 893 | 57 ± 4[a,c] | 3.3 ± 0.5[a,b] | 139 ± 26[a,b,c] | 183 ± 20[a,c] |

Data are expressed a mean ± SEM for 7 to 10 rats per group. Statistically significant differences, p < 0.05. Baseline data were not included in statistical analyses, and are shown for descriptive purposes only.
[a]versus time-matched OVX
[b]versus time-matched PTH (1-34)
[c]versus time-matched sham

TABLE VI

Bone Formation Measures of the Right Proximal Tibia in Mature Ovariectomized (OVX) Rats Given Once Daily rec hPTH-(1-34) (LY333334), PTHrP-(1-36), or SDZ PTH 893, a PTHrP Analog, for 30, 90, or 180 Days

| | Mineralizing Surface MS/BS (%) | Apposition Rate MAR (μm/d) | Bone Formation Rate BFR/BS (μm/d) |
|---|---|---|---|
| Baseline OVX | 37 ± 1 | 4.7 ± 0.8 | 1.77 ± 27 |
| Baseline Sham | 32 ± 2 | 4.4 ± 0.4 | 1.42 ± 20 |
| 30 Days | | | |
| Sham | 18 ± 2[a] | 2.8 ± 0.1[a] | 0.55 ± 6 |
| OVX | 26 ± 2 | 2.4 ± 0.1 | 0.69 ± 6 |
| rhPTH(1-34) | 49 ± 2[a,c] | 2.4 ± 0.1[c] | 1.18 ± 7[a,c] |
| PTHrP(1-36) | 39 ± 1[a,b,c] | 2.6 ± 0.1 | 1.00 ± 4[a,b,c] |
| SDZ PTH 893 | 56 ± 3[a,c] | 2.6 ± 0.1 | 1.42 ± 8[a,b,c] |
| 90 Days | | | |
| Sham | 14 ± 1[a] | 2.4 ± 0.2 | 0.36 ± 4 |
| OVX | 21 ± 2 | 2.4 ± 0.1 | 0.51 ± 6 |
| rhPTH(1-34) | 41 ± 1[a,c] | 3.0 ± 0.1[a,c] | 1.23 ± 4[a,c] |
| PTHrP(1-36) | 37 ± 1[a,b,c] | 3.6 ± 0.7[a] | 1.36 ± 28[a,b,c] |
| SDZ PTH 893 | 44 ± 2[a,c] | 3.3 ± 0.2[a,c] | 1.45 ± 10[a,c] |
| 180 Days | | | |
| Sham | 14 ± 2 | 2.6 ± 0.3 | 0.38 ± 7 |
| OVX | 19 ± 2 | 2.9 ± 0.2 | 0.54 ± 8 |
| rhPTH(1-34) | 40 ± 2[a,c] | 3.8 ± 0.7[c] | 1.53 ± 28[a,c] |
| PTHrP(1-36) | 29 ± 1[a,b,c] | 3.6 ± 0.5[c] | 1.05 ± 13[a,b,c] |
| SDZ PTH 893 | 45 ± 3[a,c] | 3.2 ± 0.2[c] | 1.43 ± 9[a,c] |

Data are expressed as mean ± SEM for 7 to 10 rats per group. Statistically significant differences, p < 0.05. Baseline data were not included in statistical analyses, and are shown for descriptive purposes only.
[a]versus time-matched OVX
[b]versus time-matched hPTH (1-34)
[c]versus time-matched sham

TABLE VII

Bone Resorption Measures of the Right Proximal Tibia in Mature Ovariectomized (OVX) Rats Given Once Daily rec hPTH-(1-34) (LY333334), PTHrP-(1-36), or SDZ-PTH-893, a PTHrP Analog, for 30, 90, or 180 Days

| | Resorbing Surface E.PM (%) | Osteoclast Surface Oc.PM (%) |
|---|---|---|
| Baseline OVX | 20.3 ± 1.4 | 9.0 ± 0.8 |
| Baseline Sham | 18.3 ± 1.8 | 6.1 ± 1.0 |

TABLE VII-continued

Bone Resorption Measures of the Right Proximal Tibia in Mature Ovariectomized (OVX) Rats Given Once Daily rec hPTH-(1-34) (LY333334), PTHrP-(1-36), or SDZ-PTH-893, a PTHrP Analog, for 30, 90, or 180 Days

|  | Resorbing Surface E.PM (%) | Osteoclast Surface Oc.PM (%) |
|---|---|---|
| 30 Days | | |
| Sham | 9.9 ± 2.1 | 2.1 ± 0.6 |
| OVX | 11.4 ± 1.7 | 3.7 ± 0.9 |
| rhPTH(1-34) | 8.6 ± 1.2 | 2.3 ± 0.6 |
| PTHrP (1-36) | 9.4 ± 1.7 | 2.4 ± 0.6 |
| SDZ PTH 893 | 7.1 ± 1.3[a] | 1.6 ± 0.6[a] |
| 90 Days | | |
| Sham | 7.0 ± 1.0 | 1.6 ± 0.5 |
| OVX | 9.6 ± 2.0 | 4.5 ± 1.1 |
| rhPTH(1-34) | 10.6 ± 1.3[c] | 2.6 ± 0.5 |
| PTHrP (1-36) | 10.3 ± 1.5 | 3.1 ± 0.6 |
| SDZ PTH 893 | 10.0 ± 1.3 | 2.0 ± 0.7 |
| 180 Days | | |
| Sham | 2.4 ± 0.4 | 0.8 ± 0.2 |
| OVX | 2.3 ± 1.1 | 1.2 ± 0.6 |
| rhPTH(1-34) | 6.4 ± 1.5 | 2.0 ± 0.4 |
| PTHrP (1-36) | 6.4 ± 1.1[a,c] | 2.0 ± 0.6 |
| SDZ PTH 893 | 3.0 ± 1.0 | 0.4 ± 0.3[b] |

Data are expressed as mean ± SEM for 7 to 10 rats per group. Statistically significant differences, $p < 0.05$.
Baseline data were not included in statistical analyses, and are shown for descriptive purposes only.
[a] versus time-matched OVX
[b] versus time-matched hPTH (1-34)
[c] versus time-matched sham.

TABLE VIII

Bone Mass of the Whole Body, Radius, or Femur in Mature Ovarlectomized Rats Given Once Daily rec hPTH-(1-34) (LY333334), PTHrP-(1-36), or SDZ PTH 893, a PTHrP Analog, for 30, 90, or 180 Days

|  | Whole Body BMC | Radius Ash Weight (mg) | Left Femur Length | Left Femur X Area | Left Femur BMC | Left Femur BMD |
|---|---|---|---|---|---|---|
| Baseline OVX[1] | 66 ± 1[a] | 55 ± 1 | 34.6 ± 0.2 | 1.62 ± 0.03 | 0.289 ± 0.008 | 0.177 ± 0.002 |
| Baseline Sham[2] | 53 ± 1 | 52 ± 1 | 33.6 ± 0.2 | 1.55 ± 0.03 | 0.294 ± 0.007 | 0.190 ± 0.004 |
| 30 Days | | | | | | |
| OVX | 66 ± 2[a] | 58 ± 2 | 34.9 ± 0.3 | 1.60 ± 0.05 | 0.289 ± 0.014 | 0.180 ± 0.004 |
| Sham | 58 ± 1 | 54 ± 1 | 34.3 ± 0.2[a,c] | 1.57 ± 0.03 | 0.300 ± 0.009 | 0.190 ± 0.004 |
| rhPTH(1-34) | 64 ± 3[c] | 60 ± 1[c] | 34.9 ± 0.3 | 1.68 ± 0.04[c] | 0.340 ± 0.011[a,c] | 0.200 ± 0.004[a] |
| PTHrP(1-36) | 67 ± 2[c] | 58 ± 1 | 34.7 ± 0.2 | 1.64 ± 0.03 | 0.313 ± 0.011[b] | 0.191 ± 0.004 |
| SDZ PTH 893 | 67 ± 2[c] | 62 ± 1[a,c] | 34.9 ± 0.3 | 1.73 ± 0.04[a,c] | 0.361 ± 0.009[a,c] | 0.210 ± 0.002[a,b,c] |
| 90 Days | | | | | | |
| OVX | 68 ± 4[a] | 52 ± 0 | 35.5 ± 0.4 | 1.65 ± 0.02 | 0.293 ± 0.006 | 0.178 ± 0.003 |
| Sham | 57 ± 2 | 54 ± 4 | 34.1 ± 0.3[a] | 1.57 ± 0.05 | 0.309 ± 0.017 | 0.198 ± 0.006[a] |
| rhPTH(1-34) | 69 ± 3[c] | 66 ± 1[a,c] | 35.7 ± 0.2[c] | 1.73 ± 0.03[c] | 0.401 ± 0.010[a,c] | 0.232 ± 0.005[a,c] |
| PTHrP(1-36) | 69 ± 4[c] | 60 ± 2[a,c] | 35.5 ± 0.2[c] | 1.71 ± 0.04[c] | 0.348 ± 0.007[a,b,c] | 0.203 ± 0.003[a,b] |
| SDZ PTH 893 | 70 ± 2[c] | 69 ± 1[a,c] | 35.7 ± 0.2[c] | 1.82 ± 0.02[a,b,c] | 0.442 ± 0.006[a,c] | 0.242 ± 0.003[a,c] |
| 180 Days | | | | | | |
| OVX | 72 ± 4[a] | 59 ± 1 | 35.3 ± 0.3 | 1.57 ± 0.04 | 0.280 ± 0.009 | 0.177 ± 0.004 |
| Sham | 59 ± 3 | 54 ± 2 | 34.3 ± 0.3[a] | 1.53 ± 0.04 | 0.291 ± 0.009 | 0.189 ± 0.004[a] |
| rhPTH(1-34) | 71 ± 3[c] | 72 ± 2[a,c] | 35.6 ± 0.3[c] | 1.84 ± 0.04[a,c] | 0.451 ± 0.012[a,c] | 0.234 ± 0.004[a,c] |

TABLE VIII-continued

Bone Mass of the Whole Body, Radius, or Femur in Mature Ovariectomized Rats Given Once Daily rec hPTH-(1-34) (LY333334), PTHrP-(1-36), or SDZ PTH 893, a PTHrP Analog, for 30, 90, or 180 Days

|  | Whole Body BMC | Radius Ash Weight (mg) | Left Femur | | | |
| --- | --- | --- | --- | --- | --- | --- |
|  |  |  | Length | X Area | BMC | BMD |
| PTHrP(1-36) | 68 ± 2$^c$ | 62 ± 1$^{a,b,c}$ | 35.1 ± 0.3$^c$ | 1.64 ± 0.03$^{b,c}$ | 0.357 ± 0.007$^{a,b,c}$ | 0.218 ± 0.003$^{ab,c}$ |
| SDZ PTH 893 | 68 ± 3$^c$ | 78 ± 3$^{a,c}$ | 36.4 ± 0.3$^c$ | 1.96 ± 0.05$^{a,c}$ | 0.530 ± 0.018$^{a,c}$ | 0.273 ± 0.005$^{a,c}$ |

Abbreviations:
X Area;
BMC = bone mineral concentration;
BMD = bone mineral density,
OVX = ovariectomized.
Data are expressed as mean ± standard error of the mean (SEM) for 10 rats per group.
Statistically significant differences are shown in Table 3.
$^a$versus time-matched OVX
$^b$versus time-matched PTH (1-34)
$^c$versus time-matched sham
$^1$OVX performed on day −1
$^2$BMC performed on day −30

TABLE IX

Gain in Body Weight and Serum Chemistries in Mature Ovariectomized Rats Given Once Daily rec hPTH-(1-34), PTHrP (1-36), or SDZ PTH 893, for 30, 90, or 180 Days

|  | Body Weight Gain (g) | Serum Calcium (mg/dL) | Serum Phosphate (mg/dL) | Serum Magnesium (mg/dL) | Serum Creatinine (mg/dL) | Serum Urea Nitrogen (mg/dL) | Kidney (mg Ca/gm wet wt) | Alkaline Phosphatase (IU/L) |
| --- | --- | --- | --- | --- | --- | --- | --- | --- |
| Baseline | — | 10.7 ± 0.1 | 7.7 ± 0.3 | 2.91 ± 0.07 | 0.74 ± 0.01 | 16.5 ± 0.6 | 0.20 ± 0.01 | 78 ± 5 |
| Sham Baseline OVX | — | 10.6 ± 0.1 | 7.3 ± 0.3 | 2.75 ± 0.08 | 0.76 ± 0.01 | 18.2 ± 0.6 | 0.25 ± 0.04 | 100 ± 4 |
| 30 Days | | | | | | | | |
| Sham | 1.0 ± 1.4 | 10.8 ± 0.1$^a$ | 7.9 ± 0.5 | 3.06 ± 0.10 | 0.79 ± 0.01 | 17.9 ± 0.7 | 0.22 ± 0.01 | 74 ± 6$^a$ |
| OVX | 1.7 ± 3.0 | 10.4 ± 0.1 | 7.3 ± 0.2 | 2.94 ± 0.08 | 0.78 ± 0.02 | 17.7 ± 0.9 | 0.27 ± 0.03 | 88 ± 3 |
| PTH (1-34) | 2.2 ± 1.3 | 10.7 ± 0.1$^a$ | 6.5 ± 0.2$^{ac}$ | 2.89 ± 0.06 | 0.80 ± 0.01 | 20.1 ± 0.8$^{ac}$ | 0.25 ± 0.02 | 83 ± 3 |
| PTHrP(1-36) | 2.2 ± 1.3 | 10.5 ± 0.1 | 6.8 ± 0.2 | 2.88 ± 0.07 | 0.78 ± 0.01 | 17.7 ± 0.4 | 0.29 ± 0.06 | 90 ± 5$^c$ |
| SDZ PTH 893 | −1.3 ± 1.8 | 11.3 ± 0.3$^{abc}$ | 5.5 ± 0.2$^{abc}$ | 2.90 ± 0.07 | 0.79 ± 0.01 | 19.1 ± 0.6 | 0.26 ± 0.01$^a$ | 83 ± 4 |
| 90 Days | | | | | | | | |
| Sham | 13.1 ± 3.8 | 10.2 ± 0.1$^a$ | 6.5 ± 0.2$^a$ | 2.74 ± 0.05 | 0.79 ± 0.02 | 20.1 ± 0.9 | 0.21 ± 0.03 | 71 ± 4$^a$ |
| OVX | 22.2 ± 5.3 | 10.1 ± 0.1 | 5.7 ± 0.2 | 2.57 ± 0.06 | 0.80 ± 0.01 | 19.5 ± 0.8 | 0.19 ± 0.02 | 103 ± 11 |
| PTH (1-34) | 30.6 ± 4.8 | 10.7 ± 0.1$^{ac}$ | 5.4 ± 0.2$^c$ | 2.70 ± 0.03 | 0.78 ± 0.02 | 22.1 ± 1.2 | 0.36 ± 0.06$^{ac}$ | 102 ± 6$^c$ |
| PTHrP(1-36) | 14.3 ± 3.9 | 10.3 ± 0.1$^b$ | 5.4 ± 0.3$^{abc}$ | 2.60 ± 0.08 | 0.78 ± 0.02 | 21.3 ± 1.3 | 0.21 ± 0.03$^b$ | 103 ± 4$^c$ |
| SDZ PTH 893 | 26.5 ± 3.7 | 11.6 ± 0.1$^{abc}$ | 4.7 ± 0.1$^{ac}$ | 2.71 ± 0.08 | 0.78 ± 0.01 | 22.7 ± 0.7$^a$ | 0.35 ± 0.06$^{ac}$ | 102 ± 7$^c$ |
| 180 Days | | | | | | | | |
| Sham | 34.4 ± 10.4 | 10.6 ± 0.1$^a$ | 7.1 ± 0.4$^a$ | 3.11 ± 0.04$^a$ | 0.81 ± 0.02 | 18.8 ± 1.2 | 0.22 ± 0.01 | 75 ± 5 |
| OVX | 52.3 ± 13.0 | 10.2 ± 0.2 | 6.2 ± 0.3 | 2.75 ± 0.08 | 0.81 ± 0.03 | 18.2 ± 0.9 | 0.24 ± 0.02 | 101 ± 6 |
| PTH (1-34) | 41.4 ± 16.2 | 10.9 ± 0.2$^a$ | 6.0 ± 0.3$^c$ | 2.80 ± 0.07$^c$ | 0.75 ± 0.02 | 19.8 ± 0.8 | 0.24 ± 0.02$^a$ | 108 ± 5$^c$ |
| PTHrP(1-36) | 45.8 ± 5.5 | 10.6 ± 0.1$^a$ | 6.0 ± 0.2$^c$ | 2.67 ± 0.05$^c$ | 0.72 ± 0.01$^{ac}$ | 17.4 ± 08$^b$ | 0.22 ± 0.01$^b$ | 108 ± 6$^c$ |
| SDZ PTH 893 | 33.7 ± 8.5 | 11.7 ± 0.6$^{ac}$ | 5.5 ± 0.3$^{ac}$ | 2.90 ± 0.08$^c$ | 0.87 ± 0.05$^b$ | 20.0 ± 1.0 | 1.28 ± 0.60$^{abc}$ | 100 ± 8$^c$ |

Abbreviation:
WW = Wet weight;
OVX = ovariectomized.
Data are expressed as mean ± standard error of the mean (SEM) for 10 rats per group.
Statistically siginficant differences, p < 0.05.
$^a$versus time-matched OVX
$^b$versus time-matched hPTH (1-34)
$^c$versus time-matched sham

TABLE X

Biomechanical Measures of Strength of the Femur Neck and Mid-Diaphysis of Mature OVX Rats Treated for 6 Months with hPTH 1-34 (PTH), PTHrP-(1-36) (PTHrP), or the PTH Analog, SDZ PTH 893

|  |  | Femur Neck Ultimate Load, (Fu) (N) | Mid-Femur | | | | | | | | |
|---|---|---|---|---|---|---|---|---|---|---|---|
|  | n |  | Cortical Thickness (t) (mm) | Moment of Inertia (I) (mm$^4$) | Ultimate Load (Fu) (N) | Stiffness (S) (N/mm) | Work to Failure (U) (mJ) | Ultimate Stress (Su) (MPa) | Young's Modulus (E) (Gpa) | Toughness (u) (MJ/m$^3$) |
| Baseline Sham | 10 | 113 ± 6 | 0.64 ± 0.01 | 4.2 ± 0.2 | 156 ± 4 | 460 ± 16 | 56 ± 4 | 204 ± 5 | 7.9 ± 0.3 | 5.5 ± 0.3 |
| Baseline OVX | 10 | 102 ± 5 | 0.65 ± 0.01 | 4.2 ± 0.1 | 157 ± 4 | 467 ± 15 | 56 ± 3 | 205 ± 7 | 8.0 ± 0.4 | 5.5 ± 0.3 |
| 30 Days | | | | | | | | | | |
| Sham | 9 | 102 ± 4 | 0.58 ± 0.02 | 4.1 ± 0.3 | 173 ± 4 | 538 ± 19 | 51 ± 3 | 234 ± 15 | 9.6 ± 0.6 | 5.2 ± 0.4 |
| OVX | 10 | 114 ± 6 | 0.56 ± 0.02 | 4.4 ± 0.3 | 172 ± 5 | 547 ± 20 | 53 ± 5 | 218 ± 10 | 9.1 ± 0.6 | 5.2 ± 0.4 |
| PTH | 10 | 139 ± 3$^{ac}$ | 0.64 ± 0.02$^{ac}$ | 4.5 ± 0.2 | 185 ± 6$^{ac}$ | 571 ± 13 | 63 ± 4 | 229 ± 7 | 9.1 ± 0.3 | 6.0 ± 0.3$^{c}$ |
| PTHrP | 10 | 122 ± 4$^{bc}$ | 0.58 ± 0.01$^{b}$ | 4.6 ± 0.1 | 182 ± 5 | 576 ± 17 | 61 ± 3 | 223 ± 6 | 8.9 ± 0.3 | 5.8 ± 0.3 |
| SDZ | 10 | 142 ± 7$^{ac}$ | 0.62 ± 0.02$^{a}$ | 4.5 ± 0.2 | 192 ± 7$^{ac}$ | 602 ± 18$^{ac}$ | 68 ± 5$^{c}$ | 237 ± 6$^{a}$ | 9.5 ± 0.3 | 6.5 ± 0.4$^{ac}$ |
| 90 Days | | | | | | | | | | |
| Sham | 7 | 110 ± 5 | 0.61 ± 0.03 | 4.3 ± 0.3 | 180 ± 5 | 571 ± 24$^{a}$ | 49 ± 3 | 231 ± 8$^{a}$ | 9.5 ± 0.4 | 4.9 ± 0.3 |
| OVX | 9 | 117 ± 5 | 0.52 ± 0.03 | 4.6 ± 0.3 | 164 ± 6 | 484 ± 22 | 46 ± 4 | 198 ± 8 | 7.5 ± 0.3 | 4.4 ± 0.4 |
| PTH | 10 | 146 ± 4$^{ac}$ | 0.71 ± 0.02$^{ac}$ | 4.5 ± 0.1 | 209 ± 4$^{ac}$ | 641 ± 14$^{ac}$ | 62 ± 3$^{a}$ | 251 ± 7$^{ac}$ | 10.0 ± 0.2$^{c}$ | 5.7 ± 0.3$^{a}$ |
| PTHrP | 10 | 137 ± 3$^{abc}$ | 0.64 ± 0.01$^{ac}$ | 4.3 ± 0.2 | 182 ± 4$^{ac}$ | 595 ± 17$^{ac}$ | 51 ± 2$^{a}$ | 226 ± 5$^{ac}$ | 9.8 ± 0.3$^{c}$ | 4.7 ± 0.2$^{a}$ |
| SDZ | 10 | 157 ± 5$^{ac}$ | 0.78 ± 0.02$^{bc}$ | 4.6 ± 0.2 | 221 ± 4$^{bc}$ | 692 ± 23$^{abc}$ | 65 ± 3$^{bc}$ | 265 ± 5$^{bc}$ | 10.6 ± 0.3$^{c}$ | 6.1 ± 0.3$^{bc}$ |
| 180 Days | | | | | | | | | | |
| Sham | 10 | 107 ± 5 | 0.64 ± 0.01 | 4.3 ± 0.2 | 159 ± 9 | 544 ± 25 | 30 ± 5 | 206 ± 17 | 9.2 ± 0.9 | 3.6 ± 0.5 |
| OVX | 6 | 113 ± 4 | 0.61 ± 0.02 | 4.5 ± 0.2 | 158 ± 10 | 563 ± 26 | 38 ± 4 | 188 ± 11 | 8.8 ± 0.4 | 3.5 ± 0.4 |
| PTH | 9 | 147 ± 6$^{ac}$ | 0.89 ± 0.01$^{ac}$ | 5.4 ± 0.3$^{ac}$ | 241 ± 9$^{ac}$ | 814 ± 31$^{ac}$ | 61 ± 4$^{ac}$ | 251 ± 8$^{ac}$ | 10.7 ± 0.4$^{ac}$ | 5.0 ± 0.3$^{ac}$ |
| PTHrP | 9 | 133 ± 4$^{abc}$ | 0.72 ± 0.02$^{abc}$ | 4.6 ± 0.1$^{b}$ | 202 ± 3$^{abc}$ | 767 ± 73$^{ac}$ | 53 ± 4$^{ac}$ | 239 ± 6$^{ac}$ | 11.9 ± 1.2$^{ac}$ | 4.7 ± 0.4$^{ac}$ |
| SDZ | 6 | 165 ± 8$^{ac}$ | 1.02 ± 0.02$^{ac}$ | 6.2 ± 0.6$^{ac}$ | 256 ± 13$^{ac}$ | 824 ± 48$^{ac}$ | 69 ± 6$^{ac}$ | 250 ± 13$^{ac}$ | 9.6 ± 0.6 | 5.7 ± 0.5$^{ac}$ |

Abbreviations:
n = number rats per group;
OVX = ovariectomized
Data are shown as mean ∀ SEM.
Statistically significant differeces, p < 0.05.
$^{a}$versus time-matched OVX
$^{b}$versus time-matched hPTH (1-34)
$^{c}$versus time-matched sham

TABLE XI

Gain in Body Weight and Serum Chemistries in Mature Ovariectomized Rats Given Once Daily rec hPTH-(1-34), PTHrP (1-36), or SDZ PTH 893, for 30, 90, or 180 Days

|  | Body Weight Gain (g) | Serum Calcium (mg/dL) | Serum Phosphate (mg/dL) | Serum Magnesium (mg/dL) | Serum Creatinine (mg/dL) | Serum Urea Nitrogen (mg/dL) | Kidney (mg Ca/gm wet wt) | Alkaline Phosphatase (IU/L) |
|---|---|---|---|---|---|---|---|---|
| Baseline Sham | — | 10.7 ± 0.1 | 7.7 ± 0.3 | 2.91 ± 0.07 | 0.74 ± 0.01 | 16.5 ± 0.6 | 0.20 ± 0.01 | 78 ± 5 |
| Baseline OVX | — | 10.6 ± 0.1 | 7.3 ± 0.3 | 2.75 ± 0.08 | 0.76 ± 0.01 | 18.2 ± 0.6 | 0.25 ± 0.04 | 100 ± 4 |
| 30 Days | | | | | | | | |
| Sham | 1.0 ± 1.4 | 10.8 ± 0.1$^{a}$ | 7.9 ± 0.5 | 3.06 ± 0.10 | 0.79 ± 0.01 | 17.9 ± 0.7 | 0.22 ± 0.01 | 74 ± 6$^{a}$ |
| OVX | 1.7 ± 3.0 | 10.4 ± 0.1 | 7.3 ± 0.2 | 2.94 ± 0.08 | 0.78 ± 0.02 | 17.7 ± 0.9 | 0.27 ± 0.03 | 88 ± 3 |
| PTH (1-34) | 2.2 ± 1.3 | 10.7 ± 0.1$^{a}$ | 6.5 ± 0.2$^{ac}$ | 2.89 ± 0.06 | 0.80 ± 0.01 | 20.1 ± 0.8$^{ac}$ | 0.25 ± 0.02 | 83 ± 3 |
| PTHrP(1-36) | 2.2 ± 1.3 | 10.5 ± 0.1 | 6.8 ± 0.2 | 2.88 ± 0.07 | 0.78 ± 0.01 | 17.7 ± 0.4 | 0.29 ± 0.06 | 90 ± 5$^{c}$ |
| SDZ PTH 893 | -1.3 ± 1.8 | 11.3 ± 0.3$^{abc}$ | 5.5 ± 0.2$^{abc}$ | 2.90 ± 0.07 | 0.79 ± 0.01 | 19.1 ± 0.6 | 0.26 ± 0.01$^{a}$ | 83 ± 4 |
| 90 Days | | | | | | | | |
| Sham | 13.1 ± 3.8 | 10.2 ± 0.1$^{a}$ | 6.5 ± 0.2$^{a}$ | 2.74 ± 0.05 | 0.79 ± 0.02 | 20.1 ± 0.9 | 0.21 ± 0.03 | 71 ± 4$^{a}$ |
| OVX | 22.2 ± 5.3 | 10.1 ± 0.1 | 5.7 ± 0.2 | 2.57 ± 0.06 | 0.80 ± 0.01 | 19.5 ± 0.8 | 0.19 ± 0.02 | 103 ± 11 |
| PTH (1-34) | 30.6 ± 4.8 | 10.7 ± 0.1$^{ac}$ | 5.4 ± 0.2$^{c}$ | 2.70 ± 0.03 | 0.78 ± 0.02 | 22.1 ± 1.2 | 0.36 ± 0.06$^{ac}$ | 102 ± 6$^{c}$ |
| PTHrP(1-36) | 14.3 ± 3.9 | 10.3 ± 0.1$^{b}$ | 5.4 ± 0.3$^{abc}$ | 2.60 ± 0.08 | 0.78 ± 0.02 | 21.3 ± 1.3 | 0.21 ± 0.03$^{b}$ | 103 ± 4$^{c}$ |
| SDZ PTH 893 | 26.5 ± 3.7 | 11.6 ± 0.1$^{abc}$ | 4.7 ± 0.1$^{ac}$ | 2.71 ± 0.08 | 0.78 ± 0.01 | 22.7 ± 0.7$^{a}$ | 0.35 ± 0.06$^{ac}$ | 102 ± 7$^{c}$ |
| 180 Days | | | | | | | | |
| Sham | 34.4 ± 10.4 | 10.6 ± 0.1$^{a}$ | 7.1 ± 0.4$^{a}$ | 3.11 ± 0.04$^{a}$ | 0.81 ± 0.02 | 18.8 ± 1.2 | 0.22 ± 0.01 | 75 ± 5 |
| OVX | 52.3 ± 13.0 | 10.2 ± 0.2 | 6.2 ± 0.3 | 2.75 ± 0.08 | 0.81 ± 0.03 | 18.2 ± 0.9 | 0.24 ± 0.02 | 101 ± 6 |
| PTH (1-34) | 41.4 ± 16.2 | 10.9 ± 0.2$^{a}$ | 6.0 ± 0.3$^{c}$ | 2.80 ± 0.07$^{c}$ | 0.75 ± 0.02 | 19.8 ± 0.8 | 0.24 ± 0.02$^{a}$ | 108 ± 5$^{c}$ |

TABLE XI-continued

Gain in Body Weight and Serum Chemistries in Mature Ovariectomized Rats Given Once Daily rec hPTH-(1-34), PTHrP (1-36), or SDZ PTH 893, for 30, 90, or 180 Days

|  | Body Weight Gain (g) | Serum Calcium (mg/dL) | Serum Phosphate (mg/dL) | Serum Magnesium (mg/dL) | Serum Creatinine (mg/dL) | Serum Urea Nitrogen (mg/dL) | Kidney (mg Ca/gm wet wt) | Alkaline Phosphatase (IU/L) |
|---|---|---|---|---|---|---|---|---|
| PTHrP(1-36) | 45.8 ± 5.5 | 10.6 ± 0.1$^a$ | 6.0 ± 0.2$^c$ | 2.67 ± 0.05$^c$ | 0.72 ± 0.01$^{ac}$ | 17.4 ± 0.8$^b$ | 0.22 ± 0.01$^b$ | 108 ± 6$^c$ |
| SDZ PTH 893 | 33.7 ± 8.5 | 11.7 ± 0.6$^{ac}$ | 5.5 ± 0.3$^{ac}$ | 2.90 ± 0.08$^c$ | 0.87 ± 0.05$^b$ | 20.0 ± 1.0 | 1.28 ± 0.0$^{abc}$ | 100 ± 8$^c$ |

Abbreviation:
WW = Wet weight;
OVX = ovariectomized.
Data are expressed as mean ± standard error of the mean (SEM) for 10 rats per group.
Statistically siginificant differences, p < 0.05.
[a]versus time-matched OVX
[b]versus time-matched hPTH (1-34)
[c]versus time-matched sham

EQUIVALENTS

From the foregoing detailed description of the specific embodiments of the invention, it should be apparent that a unique method of administering PTHrP, or an analog thereof, has been described resulting in safe and efficacious treatment of osteoporosis that minimizes the risk of, or eliminates negative side effects, such as hypercalcemia or the risk of developing osteogenic sarcomas. Although particular embodiments have been disclosed herein in detail, this has been done by way of example for purposes of illustration only, and is not intended to be limiting with respect to the scope of the appended claims that follow. In particular, it is contemplated by the inventor that substitutions, alterations, and modifications may be made to the invention without departing from the spirit and scope of the invention as defined by the claims. For instance, the choice of PTHrP analog, or the route of administration is believed to be matter of routine for a person of ordinary skill in the art with knowledge of the embodiments described herein.

I claim:

1. A method of increasing bone mass in a human patient in need thereof, said method comprising administering intermittently to said patient PTHrP at a dosage of at least 500 µg/day for a period of at least one month, wherein the bone mass density of said patient increases at a rate of at least 1% per month.

2. The method of claim 1, wherein the bone mass density of said patient increases at a rate of at least 1.5% per month.

3. The method of claim 1, wherein said human patient is afflicted with, or at risk of, primary or secondary osteoporosis.

4. The method of claim 1, wherein said human patient is afflicted with, or at risk of, a metabolic bone disorder selected from the group consisting of: osteomalacia, renal osteodystrophy, and other types of skeletal disorders with associated bone loss.

5. The method of claim 1, wherein PTHrP is administered subcutaneously.

6. A method of treating a human patient afflicted with osteoporosis, said method comprising administering intermittently PTHrP to said patient at a dosage at least about 500 µg/day for a period of 1-36 months, wherein the bone mass density of said patient increases at a rate of at least 1% per month.

7. The method of claim 6, wherein the bone mass density of said patient increases at a rate of at least 1.5% per month.

8. The method of claim 6, wherein said PTHrP is administered subcutaneously.

9. The method of claim 6, wherein said PTHrP is administered by the route of administration selected from the group consisting of: oral, intravenous, intraperitoneal, intramuscular, buccal, rectal, vaginal, intranasal, and aerosol administration.

10. The method of claim 6, wherein said PTHrP is administered until the bone mass density of said patient is restored.

* * * * *